US007083933B1

(12) United States Patent
Griffin

(10) Patent No.: US 7,083,933 B1
(45) Date of Patent: Aug. 1, 2006

(54) METHODS FOR IDENTIFICATION OF MODULATORS OF OSGPR116 ACTIVITY

(75) Inventor: Graeme Griffin, Centereach, NY (US)

(73) Assignee: Prosidion Limited, Oxford (GB)

( * ) Notice: Subject to any disclaimer, the term of this patent is extended or adjusted under 35 U.S.C. 154(b) by 0 days.

(21) Appl. No.: 10/841,183

(22) Filed: May 6, 2004

Related U.S. Application Data

(60) Provisional application No. 60/469,484, filed on May 9, 2003.

(51) Int. Cl.
*G01N 33/566* (2006.01)
*G01N 33/567* (2006.01)
*G01N 33/569* (2006.01)
*G01N 33/574* (2006.01)
*C07K 14/705* (2006.01)

(52) U.S. Cl. ............ 435/7.2; 435/7.21; 435/7.23; 435/7.31; 530/350

(58) Field of Classification Search ............ 435/7.2, 435/7.21
See application file for complete search history.

(56) References Cited

U.S. PATENT DOCUMENTS

| | | | |
|---|---|---|---|
| 6,221,660 B1 | 4/2001 | Bonini et al. ............... | 435/348 |
| 6,468,756 B1* | 10/2002 | Bonini et al. ............... | 435/7.1 |
| 2002/0068306 A1 | 6/2002 | Wu et al. ................... | 435/7.2 |
| 2003/0017528 A1 | 1/2003 | Chen et al. ................ | 435/69.1 |
| 2003/0018182 A1 | 1/2003 | Behan et al. ............... | 536/23.5 |
| 2003/0180813 A1 | 9/2003 | Ohishi et al. ............... | 435/7.2 |

FOREIGN PATENT DOCUMENTS

| | | |
|---|---|---|
| EP | 1092727 | 4/2001 |
| EP | 1338651 | 8/2003 |
| WO | WO00/22131 | 4/2000 |
| WO | WO 00/31258 | 6/2000 |
| WO | WO 01/32864 | 5/2001 |
| WO | WO01/87929 | 11/2001 |
| WO | WO 02/080860 | 10/2002 |
| WO | WO04/24943 | 3/2004 |
| WO | WO04/034968 | 4/2004 |
| WO | WO05/002524 | 1/2005 |

OTHER PUBLICATIONS

Wells (Sep. 18, 1990) Biochemistry 29(37): 8509-8517.*
Ngo et al. (Mar. 2, 1995) "The Protein Folding Problem and Tertiary Structure Prediction, Chapter 14: Computational Complexity Protein Structure Prediction, and the Levinthal Paradox" pp. 492-495.*
Bork (2000) *Genome Research* 10:398.*
Skolnick and Fetrow (2000) *Trends in Biotech.* 18(1): 34.*
Doerks et al. (Jun. 1998) *Trends in Genetics* 14(6): 248.*
Smith and Zhang (Nov. 1997) *Nature Biotechnology* 15:1222.*
Brenner (Apr. 1999) *Trends in Genetics* 15(4): 132.*
Bork and Bairoch (Oct. 1996) *Trends in Genetics* 12(10): 425.*
Barnett-Norris et al, 2002, J. Med. Chem. 45 : 3649-3659.*
Rocheville, M. et al (2000) Science 288:154-157.
Gether, U. et al. (2000) Endocrine Reviews 21:90-113.
Luttrel, L. et al. (1999) Science 283:655-661.
Wise, A. et al. (2002) DDT 7:235-246.
De Fonseca et al. (2001) Nature 414:209-212.
Gomez, R. et al. (2002) J. Neuroscience 22:9612:9617.
Fu, J. et al. (2003) Nature 425:90-93.
Guzmán, M. et al. (2004) J. Biol. Chem. 279:27849-27854.

* cited by examiner

*Primary Examiner*—Brenda Brumback
*Assistant Examiner*—Zachary C. Howard
(74) *Attorney, Agent, or Firm*—Alexander A. Stewart

(57) ABSTRACT

This invention relates to the identification of fatty acid or lipid amides that decrease food intake in mammals, including fatty acid ethanolamides, as ligands for the G-protein coupled receptor OSGPR116, and describes the first demonstration of a specific G-protein coupled receptor that is activated by fatty acid ethanolamides that inhibit feeding. The invention is directed to new methods for screening candidate drugs for their ability to modulate the activity of OSGPR116, and new pharmaceutical agents identified by these methods. It is also directed to the use of such agents in the manufacture of medicaments for the treatment of OSGPR116 mediated diseases, and methods of treating diseases such as obesity and diabetes by administering to an individual a therapeutic amount of a modulator of OSGPR116 identified by these methods.

25 Claims, 13 Drawing Sheets

Figure 1.

ATGGAATCATCTTTCTCATTTGGAGTGATCCTTGCTGTCCTGGCCTCCCTCA
TCATTGCTACTAACACACTAGTGGCTGTGGCTGTGCTGCTGTTGATCCACA
AGAATGATGGTGTCAGTCTCTGCTTCACCTTGAATCTGGCTGTGGCTGACA
CCTTGATTGGTGTGGCCATCTCTGGCCTACTCACAGACCAGCTCTCCAGCC
CTTCTCGGCCCACACAGAAGACCCTGTGCAGCCTGCGGATGGCATTTGTC
ACTTCCTCCGCAGCTGCCTCTGTCCTCACGGTCATGCTGATCACCTTTGAC
AGGTACCTTGCCATCAAGCAGCCCTTCCGCTACTTGAAGATCATGAGTGG
GTTCGTGGCCGGGGCCTGCATTGCCGGGCTGTGGTTAGTGTCTTACCTCAT
TGGCTTCCTCCCACTCGGAATCCCCATGTTCCAGCAGACTGCCTACAAAGG
GCAGTGCAGCTTCTTTGCTGTATTTCACCCTCACTTCGTGCTGACCCTCTCC
TGCGTTGGCTTCTTCCCAGCCATGCTCCTCTTTGTCTTCTTCTACTGCGACA
TGCTCAAGATTGCCTCCATGCACAGCCAGCAGATTCGAAAGATGGAACAT
GCAGGAGCCATGGCTGGAGGTTATCGATCCCCACGGACTCCCAGCGACTT
CAAAGCTCTCCGTACTGTGTCTGTTCTCATTGGGAGCTTTGCTCTATCCTG
GACCCCCTTCCTTATCACTGGCATTGTGCAGGTGGCCTGCCAGGAGTGTCA
CCTCTACCTAGTGCTGGAACGGTACCTGTGGCTGCTCGGCGTGGGCAACTC
CCTGCTCAACCCACTCATCTATGCCTATTGGCAGAAGGAGGTGCGACTGC
AGCTCTACCACATGGCCCTAGGAGTGAAGAAGGTGCTCACCTCATTCCTC
CTCTTTCTCTCGGCCAGGAATTGTGGCCCAGAGAGGCCCAGGGAAAGTTC
CTGTCACATCGTCACTATCTCCAGCTCAGAGTTTGATGGCTAA

Figure 2

MESSFSFGVILAVLASLIIATNTLVAVAVLLLIHKNDGVSLCFTLNLAVADTLI
GVAISGLLTDQLSSPSRPTQKTLCSLRMAFVTSSAAASVLTVMLITFDRYLAIK
QPFRYLKIMSGFVAGACIAGLWLVSYLIGFLPLGIPMFQQTAYKGQCSFFAVF
HPHFVLTLSCVGFFPAMLLFVFFYCDMLKIASMHSQQIRKMEHAGAMAGGY
RSPRTPSDFKALRTVSVLIGSFALSWTPFLITGIVQVACQECHLYLVLERYLWL
LGVGNSLLNPLIYAYWQKEVRLQLYHMALGVKKVLTSFLLFLSARNCGPERP
RESSCHIVTISSSEFDG

Figure 3

ATGGAGTCATCCTTCTCATTTGGAGTGATCCTTGCTGTCCTAACCATCCTC
ATCATTGCTGTTAATGCACTGGTAGTTGTGGCTATGCTGCTATCAATCTAC
AAGAATGATGGTGTTGGCCTTTGCTTCACCTTGAATCTGGCCGTGGCTGAT
ACCTTGATTGGCGTGGCTATTTCTGGTCTAGTTACAGACCAGCTCTCCAGC
TCTGCTCAGCATACACAGAAGACCTTGTGTAGCCTTCGGATGGCATTTGTC
ACTTCTTCTGCAGCTGCCTCTGTCCTCACCGTCATGCTGATTGCCTTTGACA
GATACCTTGCCATTAAGCAGCCCCTCCGTTACTTCCAGATCATGAATGGGC
TTGTGGCTGGAGCATGCATTGCAGGACTGTGGTTGGTATCTTACCTTATCG
GCTTCCTCCCACTCGGAGTCTCCATATTCCAGCAGACCACCTACCATGGAC
CCTGCAGCTTCTTTGCTGTGTTTCACCCAAGGTTTGTGCTGACCCTCTCCTG
TGCTGGCTTCTTCCCAGCTGTGCTCCTCTTTGTCTTCTTCTACTGTGACATG
CTCAAGATTGCCTCTGTGCACAGCCAGCAGATCCGGAAGATGGAACATGC
AGGAGCCATGGCCGGAGCTTATCGGCCCCACGGTCTGTCAATGACTTCA
AGGCTGTTCGTACTATAGCTGTTCTTATTGGGAGCTTCACTCTGTCCTGGT
CTCCCTTTCTCATAACTAGCATTGTGCAGGTGGCCTGCCACAAATGCTGCC
TTTACCAAGTGCTGGAAAAGTACCTGTGGCTCCTTGGAGTTGGCAACTCCC
TACTCAACCCACTCATCTATGCCTATTGGCAGAGGGAGGTTCGGCAGCAG
CTCTACCACATGGCCCTGGGAGTGAAAAGTTCTTCACTTCAATCCTCCTC
CTTCTCCCAGCCAGGAATCGTGGTCCAGAGAGGACCAGAGAAAGCGCCTA
TCACATCGTCACTATCAGCCATCCGGAGCTCGATGGCTAA

Figure 4

MESSFSFGVILAVLTILIIAVNALVVVAMLLSIYKNDGVGLCFTLNLAVADTLI
GVAISGLVTDQLSSSAQHTQKTLCSLRMAFVTSSAAASVLTVMLIAFDRYLAI
KQPLRYFQIMNGLVAGACIAGLWLVSYLIGFLPLGVSIFQQTTYHGPCSFFAV
FHPRFVLTLSCAGFFPAVLLFVFFYCDMLKIASVHSQQIRKMEHAGAMAGAY
RPPRSVNDFKAVRTIAVLIGSFTLSWSPFLITSIVQVACHKCCLYQVLEKYLWL
LGVGNSLLNPLIYAYWQREVRQQLYHMALGVKKFFTSILLLLPARNRGPERT
RESAYHIVTISHPELDG

Figure 5

| Oligo Name | Oligo Sequence | Gene | Cloning Vector | Restriction Site |
|---|---|---|---|---|
| OS116-BsaF1 | CTCTTCGGTCTCTCATGGAATCATCTTTCTCATTTGGAGTGATC (SEQ ID NO:5) | Human GPCR116 Homolog | Yeast Cp4258 | BsaI |
| OS116-HindIIIF | GTTGTCAAGCTTCCACCATGGAATCATCTTTCTCATTTGGAGTG (SEQ ID NO:6) | Human GPCR116 Homolog | Mammalian pcDNA3.1(+) | HindIII |
| OS116-XbaR1 | CTCTTCTCTAGACTTAGCCATCAAACTCTGAGCTGGAGATAGTG (SEQ ID NO:7) | Human GPCR116 Homolog | yeast/mammalian | XbaI |
| m116FBsmBI | TATATCGTCTCTCATGGAGTCATCCTTC (SEQ ID NO:8) | Mouse GPCR116 Homolog | Yeast Cp4258 | BsmBI |
| m116RXbaI | TATATTCTAGATTAGCCATCGAGCTCCGG (SEQ ID NO:9) | Mouse GPCR116 Homolog | Yeast Cp4258 | XbaI |

Figure 6

| Oligo Name | Oligo Sequence | Gene |
|---|---|---|
| OS116-F1 | AAAGATGGAACATGCAGGAGCC (SEQ ID NO:10) | OSGPR116 |
| OS116-R1 | GAGCTTTGAAGTCGCTGGGAG (SEQ ID NO:11) | OSGPR116 |
| OS116-Tqn1 | TGGCTGGAGGTTATCGATCCCCACG (SEQ ID NO:12) | OSGPR116 |
| TFIIB-F1 | CAGTGTGGATTTGATTACAACTGGG (SEQ ID NO:13) | TFIIB |
| TFIIB-R1 | TGTAGCTGCCATCTGTACTTGTTTAGG (SEQ ID NO:14) | TFIIB |
| TFIIB-Tqn1 | CTTCATGTCCAGGTTCTGTTCCAACCTTTGTC (SEQ ID NO:15) | TFIIB |

Figure 7

| Human Tissue | 116 | Human Tissue | 116 |
|---|---|---|---|
| Adipose | 0.012 | Colon | 0.016 |
| Liver | 0.000 | Lung | 0.000 |
| Pancreas | 0.078 | Trachea | 0.003 |
| Sk. Muscle | 0.000 | Leukocyte | 0.000 |
| Heart | 0.000 | Spleen | 0.000 |
| Aorta | 0.000 | Thymus | 0.001 |
| Brain | 0.000 | Adrenal | 0.000 |
| Hypothalamus | 0.000 | Kidney | 0.001 |
| Cerebellum | 0.000 | Bladder | 0.000 |
| Hippocampus | 0.000 | Breast | 0.002 |
| Pituitary | 0.003 | Ovary | 0.001 |
| Spinal Cord | 0.000 | Placenta | 0.002 |
| Stomach | 0.007 | Uterus | 0.001 |
| Intestine_small | 0.021 | Prostate | 0.000 |

SEQUENCE LISTING

<160> NUMBER OF SEQ ID NOS: 15

<210> SEQ ID NO 1
<211> LENGTH: 1008
<212> TYPE: DNA
<213> ORGANISM: Homo sapiens

<400> SEQUENCE: 1

```
atgaatcat  ctttctcatt  tggagtgatc  cttgctgtcc  tggcctccct  catcattgct      60
actaacacac tagtggctgt  ggctgtgctg  ctgttgatcc  acaagaatga  tggtgtcagt     120
ctctgcttca cctgaatct   ggctgtggct  gacaccttga  ttggtgtggc  catctctggc     180
ctactcacag accagctctc  cagcccttct  cggcccacac  agaagaccct  gtgcagcctg     240
cggatggcat ttgtcacttc  ctccgcagct  gcctctgtcc  tcacggtcat  gctgatcacc     300
tttgacaggt accttgccat  caagcagccc  ttccgctact  tgaagatcat  gagtgggttc     360
gtggccgggg cctgcattgc  cgggctgtgg  ttagtgtctt  acctcattgg  cttcctccca     420
ctcggaatcc ccatgttcca  gcagactgcc  tacaaagggc  agtgcagctt  ctttgctgta     480
tttcaccctc acttcgtgct  gaccctctcc  tgcgttggct  tcttcccagc  catgctcctc     540
tttgtcttct tctactgcga  catgctcaag  attgcctcca  tgcacagcca  gcagattcga     600
aagatggaac atgcaggagc  catggctgga  ggttatcgat  ccccacggac  tcccagcgac     660
ttcaaagctc tccgtactgt  gtctgttctc  attgggagct  ttgctctatc  ctggacccc     720 ttccttatca ctggcattgt  gcaggtggcc  tgccaggagt  gtcacctcta  cctagtgctg     780
gaacggtacc tgtggctgct  cggcgtgggc  aactccctgc  tcaacccact  catctatgcc     840
tattggcaga aggaggtgcg  actgcagctc  taccacatgg  ccctaggagt  gaagaaggtg     900
ctcacctcat tcctcctctt  tctctcggcc  aggaattgtg  gcccagagag  gcccagggaa     960
agttcctgtc acatcgtcac  tatctccagc  tcagagtttg  atggctaa             1008
```

<210> SEQ ID NO 2
<211> LENGTH: 335
<212> TYPE: PRT
<213> ORGANISM: Homo sapiens

<400> SEQUENCE: 2

```
Met Glu Ser Ser Phe Ser Phe Gly Val Ile Leu Ala Val Leu Ala Ser
1               5                   10                  15

Leu Ile Ile Ala Thr Asn Thr Leu Val Ala Val Ala Val Leu Leu Leu
            20                  25                  30

Ile His Lys Asn Asp Gly Val Ser Leu Cys Phe Thr Leu Asn Leu Ala
        35                  40                  45
```

-continued

| | | | | | | | | | | | | |
|---|---|---|---|---|---|---|---|---|---|---|---|---|
|Val|Ala|Asp|Thr|Leu|Ile|Gly|Val|Ala|Ile|Ser|Gly|Leu|Leu|Thr|Asp|
| |50| | | |55| | | |60| | | | | | |

Val Ala Asp Thr Leu Ile Gly Val Ala Ile Ser Gly Leu Leu Thr Asp
            50                  55                  60

Gln Leu Ser Ser Pro Ser Arg Pro Thr Gln Lys Thr Leu Cys Ser Leu
65                  70                  75                  80

Arg Met Ala Phe Val Thr Ser Ala Ala Ala Ser Val Leu Thr Val
                85                  90                  95

Met Leu Ile Thr Phe Asp Arg Tyr Leu Ala Ile Lys Gln Pro Phe Arg
            100                 105                 110

Tyr Leu Lys Ile Met Ser Gly Phe Val Ala Gly Ala Cys Ile Ala Gly
            115                 120                 125

Leu Trp Leu Val Ser Tyr Leu Ile Gly Phe Leu Pro Leu Gly Ile Pro
    130                 135                 140

Met Phe Gln Gln Thr Ala Tyr Lys Gly Gln Cys Ser Phe Phe Ala Val
145                 150                 155                 160

Phe His Pro His Phe Val Leu Thr Leu Ser Cys Val Gly Phe Phe Pro
                165                 170                 175

Ala Met Leu Leu Phe Val Phe Tyr Cys Asp Met Leu Lys Ile Ala
            180                 185                 190

Ser Met His Ser Gln Gln Ile Arg Lys Met Glu His Ala Gly Ala Met
            195                 200                 205

Ala Gly Gly Tyr Arg Ser Pro Arg Thr Pro Ser Asp Phe Lys Ala Leu
    210                 215                 220

Arg Thr Val Ser Val Leu Ile Gly Ser Phe Ala Leu Ser Trp Thr Pro
225                 230                 235                 240

Phe Leu Ile Thr Gly Ile Val Gln Val Ala Cys Gln Glu Cys His Leu
                245                 250                 255

Tyr Leu Val Leu Glu Arg Tyr Leu Trp Leu Leu Gly Val Gly Asn Ser
            260                 265                 270

Leu Leu Asn Pro Leu Ile Tyr Ala Tyr Trp Gln Lys Glu Val Arg Leu
            275                 280                 285

Gln Leu Tyr His Met Ala Leu Gly Val Lys Lys Val Leu Thr Ser Phe
    290                 295                 300

Leu Leu Phe Leu Ser Ala Arg Asn Cys Gly Pro Glu Arg Pro Arg Glu
305                 310                 315                 320

Ser Ser Cys His Ile Val Thr Ile Ser Ser Glu Phe Asp Gly
            325                 330                 335

<210> SEQ ID NO 3
<211> LENGTH: 1008
<212> TYPE: DNA
<213> ORGANISM: Mus sp.

<400> SEQUENCE: 3

```
atggagtcat ccttctcatt tggagtgatc cttgctgtcc taaccatcct catcattgct      60
gttaatgcac tggtagttgt ggctatgctg ctatcaatct acaagaatga tggtgttggc     120
ctttgcttca ccttgaatct ggccgtggct gataccttga ttggcgtggc tatttctggt     180
ctagttacag accagctctc cagctctgct cagcatacac agaagacctt gtgtagcctt     240
cggatggcat ttgtcacttc ttctgcagct gcctctgtcc tcaccgtcat gctgattgcc     300
tttgacagat accttgccat taagcagccc tccgttact tccagatcat gaatgggctt     360
gtggctggag catgcattgc aggactgtgg ttggtatctt accttatcgg cttcctccca     420
ctcggagtct ccatattcca gcagaccacc taccatggac cctgcagctt ctttgctgtg     480
tttcacccaa ggtttgtgct gaccctctcc tgtgctggct tcttcccagc tgtgctcctc     540
```

```
tttgtcttct tctactgtga catgctcaag attgcctctg tgcacagcca gcagatccgg      600
aagatggaac atgcaggagc catggccgga gcttatcggc ccccacggtc tgtcaatgac      660
ttcaaggctg ttcgtactat agctgttctt attgggagct tcactctgtc ctggtctccc      720
tttctcataa ctagcattgt gcaggtggcc tgccacaaat gctgccttta ccaagtgctg      780
gaaaagtacc tgtggctcct tggagttggc aactccctac tcaacccact catctatgcc      840
tattggcaga gggaggttcg gcagcagctc taccacatgg ccctgggagt gaaaaagttc      900
ttcacttcaa tcctcctcct tctcccagcc aggaatcgtg gtccagagag gaccagagaa      960
agcgcctatc acatcgtcac tatcagccat ccggagctcg atggctaa                 1008
```

<210> SEQ ID NO 4
<211> LENGTH: 335
<212> TYPE: PRT
<213> ORGANISM: Mus sp.

<400> SEQUENCE: 4

```
Met Glu Ser Ser Phe Ser Phe Gly Val Ile Leu Ala Val Leu Thr Ile
1               5                   10                  15

Leu Ile Ile Ala Val Asn Ala Leu Val Val Ala Met Leu Leu Ser
            20                  25                  30

Ile Tyr Lys Asn Asp Gly Val Gly Leu Cys Phe Thr Leu Asn Leu Ala
        35                  40                  45

Val Ala Asp Thr Leu Ile Gly Val Ala Ile Ser Gly Leu Val Thr Asp
    50                  55                  60

Gln Leu Ser Ser Ala Gln His Thr Gln Lys Thr Leu Cys Ser Leu
65                  70                  75                  80

Arg Met Ala Phe Val Thr Ser Ser Ala Ala Ser Val Leu Thr Val
                85                  90                  95

Met Leu Ile Ala Phe Asp Arg Tyr Leu Ala Ile Lys Gln Pro Leu Arg
            100                 105                 110

Tyr Phe Gln Ile Met Asn Gly Leu Val Ala Gly Ala Cys Ile Ala Gly
        115                 120                 125

Leu Trp Leu Val Ser Tyr Leu Ile Gly Phe Leu Pro Leu Gly Val Ser
    130                 135                 140

Ile Phe Gln Gln Thr Thr Tyr His Gly Pro Cys Ser Phe Phe Ala Val
145                 150                 155                 160

Phe His Pro Arg Phe Val Leu Thr Leu Ser Cys Ala Gly Phe Pro
                165                 170                 175

Ala Val Leu Leu Phe Val Phe Tyr Cys Asp Met Leu Lys Ile Ala
            180                 185                 190

Ser Val His Ser Gln Gln Ile Arg Lys Met Glu His Ala Gly Ala Met
    195                 200                 205

Ala Gly Ala Tyr Arg Pro Pro Arg Ser Val Asn Asp Phe Lys Ala Val
        210                 215                 220

Arg Thr Ile Ala Val Leu Ile Gly Ser Phe Thr Leu Ser Trp Ser Pro
225                 230                 235                 240

Phe Leu Ile Thr Ser Ile Val Gln Val Ala Cys His Lys Cys Cys Leu
                245                 250                 255

Tyr Gln Val Leu Glu Lys Tyr Leu Trp Leu Leu Gly Val Gly Asn Ser
            260                 265                 270

Leu Leu Asn Pro Leu Ile Tyr Ala Tyr Trp Gln Arg Glu Val Arg Gln
    275                 280                 285
```

```
Gln Leu Tyr His Met Ala Leu Gly Val Lys Lys Phe Phe Thr Ser Ile
    290                 295                 300

Leu Leu Leu Leu Pro Ala Arg Asn Arg Gly Pro Glu Arg Thr Arg Glu
305                 310                 315                 320

Ser Ala Tyr His Ile Val Thr Ile Ser His Pro Glu Leu Asp Gly
                325                 330                 335

<210> SEQ ID NO 5
<211> LENGTH: 44
<212> TYPE: DNA
<213> ORGANISM: Artificial
<220> FEATURE:
<223> OTHER INFORMATION: probe/primer

<400> SEQUENCE: 5
ctcttcggtc tctcatggaa tcatctttct catttggagt gatc            44

<210> SEQ ID NO 6
<211> LENGTH: 44
<212> TYPE: DNA
<213> ORGANISM: Artificial
<220> FEATURE:
<223> OTHER INFORMATION: probe/primer

<400> SEQUENCE: 6
gttgtcaagc ttccaccatg gaatcatctt tctcatttgg agtg            44

<210> SEQ ID NO 7
<211> LENGTH: 44
<212> TYPE: DNA
<213> ORGANISM: Artificial
<220> FEATURE:
<223> OTHER INFORMATION: probe/primer

<400> SEQUENCE: 7
ctcttctcta gacttagcca tcaaactctg agctggagat agtg            44

<210> SEQ ID NO 8
<211> LENGTH: 28
<212> TYPE: DNA
<213> ORGANISM: Artificial
<220> FEATURE:
<223> OTHER INFORMATION: probe/primer

<400> SEQUENCE: 8
tatatcgtct ctcatggagt catccttc                              28

<210> SEQ ID NO 9
<211> LENGTH: 29
<212> TYPE: DNA
<213> ORGANISM: Artificial
<220> FEATURE:
<223> OTHER INFORMATION: probe/primer

<400> SEQUENCE: 9
tatattctag attagccatc gagctccgg                             29

<210> SEQ ID NO 10
<211> LENGTH: 22
<212> TYPE: DNA
<213> ORGANISM: Artificial
<220> FEATURE:
<223> OTHER INFORMATION: probe/primer

<400> SEQUENCE: 10
```

-continued

```
aaagatggaa catgcaggag cc                                              22

<210> SEQ ID NO 11
<211> LENGTH: 21
<212> TYPE: DNA
<213> ORGANISM: Artificial
<220> FEATURE:
<223> OTHER INFORMATION: probe/primer

<400> SEQUENCE: 11
gagctttgaa gtcgctggga g                                               21

<210> SEQ ID NO 12
<211> LENGTH: 25
<212> TYPE: DNA
<213> ORGANISM: Artificial
<220> FEATURE:
<223> OTHER INFORMATION: probe/primer

<400> SEQUENCE: 12
tggctggagg ttatcgatcc ccacg                                           25

<210> SEQ ID NO 13
<211> LENGTH: 25
<212> TYPE: DNA
<213> ORGANISM: Artificial
<220> FEATURE:
<223> OTHER INFORMATION: probe/primer

<400> SEQUENCE: 13
cagtgtggat ttgattacaa ctggg                                           25

<210> SEQ ID NO 14
<211> LENGTH: 27
<212> TYPE: DNA
<213> ORGANISM: Artificial
<220> FEATURE:
<223> OTHER INFORMATION: probe/primer

<400> SEQUENCE: 14
tgtagctgcc atctgtactt gtttagg                                         27

<210> SEQ ID NO 15
<211> LENGTH: 32
<212> TYPE: DNA
<213> ORGANISM: Artificial
<220> FEATURE:
<223> OTHER INFORMATION: probe/primer

<400> SEQUENCE: 15
cttcatgtcc aggttctgtt ccaacctttg tc                                   32
```

METHODS FOR IDENTIFICATION OF MODULATORS OF OSGPR116 ACTIVITY

CROSS-REFERENCE TO RELATED APPLICATIONS

This application claims the benefit of U.S. Provisional Application No. 60/469,484, filed May 9, 2003, which is herein incorporated by reference in its entirety.

STATEMENT REGARDING FEDERALLY SPONSORED RESEARCH OR DEVELOPMENT

Not applicable.

REFERENCE TO SEQUENCE LISTING

A complete sequence listing section is included herein.

BACKGROUND OF THE INVENTION

This invention relates to the identification of fatty acid or lipid amides as ligands of the G-protein coupled receptor OSGPR116, and is directed to in vitro methods for screening candidate drugs for their ability to modulate the activity of OSGPR116, and to methods of treating disease by administering to an individual a therapeutic amount of a modulator of OSGPR116.

G-protein coupled receptors (GPCRs) are a super-family of membrane receptors that mediate a wide variety of biological functions. Upon binding of extracellular ligands, GPCRs interact with a specific subset of heterotrimeric G proteins that can, in their activated forms, inhibit or activate various effector enzymes and/or ion channels. All GPCRs are predicted to share a common molecular architecture consisting of seven transmembrane helices linked by alternating intracellular and extracellular loops. The extracellular receptor surface has been shown to be involved in ligand binding whereas the intracellular portions are involved in G-protein recognition and activation. Different G-protein alpha-subunits, and beta-gamma subunit complexes, preferentially stimulate or inhibit particular effector molecules to modulate various biological functions in a cell. Typical effector molecules include adenylate cyclase, phospholipases C and A2, cGMP phosphodiesterase-γ, and potassium, sodium and calcium channels. Additional regulation of GPCR activity is thought to occur via receptor oligomerization and interaction with the protein β-arrestin (e.g. see Rocheville, M. et. al. (2000) Science 288:154–157; Gether, U. (2000) Endocrine Reviews 21:90–113; Luttrel, L. M. et. al. (1999) Science 283:655–661). G-protein coupled receptors are found ubiquitously in all cell types within mammalian organisms. Many therapeutic agents targeting GPCR receptors have been successfully introduced onto the market, thereby establishing their value as targets for drug discovery and development (e.g. Wise, A. et al. 2002, DDT, 7:235–246). Over 30% of clinically marketed drugs are active on GPCRs.

It has been estimated that for about 40% of GPCRs in the human genome (excluding sensory receptors) the ligand remains unknown. Such GPCRs are commonly referred to as "orphan" receptors. For example, the primary structures of the human, rat and mouse forms of the orphan GPCR OSGPR116 (also known as OSGPR116) were recently described in two recent U.S. patents (U.S. Pat. No. 6,221,660, U.S. Pat. No. 6,468,756). In these patents the ligand for OSGPR116 was described as all-trans retinoic acid, which was shown to stimulate the production of cyclic AMP in host cells expressing recombinant receptor. OSGPR116 was described as a valuable tool for designing drugs for the treatment of over fifty diverse pathophysiological conditions, including obesity.

There is unquestionably a great unmet need for new drugs for the treatment of obesity, and thus amelioration of diseases associated with this condition, e.g. diabetes, cardiovascular diseases. Currently, more than 44 million Americans are considered obese by BMI index; that is, have a Body Mass Index ($Kg/m^2$) greater than or equal to 30. This reflects an increase of 74 percent since 1991. Pharmaceutical research has explored agents with a variety of mechanisms of action as potential anti-obesity drugs, e.g. Orlistat, which reduces the absorption of dietary fat, and is a pancreatic lipase inhibitor; and Sibutramine, an appetite suppressant, and an inhibitor of the reuptake of noradrenaline and serotonin. Additional appetite suppressants dexfenfluramine, fenfluramine and, phentermine have been withdrawn following reports of valvular heart disease associated with their use; these drugs were also associated with the rare but serious risk of pulmonary hypertension. However, appetite suppressant continue to be an attractive category for discovery, and more recently fatty acid ethanolamide compounds have shown promise as agents to inhibit food intake (WO 02/080860; de Fonseca, F. R. et.al. (2001) Nature, 414: 209–212). However, the molecular mechanism of fatty acid ethanolamides in modulating food intake has not been elucidated. Consequently there are considerable problems associated with developing such compounds of unknown mechanism of action. This problem has now been resolved with the surprising discovery that such fatty acid ethanolamide compounds are ligands of OSGPR116, thus providing a mechanism of action, and a basis for further assay and compound development.

SUMMARY OF THE INVENTION

The present invention is based on the finding that the G-protein coupled receptor OSGPR116 is able to act as a receptor for fatty acid or lipid amides and that cells transfected to express OSGPR116 gain the ability to elicit Gi/o (i.e. Gi and/or Go) G-protein mediated responses following exposure to fatty acid or lipid amides. Suitable lipid or fatty acid amides include fatty acid alkanolamides, including fatty acid ethanolamides. In one embodiment, lipid amides are selected from oleoyl ethanolamide, palmitoyl ethanolamide, stearoyl ethanolamide, linoleoyl ethanolamide, linolenoyl ethanolamide and oleamide, or a functional analog or homolog of one of these compounds. Identification of a ligand for OSGPR116 therefore facilitates the development of screening methods for identifying modulators of the OSGPR116 receptor.

Accordingly the invention further provides a method for identifying agents which modulate the activity of OSGPR116 receptor, which comprises determining whether the test agent interacts with OSGPR116. The method may comprise the use of OSGPR116 in combination with a fatty acid or lipid amide ligand. The invention further comprises the use of agents identified using the method of the invention in the treatment of diseases mediated by OSGPR116 and their use in the manufacture of a medicament for the treatment of OSGPR116 mediated diseases. Accordingly, the invention further provides a method of treatment of diseases or conditions mediated by OSGPR116 in an individual which comprises the administration of a therapeutically effective amount of an OSGPR116 receptor modulator.

(The present invention excludes by specific proviso the use of the compounds oleoylethanolamide, palmitoylethanolamide and elaidoylethanolamide when the method of the invention involves suppression of food intake). The invention also provides the use of a modulator of OSGPR116 in the manufacture of a medicament for the treatment of diseases or conditions mediated by OSGPR116 (with the proviso that the modulator is not oleoylethanolamide, palmitoylethanolamide or elaidoylethanolamide when the disease or condition is treated by suppression of food intake).

BRIEF DESCRIPTION OF THE FIGURES

FIG. 1: Nucleotide sequence encoding a human OSGPR116 receptor (SEQ ID NO:1).

FIG. 2: Deduced amino acid sequence of human OSGPR116 (SEQ ID NO:2).

FIG. 3: Nucleotide sequence of mouse homolog of OSGPR116 (SEQ ID NO:3).

FIG. 4: Deduced amino acid sequence of mouse homolog of OSGPR116 (SEQ ID NO:4).

FIG. 5: Oligonucleotides designed for PCR cloning of human and mouse homologs of OSGPR116. Oligonucleotides were designed based on a sequence found in the mouse genome sequence database (www.sanger.ac.uk) subsequent to BLAST analysis with the human OSGPR116 sequence. Oligonucleotides for the human homolog were based on the predicted sequence based on human genomic sequencing information.

FIG. 6: Oligonucleotides designed for quantitative RT-PCR using fluorogenic probe for OSGPR116.

FIG. 7: OSGPR116 expression profile in normal human tissues. Data is expressed as a ratio of TFIIB expression levels in the same tissues, and the experiment was conducted as detailed in the Materials and Methods section.

DETAILED DESCRIPTION OF THE INVENTION

Figure 8:
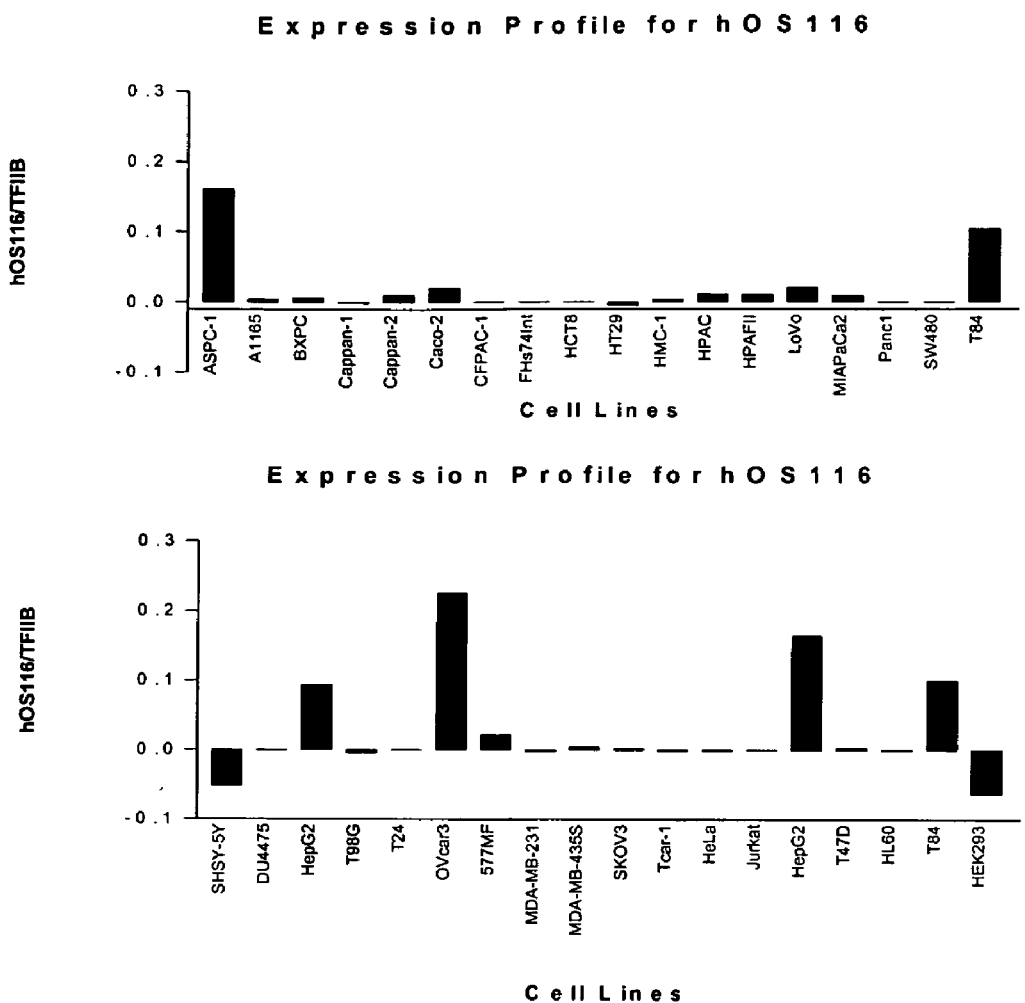
FIG. 8: OSGPR116 expression profile in human cell lines. Data is expressed as a ratio of TFIIB expression levels in the same cell lines, and the experiment was conducted as detailed in the Materials and Methods section.

This invention relates to the identification of fatty acid or lipid amides, such as a fatty acid alkanolamides, including fatty acid ethanolamides, including oleoyl ethanolamide, palmitoyl ethanolamide, stearoyl ethanolamide, linoleoyl ethanolamide, linolenoyl ethanolamide and oleamide, or a functional analog or homolog of one of these compounds, as ligands of the G-protein coupled receptor OSGPR116, and is directed to in vitro methods for screening candidate drugs for their ability to modulate the activity of OSGPR116, and to methods of treating disease by administering to an individual a therapeutic amount of a modulator of OSGPR116.

The discovery that OSGPR116 is the physiological target protein of fatty acid or lipid amides known to decrease food intake, such as oleoyl ethanolamide, will allow for the identification and development of new drugs that also act via this protein, and for the identification of other targets in the OSGPR116 signal transduction pathway that can themselves be a target for new drugs. This invention is the first demonstration of a specific G-protein coupled receptor activated by oleoyl ethanolamide, palmitoylethanolamide, stearoyl ethanolamide, linoleoyl ethanolamide, linolenoyl ethanolamide or oleamide. It was previously known that certain fatty acid ethanolamides had the ability to modulate food intake in mammals. However, the physiological target protein of such ethanolamides was unknown until the discovery described herein of their ability to act as ligands for the activation of the GPCR protein OSGPR116. Without knowledge of the target protein for such compounds it is very difficult and expensive to develop more effective compounds with similar activity. The invention described herein provides a solution to this problem.

This invention thus facilitates the design of simple and relatively inexpensive screens to identify novel compounds that act via OSGPR116, and that modulate feeding and are potential anti-obesity agents. Although prior to this invention one could have tried to discover compounds that act similarly to the fatty acid ethanolamides that had been reported to modulate food intake (WO 02/080860; de Fonseca, F. R. et.al. (2001) Nature, 414:209–212), without having a molecular target, or even a cellular target, one would have to rely on observations made in whole animal experiments, and thus cost and ethical considerations would have restricted one to studying relatively small numbers of close analogs of these ethanolamides. Furthermore, the recognition that OSGPR116 is a potential target for anti-obesity drugs will lead to the identification of other proteins in the OSGPR116 signal transduction pathway that can themselves be targets for potential anti-obesity agents.

Prior to this invention, the utility of the OSGPR116 receptor was unknown. The discovery that fatty acid or lipid amides, including oleoyl ethanolamide, palmitoyl ethanolamide, stearoyl ethanolamide, linoleoyl ethanolamide, linolenoyl ethanolamide and oleamide, can act as ligands indicates that diseases or conditions mediated by OSGPR116 include those affected by feeding behavior, such as obesity and eating disorders, and diseases associated with these conditions, including diabetes, dyslipidemia and cardiovascular disease associated with obesity, including atherosclerosis, arteriosclerosis, hypercholesteremia and hypertriglyceridemia, type 2 diabetes mellitus, type 1 diabetes, insulin resistance, hyperlipidemia, anorexia nervosa, bulimia, other feeding disorders, and cachexia associated with cancer, A/DS, inflammatory conditions and other conditions. By the term OSGPR116-mediated disease, it is meant those diseases or conditions where the modulation of OSGPR116 by agonists or antagonists results in a beneficial modification of the disease state or condition. Of the above conditions and diseases, antagonists, inverse agonists, partial inverse agonists and allosteric or allotropic antagonists should be useful for treating anorexia nervosa, bulimia, other feeding disorders resulting in weight loss, and cachexia associated with cancer, AIDS, inflammatory conditions and other conditions. Agonists, partial agonists and allosteric or allotopic agonists should be useful for treating the other conditions and diseases listed above, where a reduction of feeding, or an appetite suppressant effect, is required. Modulators of OSGPR116 that affect OSGPR116 oligomerization (e.g. homodimerization or heterodimerization) may also be useful for treating the conditions and diseases listed above.

In addition to the disorders mentioned above that are related to feeding behavior (i.e. obesity, diabetes etc), OSGPR116 expression in pancreatic and adipose tissues, and the colon and small intestine, as well as a variety of malignant and non-malignant cell lines (see below), suggests a potential involvement of OSGPR116 in immune system function, allergies, inflammatory bowel disease and related disorders, and cell proliferation, apoptosis, and cancer in tissues where it is expressed. Thus, modulation of OSGPR116 by agonists or antagonists may result in a beneficial modification of these disease states or conditions, or diseases or conditions associated abnormal regulation of the physiological processes listed.

OSGPR116 may therefore be used as a screening target for the identification and development of novel pharmaceutical agents for use in the methods of the invention. A modulator of OSGPR116 may be identified by contacting a cell expressing on its surface the receptor OSGPR116, said receptor being associated with a second component capable of providing a detectable signal in response to the binding of an agent to said receptor, with an agent to be screened under conditions to permit binding to the receptor; and determining whether the agent binds to, and activates, or inhibits, the receptor, by detecting the presence or absence of a signal generated from the interaction of the compound with the receptor and thereby determining whether the test agent modulates OSGPR116 activity. This may be carried out in the presence of a labeled or unlabeled ligand, e.g. a lipid amide or a fatty acid amide, such as a fatty acid alkanolamide, including fatty acid ethanolamides, and including, but not limited to, oleoyl ethanolamide, palmitoyl ethanolamide, stearoyl ethanolamide, linoleoyl ethanolamide, linolenoyl ethanolamide and oleamide, or a functional analog or homolog of one of these compounds.

An agent, or pharmaceutical agent, that can be tested for activity on the OSGPR116 receptor includes any chemical compound, including small molecules (<approx. 5000 Daltons molecular weight) and macromolecules (e.g. a polypeptide or protein, nucleic acid, glycoprotein, complex carbohydrate, synthetic or natural polymer etc.). Thus, an agent may be selected from combinatorial libraries, defined chemical entities, peptide and peptide mimetics, oligonucleotides and natural product libraries, and other entities such as display (e.g. phage display libraries) and antibody products. In one embodiment, the test agent is a fatty acid amide or lipid amide or a closely related compound. Thus an agent that modulates the activity of OSGPR116 can be any chemical compound that binds to and modulates the activity of OSGPR116.

This invention thus provides a method for identifying agents that modulate the activity of the OSGPR116 receptor, which comprises determining whether the agent interacts with OSGPR116 in a preparation comprising OSGPR116 receptor protein. The method may be carried out in combination with a ligand for OSGPR116, wherein the ligand is a lipid amide or a fatty acid amide, such as a fatty acid alkanolamide, including long chain fatty acid alkanolamides, and including fatty acid ethanolamides. In one embodiment, lipid amides are selected from oleoyl ethanolamide, palmitoyl ethanolamide, stearoyl ethanolamide, linoleoyl ethanolamide, linolenoyl ethanolamide and oleamide, or a functional analog or homolog of one of these compounds. In an alternative embodiment, the ligand can also be any of the compounds described in WO 02/080860 (e.g. compounds of formula I, Ia, II, III, IV, V, VI, or VII) as compounds for reducing body fat and modulating fatty acid metabolism.

Furthermore, in any of the methods, processes or screening assays described herein as embodiments of this invention for identifying compounds which bind to or are modulators of OSGPR116 activity, where a ligand or compound known to bind to or activate the OSGPR116 receptor is included in the method, process or assay (e.g. a competitive binding assay, or an assay for identifying antagonists), the ligand may be a lipid amide or a fatty acid amide, or any of the compounds described in WO 02/080860 as compounds for reducing body fat and modulating fatty acid metabolism (e.g. compounds of formula I, Ia, II, III, IV, V, VI, or VII as described in WO 02/080860, or any specific examples of these structures where the structure defines a genus).

Furthermore, in any of the methods, processes or screening assays described herein as embodiments of this invention for identifying compounds which bind to or are modulators of OSGPR116 activity, where a ligand or compound known to bind to or activate the OSGPR116 receptor is included in the method, process or assay, in one embodiment a ligand concentration is selected that produces a submaximal activation of OSGPR116 (e.g. 5%, 10%, 20%, or 50% of maximal response) in order to identify agonists, partial agonists or allosteric or allotopic agonists. Identification of allosteric or allotopic agonists will be dependent on the presence of such an activating ligand, and would not have been possible prior to the identification of fatty acid or lipid amides as ligands for OSGPR116 as described herein.

For example a method for identification of an agent that modulates OSGPR116 comprises (i) contacting a test agent with a cell (including but not limited to cells such as an adipocyte, a pancreatic, colon or small intestine cell, or other cells known to express OSGPR116) which expresses OSGPR116 or a variant thereof that is capable of coupling to a G-protein; and (ii) monitoring for OSGPR116 activity in the presence of a G protein; thereby determining whether the test agent modulates OSGPR116 activity.

The test agent may be contacted in step (i) with cells that express OSGPR116 or a variant thereof. Alternatively, the test agent may be contacted in step (i) with membranes obtained from such cells. In one embodiment, a modulator of OSGPR116 may be identified by determining the inhibition of binding of a ligand to cells which have the receptor on the surface thereof, or to cell membranes containing the receptor, in the presence of a candidate compound, under conditions to permit binding to the receptor, and determining the amount of ligand bound to the receptor, such that a compound capable of causing reduction of binding of a ligand is an agonist or antagonist, in which method the ligand is a lipid amide or a fatty acid amide, such as a fatty acid alkanolamide, including fatty acid ethanolamides. In one embodiment, lipid amides are selected from oleoyl ethanolamide, palmitoyl ethanolamide, stearoyl ethanolamide, linoleoyl ethanolamide, linolenoyl ethanolamide and oleamide, or a functional analog or homolog of one of these compounds.

This invention thus provides a method of identifying a modulator of OSGPR116 activity, comprising (a) providing a OSGPR116 receptor, (b) incubating the OSGPR116 receptor with an test agent to be screened under conditions to permit binding of the test agent to the receptor; and (c) determining whether the test agent binds to, and activates, or inhibits, the receptor, by detecting the presence or absence of a signal generated from the interaction of the agent with the receptor, and thereby determining whether the test agent modulates OSGPR116 activity.

This invention thus also provides a method of identifying a modulator of OSGPR116, comprising (a) providing a cell expressing on its surface the receptor OSGPR116, said receptor being associated with a second component capable of providing a detectable signal in response to the binding of an agent to said receptor, (b) contacting with an test agent to be screened under conditions to permit binding to the receptor; and (c) determining whether the agent binds to, and activates, or inhibits, the receptor, by detecting the presence or absence of a signal generated from the interaction of the compound with the receptor and thereby determining whether the test agent modulates OSGPR116 activity.

This invention further provides the above methods wherein the step of incubating or contacting with the test agent (step b) is carried out in combination with (i.e. in the presence of; or by also contacting the cells with) a ligand for the OSGPR116 receptor, in which method the ligand is a lipid amide or a fatty acid amide, such as a fatty acid alkanolamide, including fatty acid ethanolamides. In one embodiment, lipid amides are selected from oleoyl ethanolamide, palmitoyl ethanolamide, stearoyl ethanolamide, linoleoyl ethanolamide, linolenoyl ethanolamide and oleamide, or a functional analog or homolog of one of these compounds.

In the practice of this invention the OSGPR116 receptor can be from any species, or a functional variant thereof, as described herein. In one embodiment, the OSGPR116 receptor is selected from human, mammalian, rodent, murine, rat, rabbit and monkey receptors. The cells of this invention can be any cells expressing OSGPR116 receptor or a functional variant thereof. Suitable cells are adipocytes or pancreatic cells, or cells where the OSGPR116 receptor expressed by the cell is a recombinant receptor.

Adipocytes can be provided as a differentiated cell line, or can be primary adipocytes harvested from a human or animal donor. In the methods of this invention, where the OSGPR116 is associated with a second component capable of providing a detectable signal, that second component may be a G-protein, for example a Gi or a Go-protein, or a G-protein with a promiscuous G-alpha subunit (e.g. G-alpha$_{16}$, G-alpha$_{15}$). In an alternative embodiment that second component may be a Gs, Gq or G$_{12-13}$ protein. In a further embodiment the second component can be β-arrestin.

The invention also provides a test kit suitable for identification of an agent that modulates OSGPR116 activity, which kit comprises (a) OSGPR116 or a variant thereof which is capable of coupling to a G-protein; and (b) means for monitoring OSGPR116 activity. The G-protein may be selected from Gi, Go, G-alpha$_{16}$, G-alpha$_{15}$, Gs, Gq and G$_{12-13}$, or any other G-protein that is activated by OSGPR116 under the conditions employed in the test kit.

This invention also provides a method for identification of an agent that modulates a cellular activity regulated by activation of OSGPR116 in a cell (e.g. insulin secretion, ion flux across cell membranes, lipid metabolism, storage or transport, glucose metabolism or transport, etc.), which method comprises contacting a test cell with a test agent that modulates OSGPR116 activity, and which has been identified by the method of the invention, monitoring a change in the cellular activity, and thereby determining whether the test substance is a modulator of the cellular activity. This method can also be performed where the step of contacting a test cell with a test agent is carried out in combination with a ligand for the OSGPR116 receptor. The invention further provides this method but wherein the test agent is not known to modulate OSGPR activity, and wherein the step of contacting a test cell with a test agent is carried out in combination with a ligand for the OSGPR116 receptor. In these methods the ligand is a lipid amide or a fatty acid amide, such as a fatty acid alkanolamide, including fatty acid ethanolamides. In one embodiment, lipid amides are selected from oleoyl ethanolamide, palmitoyl ethanolamide, stearoyl ethanolamide, linoleoyl ethanolamide, linolenoyl ethanolamide and oleamide, or a functional analog or homolog of one of these compounds. Competition of the test agent with the ligand will identify agents (e.g. antagonists, reverse agonists) that can modulate regulation of the cellular activity by the ligand.

This invention also provides a method for identification of an agent that inhibits feeding, which method comprises contacting a test subject with a test agent which modulates OSGPR116 activity, and which has been identified by the method of the invention, and monitoring feeding behavior, thereby determining whether the test substance is an inhibitor of feeding.

This invention also provides a method for identification of an agent that stimulates feeding, which method comprises contacting a test subject with a test agent which modulates OSGPR116 activity, and which has been identified by the method of the invention, and monitoring feeding behavior, thereby determining whether the test substance is a stimulator of feeding.

This invention also provides a modulator of OSGPR116 activity, or a modulator of feeding, identified by a method of the invention, and their use in therapy and pharmaceutical compositions comprising them.

This invention also provides a method of reducing food intake in a mammal in recognized need of such treatment, said method comprising administering to said mammal in recognized need of such treatment, a fatty acid amide selected from stearoyl ethanolamide, linoleoyl ethanolamide, linolenoyl ethanolamide and oleamide, or a functional analog or homolog of one of these compounds, wherein said administering is in an effective amount to reduce food intake in said mammal.

This invention also provides a method of treating obesity in a mammal in recognized need of such treatment, said method comprising administering to said mammal in recognized need of such treatment, a fatty acid amide selected from stearoyl ethanolamide, linoleoyl ethanolamide, linolenoyl ethanolamide and oleamide, or a functional analog or homolog of one of these compounds, wherein said administering is in an effective amount to reduce obesity in said mammal.

This invention also provides a modulator of OSGPR116 activity, or a modulator of feeding, identified by a method of the invention, or a polynucleotide which encodes OSGPR116 or a variant polypeptide, for use in a method of treatment of the human or animal body by therapy; and use of such a modulator (e.g. activator, inhibitor) or polynucleotide in the manufacture of a medicament for the treatment of diseases or conditions modulated by OSGPR116, for example, feeding behavior, such as obesity and eating disorders, and diseases associated with these conditions, including diabetes, dyslipidemia and cardiovascular disease associated with obesity, including atherosclerosis, arteriosclerosis, hypercholesteremia and hypertriglyceridemia, type II diabetes mellitus, type I diabetes, insulin resistance, hyperlipidemia, anorexia nervosa, bulimia, other feeding disorders, and cachexia associated with cancer, AIDS, inflammatory conditions and other conditions.

This invention further provides the use of a modulator of OSGPR116 for the manufacture of a medicament for the treatment of OSGPR116 mediated diseases, with the proviso that the modulator is not oleoylethanolamide, palmitoylethanolamide or elaidoylethanolamide when the disease is treated by suppression of food intake.

The invention also provides a method of treating OSGPR116 mediated disease in an individual which comprises administering to the individual a therapeutic amount of a modulator of OSGPR116 activity, with the proviso the modulator of OSGPR116 activity is not oleoylethanolamide, palmitoylethanolamide or elaidoylethanolamide when the disease is treated by suppression of food intake.

Figure 11:
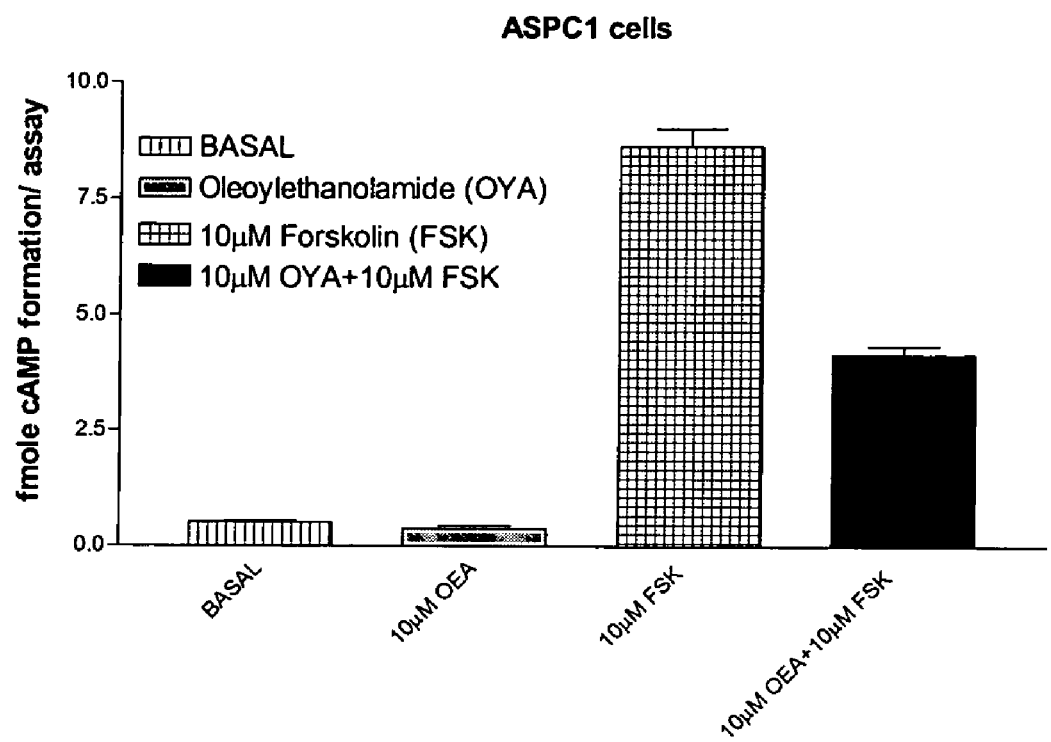
FIG. 11: Effect of oleoylethanolamide on forskolin-stimulated cAMP levels in ASPC-1 cells. Briefly, ASPC-1 cells were incubated with oleoylethanolamide (10 uM), forskolin (10 μM) or a combination of forskolin (10 μM) and oleoylethanolamide (10 μM) and the cAMP accumulation in the cells determined as detailed in the Materials and Methods.

The present invention relates to the use of the human G-protein coupled receptor OSGPR116, and variants thereof. Human, rat and mouse OSGPR116 have been cloned previously (see U.S. Pat. No. 6,221,660, U.S. Pat. No. 6,468,756, WO 00/50562). Human OSGPR116 receptor encoding DNA has the GenBank Accession number AR240216. The term OSGPR116 as used herein incorporates variants of OSGPR116. OSGPR116 receptors for use in the screening methods of the invention include all species orthologues, e.g., may be rodent, mouse, rat, rabbit, dog, monkey or human. Human and mouse nucleic acid and amino acid sequences are depicted in FIGS. 1–4 (SEQ ID NOS:1–4). Human OSGPR116 is preferred. The term "variant" refers to a polypeptide which has the same essential character or basic biological functionality as OSGPR116. The essential character of OSGPR116 can be defined as that of a G-protein coupled receptor that is activated by fatty acid or lipid amides as described herein. Thus, the term "variant" refers in particular to a GPCR polypeptide which activates Gi/o in response to fatty acid or lipid amides under the experimental conditions described herein (e.g. see FIG. 11).

To determine whether a candidate variant has the same function as OSGPR116, the ability of the variant to activate Gi/o-protein can be determined. The effect of the candidate variant on Gi/o activation can be monitored. This can be carried out, for example, by contacting cells expressing the candidate variant with a ligand which activates Gi/o-protein when contacted with cells that express OSGPR116, and measuring a Gi/o-coupled readout. A control experiment is typically also carried out in which cells of the same type as those expressing the candidate variant, but expressing OSGPR116 instead, are contacted with the ligand and a corresponding Gi/o-coupled readout is measured. The effect attained by the candidate variant can then be directly compared with that attained by OSGPR116. It should be noted that, although OSGPR116 activates Gi/o-protein under the experimental conditions employed herein (e.g. see FIG. 11), under different experimental conditions OSGPR116 may activate other G-proteins. Thus, when different experimental conditions are employed the G-protein activated by OSGPR116 may have to be re-determined prior to comparison with a candidate variant.

Alternatively, a variant polypeptide is one which binds to the same ligand as OSGPR116. That can be determined directly by contacting a candidate variant with a radiolabelled ligand that binds to OSGPR116 and monitoring binding of the ligand to the variant. Typically, the radiolabelled ligand can be incubated with cell membranes containing the candidate variant. The membranes can then be separated from non-bound ligand and dissolved in scintillation fluid to allow the radioactivity of the membranes to be determined by scintillation counting. Non-specific binding of the candidate variant may also be determined by repeating the experiment in the presence of a saturating concentration of non-radioactive ligand. Preferably a binding curve is constructed by repeating the experiment with various concentrations of the candidate variant. The ability of OSGPR116 to bind a ligand may also be determined indirectly as described below. Surface plasmon resonance methodology can also be utilized, with the advantage that radiolabelling is not required (e.g. see technology reviews at published by Biacore, in print and on their website; Myszka, D. G. and Rich, R. L. (2000) Pharmaceutical Science and Technology Today, 3:310–317; Quinn, J. G. et. al. (2000) Anal. Biochem. 281:135–143; Williams, C. (2000) Current Opinion Biotech. 11:42–46). Additional methods of determining and characterizing ligand binding are well known in the art (e.g. see Kenakin, T. (1997) Molecular Pharmacology, A Short Course. p. 1–235, Blackwell Science).

Typically, polypeptides with more than about 65% identity, preferably at least 80% or at least 90% and particularly preferably at least 95%, at least 97% or at least 99% identity, with the amino acid sequences of human, rat or mouse OSGPR116 as described in U.S. Pat. No. 6,221,660, and U.S. Pat. No. 6,468,756, or more preferably over a region of at least 20, preferably at least 30, at least 40, at least 60 or at least 100 contiguous amino acids or over the full length of the amino acid sequences are considered as OSGPR116 variants. The UWGCG Package provides the BESTFIT program which can be used to calculate identity (for example used on its default settings) (Devereau et al (1984) Nucleic Acid Research 12, p 387–395). The PILEUP and BLAST algorithms can be used to calculate identity or line up sequences (typically on their default settings), for example as described in Altschul S. F. (1993) J. Mol. Evol. 36: 290–300 and Altschul, S. F. et. al. (1990) J. Mol. Biol. 215:403. Software for performing BLAST analyses is publicly available through the National Center for Biotechnology Information (e.g. via their website).

Variant polypeptides therefore include naturally occurring allelic variants. An allelic variant will generally be of human or non-human mammal origin, such as bovine or porcine origin. Alternatively, a variant polypeptide can be a non-naturally occurring sequence. A non-naturally occurring variant may thus be a modified version of OSGPR116.

The amino acid sequence of OSGPR116 may be modified by deletion and/or substitution and/or addition of single amino acids or groups of amino acids as long as the modified polypeptide retains the capability to function as a G-protein coupled receptor. Such amino acid changes may occur in one, two or more of the intracellular domains of OSGPR116 and/or one, two or more of the extracellular domains of OSGPR116 and/or one, two or more of the transmembrane domains of OSGPR116.

Amino acid substitutions may thus be made, for example from 1, 2, 3, 4 or 5 to 10, 20 or 30 substitutions. Conservative substitutions may be made, for example according to the following Table. Amino acids in the same block in the second column and preferably in the same line in the third column may be substituted for each other.

| ALIPHATIC | Non-polar | G A P |
|           |           | I L V |
|           | Polar-uncharged | C S T M |
|           |           | N Q |
|           | Polar-charged | D E |
|           |           | K R |
| AROMATIC  |           | H F W Y |

A variant polypeptide may be a shorter polypeptide. For example, a polypeptide of at least 20 amino acids or up to 50, 60, 70, 80, 100, 150, 200, 250, or 300 amino acids in length may constitute a variant polypeptide as long as it demonstrates the functionality of OSGPR116. A variant polypeptide may therefore lack one, two or more intracellular domains and/or one, two or more extracellular domains and/or one, two or more transmembrane domains. A variant polypeptide may thus be a fragment of the full length polypeptide. A shortened polypeptide may comprise a ligand-binding region (N-termninal extracellular domain) and/or an effector binding region (C-terminal intracellular domain). Such fragments can be used to construct chimeric receptors, preferably with another 7-transmembrane G-protein coupled receptor.

Variant polypeptides include polypeptides that are chemically modified, e.g. post-translationally modified. For example, such variant polypeptides may be glycosylated or comprise modified amino acid residues, e.g. phospho-amino acids. They may also be modified by the addition of histidine residues, for example 6 or 8 His residues, or an epitope tag, for example a T7, HA, myc or flag tag, to assist their purification or detection. They may be modified by the addition of a signal sequence to promote insertion into the cell membrane.

The invention also utilizes nucleotide sequences that encode OSGPR116 or variants thereof as well as nucleotide sequences which are complementary thereto. The nucleotide sequence may be RNA or DNA, including genomic DNA, synthetic DNA or cDNA. Preferably the nucleotide sequence is a DNA sequence, and most preferably, a cDNA sequence. Such nucleotides can be isolated from human cells or synthesized according to methods well known in the art, as described by way of example in Sambrook et. al., Molecular Cloning: A Laboratory Manual, $2^{nd}$ edition, Cold Spring Harbour Laboratory Press, 1989. Typically a useful polynucleotide comprises a contiguous sequence of nucleotides which is capable of hybridizing under selective conditions to the coding sequence or the complement of the coding sequences of OSGPR116.

A polynucleotide can hydrize to the coding sequence or the complement of the coding sequences of OSGPR116 at a level significantly above background. Background hybridization may occur, for example, because of other cDNAs present in a cDNA library. The signal level generated by the interaction between a polynucleotide and the coding sequence or complement of the coding sequence of OSGPR116 is typically at least 10 fold, preferably at least 100 fold, as intense as interactions between other polynucleotides and the coding sequence of OSGPR116. The intensity of interaction may be measured, for example, by radiolabelling the probe, e.g. with $^{32}P$. Selective hybridization may typically be achieved using conditions of low stringency (0.3 M sodium chloride and 0.03 M sodium citrate at about 40° C., medium stringency (for example, 0.3M sodium chloride and 0.03M sodium citrate at about 50° C., or high stringency (for example, 0.03M sodium chloride and 0.003M sodium citrate at about 60° C.

The coding sequences of OSGPR116 may be modified by one or more nucleotide substitutions, for example from 1, 2, 3, 4 or 5 to 10, 25, 50 or 100 substitutions. The polynucleotides of OSGPR116 may alternatively or additionally be modified by one or more insertions and/or deletions and/or by an extension at either or both ends. The modified polynucleotides generally encode polypeptides which have G-protein coupled receptor activity or inhibit the activity of OSGPR116. Degenerate substitutions may be made and/or substitutions may be made which would result in a conservative amino acid substitution when the modified sequences are translated, for example as shown in the Table above.

A nucleotide sequence which is capable of selectively hybridizing to the complement of the DNA coding sequences of OSGPR116 will generally have at least 60%, at least 70%, at least 80%, at least 90%, at least 95%, at least 98% or at least 99% sequence identity to the coding sequence of OSGPR116 over a region of at least 20, preferably at least 30, for instance at least 40, at least 60, more preferably at least 100, 300, 600, 900 contiguous nucleotides, or most preferably over the full length. Methods of measuring nucleic acid and protein homology are well known in the art. For example the UWGCG Package provides the BESTFIT program which can be used to calculate homology (Devereux J, et.al. (1984) Nucleic Acids Res 12:387–395). Similarly the PILEUP and BLAST algorithms can be used to line up sequences (for example, as described in Altschul, S. F. et.al. (1990) J. Mol. Biol. 215:403–410; Altschul, S. F., et. al. (1997) Nucleic Acids Res. 25:3389–3402). Many different settings are possible for such programs. In accordance with the invention, the default settings may be used.

Any combination of the above mentioned degrees of sequence identity and minimum sizes may be used to define polynucleotides of the invention, with the more stringent combinations (i.e. higher sequence identity over longer lengths) being preferred.

Thus, for example a polynucleotide which has at least 90% sequence identity over 25, preferably over 30 nucleotides forms one aspect of the invention, as does a polynucleotide which has at least 95% sequence identity over 40 nucleotides.

Polynucleotides may be used as a primer, e.g. a PCR primer or a primer for an alternative amplification reaction of a probe, e.g. labelled with a revealing label by conventional means for identifying mutations in OSGPR116 that may be implicated in diseases resulting from abnormal control of feeding behavior. Fragments of polynucleotides may be fused to the coding sequence of other proteins, preferably other G-protein coupled receptors, to form a sequence coding for a fusion protein.

Such primers, probes and other fragments will preferably be at least 10, preferably at least 15 or at least 20, for example at least 25, at least 30 or at least 40 nucleotides in length. They will typically be up to 40, 50, 60, 70, 100 or 150 nucleotides in length. Probes and fragments can be longer than 150 nucleotides in length, for example up to 200, 300, 400, 500 nucleotides in length, or even up to a few nucleotides, such as five or ten nucleotides, short of the coding sequences of OSGPR116.

The polynucleotides have utility in production of OSGPR116 or variant polypeptides, which may take place in vitro, in vivo or ex vivo. The polynucleotides may be used as therapeutic agents in their own right, in gene therapy techniques. The polynucleotides are cloned into expression vectors for these purposes. Such expression vectors are routinely constructed in the art of molecular biology and may for example involve the use of plasmid DNA and appropriate initiators, promoters, enhancers and other elements, such as for example polyadenylation signals which may be necessary, and which are positioned in the correct orientation, in order to allow for protein expression. Other suitable vectors would be apparent to a person skilled in the art. By way of further example in this regard, Molecular Cloning: a Laboratory Manual, 2001, $3^{rd}$ Edition, by Joseph Sambrook and Peter MacCallum (the former Maniatis Cloning manual) provides a good source.

Expression vectors comprise a polynucleotide encoding the desired polypeptide operably linked to a control sequence which is capable of providing for the expression of the coding sequence by a host cell. The term "operably linked" refers to a juxtaposition wherein the components described are in a relationship permitting them to function in their intended manner. A regulatory sequence, such as a promoter, "operably linked" to a coding sequence is positioned in such a way that expression of the coding sequence is achieved under conditions compatible with the regulatory sequence. Thus nucleic acid of this invention is operably linked when it is placed into a functional relationship with another nucleic acid sequence. For example, DNA for a presequence or secretory leader is operably linked to DNA for a polypeptide if it is expressed as a preprotein which participates in the secretion of the polypeptide; a promoter or enhancer is operably linked to a coding sequence if it affects the transcription of the sequence; or a ribosome binding site is operably linked to a coding sequence if it is positioned so as to facilitate translation. Generally, operably linked means that the DNA sequences being linked are contiguous and, in the case of a secretory leader, contiguous and in reading frame.

The vectors may be plasmid, virus or phage vectors provided with an origin of replication, optionally a promoter for the expression of the said polynucleotide, and optionally a regulator of the promoter. The vectors may contain one or more selectable marker genes, for example an ampicillin resistance gene in the case of a bacterial plasmid or a resistance gene for a fungal vector. Vectors may be used in vitro, for example for the production of RNA or DNA or used to transfect or transform a host cell, for example, a mammalian host cell. The vectors may also be adapted to be used in vivo, for example in a method of gene therapy.

This invention provides vectors comprising any nucleic acids encoding the OSGPR116 receptors of this invention, including vectors adapted for expression in a cell, which vector comprises the regulatory elements necessary for expression of the nucleic acid in the cell operatively linked to the nucleic acid encoding the receptor so as to permit expression thereof. Furthermore this invention also provides vectors which are plasmids.

This invention further provides host cells comprising any of the vectors described herein. The host cell is typically a eukaryotic cell, a mammalian cell, a human cell, an insect cell, a yeast cell or a prokaryotic cell, although is not limited to these. In one embodiment of this invention ASPC-1 cells are used. In another HEK-293 cells are used.

Recombinant methods for synthesis of the OSGPR116 receptors of this invention commence with the construction of a replicable vector containing nucleic acid that encodes the OSGPR116 receptor. Vectors typically perform two functions in collaboration with compatible host cells. One function is to facilitate the cloning of the nucleic acid that encodes the OSGPR116 receptor, i.e., to produce usable quantities of the nucleic acid. The other function is to direct the expression of the OSGPR116 receptor. One or both of these functions are performed by the vector-host system. The vectors will contain different components depending upon the function they are to perform as well as the host cell that is selected.

This invention thus provides vectors that contain nucleic acid encoding the OSGPR116 receptor. Typically, this will be DNA that encodes the OSGPR116 receptor in its mature form linked at its amino terminus to a secretion signal. This secretion signal preferably is the signal presequence that normally directs the insertion of the wild-type OSGPR116 receptor through the plasma membrane. However, suitable secretion signals also include signals from other receptors or from secreted polypeptides of the same or related species.

In instances where the expression of OSGPR116 would exert an undesired biological effect on the host cell if induced to accumulate in high concentration in the cell membrane during the growth phase, this potential problem may be overcome by placing the nucleic acid encoding the OSGPR116 receptor under the control of an inducible promoter.

In the practice of this invention, for cloning vectors the OSGPR116 receptor-encoding nucleic acid ordinarily is present together with a nucleic acid sequence that enables the vector to replicate in a selected host cell independent of the host chromosomes. This sequence is generally an origin of replication or an autonomously replicating sequence. Such sequences are well-known for a variety of bacteria, yeast and higher eukaryotic cells. The origin from the well-known plasmid pBR322 is suitable for *E. coli* bacteria, the 2µ plasmid origin for yeast and various viral origins for mammalian cells (SV40, polyoma, adenovirus or bovine papilloma virus). Less desirably, DNA is cloned by insertion into the genome of a host. This is readily accomplished with *bacillus* species, for example, by inserting into the vector DNA that is complementary to *bacillus* genomic DNA. Transfection of *bacillus* with this vector results in homologous recombination with the genome and insertion of the OSGPR116 receptor DNA. However, the recovery of genomic DNA encoding the OSGPR116 receptor is more complex than obtaining exogenously replicated viral or plasmid DNA because restriction enzyme digestion is required to recover the OSGPR116 receptor DNA from the genome of the cloning vehicle.

In the practice of this invention, expression and cloning vectors should contain a selection gene, also termed a selectable marker. This is a gene that encodes a protein necessary for the survival or growth of a host cell transformed with the vector. The presence of this gene ensures the growth of only those host cells that express the inserts. Typical selection genes encode proteins that (a) confer resistance to antibiotics or other toxins, e.g. ampicillin, neomycin, blasticidin, G-418, mycophenolic acid, hygromycin B, bleomycin, phleomycin, methotrexate or tetracycline, (b) complement auxotrophic deficiences, or (c) supply critical nutrients not available from complex media, e.g. the gene encoding D-alanine racemase for bacilli.

A suitable selection gene for use in yeast is the trp1 gene present in the yeast plasmid YRp7 (Stinchcomb et al., 1979, "Nature", 282: 39; Kingsman et al., 1979, "Gene", 7: 141; or Tschemper et al., 1980, "Gene", 10: 157). The trp1 gene provides a selection marker for a mutant strain of yeast lacking the ability to grow in the absence of tryptophan, for example ATCC No. 44076 or PEP41 (Jones, 1977, "Genetics", 85: 12). The presence of the trp1 lesion in the yeast host cell genome then provides an effective environment for detecting transformation by growth in the absence of tryptophan. Similarly, Leu2 deficient yeast strains (ATCC 20,622 or 38,626) are complemented by known plasmids bearing the Leu2 gene.

Examples of suitable selectable markers for mammalian cells are dihydrofolate reductase (DHFR), thymidine kinase or proteins for neomycin resistance. Such markers enable the identification of cells that were competent to take up the OSGPR116 receptor nucleic acid. The mammalian cell transformants are placed under selection pressure, which only the transformants are uniquely adapted to survive by virtue of having taken up the marker. Selection pressure is imposed by culturing the transformants in successive rounds of cell culture, in which the concentration of selection agent in the medium is successively increased, thereby leading to amplification of both the selection gene and the DNA encoding the OSGPR116 receptor. Increased quantities of OSGPR116 receptor are synthesized from the amplified DNA.

For example, selection for DHFR transformed cells is conducted in a culture medium which lacks hypoxanthine, glycine, and thymidine. An appropriate host cell in this case is the Chinese hamster ovary (CHO) cell line deficient in DHFR activity, prepared and propagated as described by Urlaub and Chasin, 1980, "Proc. Nat'l. Acad, Sci. USA" 77: 4216.

A particularly useful DHFR is a mutant DHFR that is highly resistant to methotrexate (MTX) (EP 117,060A). This selection agent can be used with any otherwise suitable host, notwithstanding the presence of endogenous DHFR. One simply includes sufficient MTX in the medium to inactivate all of the endogenous DHFR, whereupon MTX selection becomes solely a function of amplification of the mutant DHFR DNA. Most eukaryotic cells which are capable of adsorbing MTX appear to be methotrexate sensitive. One such useful cell line is a CHO line, CHO-K1 (ATCC No. CCL 61).

Other methods, vectors and host cells suitable for adaptation to the synthesis of the OSGPR116 receptor of this invention in recombinant vertebrate cell culture are described in M. J. Gething et al., Nature 293: 620–625 (1981); N. Mantei et al., Nature 281: 40–46; EP 117,060A; EP 117,058A; Molecular Cloning: a Laboratory Manual, 2001, $3^{rd}$ Edition, by Joseph Sambrook and Peter MacCallum, (the former Maniatis Cloning manual) (e.g. ISBN 0-87969-577-3); and Current Protocols in Molecular Biology, Ed. Fred M. Ausubel, et. al. John Wiley & Sons (e.g. ISBN 0-471-50338-X).

Expression vectors of this invention, unlike cloning vectors, should contain a promoter and/or other sequence that is recognized by the host organism for strong transcription of the OSGPR116 receptor encoding DNA. This is generally a promoter homologous to the intended host. In the case of vectors for higher eukaryotes, enhancer sequences are useful for further increasing transcription from promoters. Unlike promoters, enhancers do not need to be located 5' to the OSGPR116 receptor encoding nucleic acid. Commonly used promoters for prokaryotes include the beta-lactamase and lactose promoter systems (Chang et al., 1978, "Nature", 275: 615; and Goeddel et al., 1979, "Nature", 281; 544), alkaline phosphatase, a tryptophan (trp) promoter system (Goeddel 1980, "Nucleic Acids Res." 8: 4057 and EPO Appln. Publ. No. 36,776) and hybrid promoters such as the tac promoter (H. de Boer et al., 1983, "Proc. Nat'l. Acad. Sci. USA" 80: 21–25). However, other known microbial promoters are suitable. Their nucleotide sequences have been published, thereby enabling a skilled worker operably to ligate them to DNA encoding the OSGPR116 receptor in plasmid vectors (Siebenlist et al., 1980, "Cell" 20: 269) using linkers or adaptors to supply any required restriction sites. Promoters for use in prokaryotic systems also will contain a Shine-Dalgamo (S.D.) sequence operably linked to the DNA encoding the OSGPR116 receptor.

Suitable promoting sequences in yeast vectors for use in the practice of this invention include *S. cerevisiae* GAL4 and ADH promoters, and *S. pombe* nmt1 and adh promoters, and further include the promoters for metallothionein, 3-phosphoglycerate kinase (-Hitzeman et al., 1980, "J. Biol. Chem.", 255: 2073) or other glycolytic enzymes (Hess et al., 1968, "J. Adv. Enzyme Reg.", 7: 149; and Holland, 1978, "Biochemistry", 17: 4900), such as enolase, glyceraldehyde-3-phosphate dehydrogenase, hexokinase, pyruvate decarboxylase, phosphofructokinase, glucose-6-phosphate isomerase, 3-phosphoglycerate mutase, pyruvate kinase, triosephosphate isomerase, phosphoglucose isomerase, and glucokinase.

Other yeast promoters for use in the practice of this invention, which have the additional advantage of transcription controlled by growth conditions, are the promoter regions for alcohol dehydrogenase 2, isocytochrome C, acid phosphatase, degradative enzymes associated with nitrogen metabolism, and the aforementioned metallothionein and glyceralidehyde-3-phosphate dehydrogenase, as well as enzymes responsible for maltose and galactose utilization. Suitable vectors and promoters for use in yeast expression are further described in R. Hitzeman et al., EP 73,657A.

In the practice of this invention, transcription from vectors in mammalian host cells is controlled by promoters and/or enhancers obtained from the genomes of bovine papilloma virus, vaccinia virus, polyoma virus, adenovirus 2, retroviruses, hepatitus-B virus, cytomegalovirus (e.g. IE promoter), spleen focus forming virus, murine stem cell virus, Moloney murine leukemia virus (e.g. MMLV LTR), Simian Virus 40 (SV40), HSV (such as the HSV IE promoters), or HPV (particularly the HPV upstream regulatory region (URR)), operably linked to the OSGPR116 receptor nucleic acid. The early and late promoters of the SV40 virus are as conveniently obtained as an SV40 restriction fragment, which also contains the SV40 viral origin of replication (Fiers et al., 1978, "Nature", 273: 113). Mammalian promoters also include the metallothionein promoter, which can be induced in response to heavy metals such as cadmium. Of course, promoters or enhancers from the host cell or related species also are useful herein. Mammalian promoters, such as P-actin promoters, may be used. Tissue specific promoters, for example adipose or pancreatic cell specific promoters, may also be used. A suitable mammalian expression vector for practice of this invention is pcDNA3.1. Retrovirus vectors may also be used in the practice of this invention (e.g. rous sarcoma virus (RSV) LTR promoter), including those with inducible elements, e.g. tetracycline responsive elements.

The vector may further include sequences flanking the polynucleotide which comprise sequences homologous to eukaryotic genomic sequences, preferably mammalian genomic sequences, or viral genomic sequences. This will allow the introduction of the relevant polynucleotides into the genome of eukaryotic cells or viruses by homologous recombination. In particular, a plasmid vector comprising the expression cassette flanked by viral sequences can be used to prepare a viral vector suitable for delivering the polynucleotides of the invention to a mammalian cell. Retrovirus vectors for example may be used to stably integrate the polynucleotide into the host genome. Replication-defective adenovirus vectors by contrast remain episomal and therefore allow transient expression.

Expression vectors used in eukaryotic host cells of this invention (yeast, fungi, insect, plant, animal or human) will also contain sequences necessary for the termination of transcription and for stabilizing the mRNA. Such sequences are commonly available from the 3'-untranslated regions of eukaryotic or viral cDNAs. These regions contain regions that are transcribed as polyadenylated segments in the untranslated portion of the mRNA encoding the OSGPR116 receptor. The 3' untranslated regions also include transcription termination sites.

Cells are transformed or transfected with the vectors to express the OSGPR116 polypeptide or variants thereof. Such cells may be eucaryotic or prokaryotic. They include transient or, preferably, stable higher eukaryotic cell lines such as mammalian cells or insect cells, lower eukaryotic cells such as yeast, and prokaryotic cells such as bacterial cells. Particular examples of cells which may be used to express OSGPR116 or a variant polypeptide include mammalian HEK293T, CHO, HeLa, ASPC-1 and COS7 cells. Preferably the cell line selected will be one which is not only stable, but also allows for mature glycosylation and cell surface expression of OSGPR116 polypeptide or a variant. Cells such as adipose or pancreatic cells expressing OSGPR116 receptors or a variant polypeptide may be used in screening assays. Expression may be achieved in transformed oocytes. The OSGPR116 polypeptides or a variant may be expressed in cells such as those of adipose or pancreatic tissue of a transgenic non-human animal, preferably a rodent such as a mouse.

Suitable host cells for cloning or expressing the vectors herein are prokaryotes, yeast or higher eukaryotic cells. Prokaryotes include gram negative or gram positive organisms, for example *E. coli* or bacilli. A preferred cloning host is *E. coli* 294 (ATCC 31,446) although other gram negative or gram positive prokaryotes such as *E. coli* B, *E. coli* X1776 (ATCC 31,537), *E. coli* W3110 (ATCC 27,325), pseudomonas species, or *Serratia Marcesans* are suitable.

In addition to prokaryotes, eukaryotic microbes such as filamentous fungi or yeast are suitable hosts for the OSGPR116 receptor encoding vectors. *Saccharomyces cerevisiae*, or common baker's yeast, is the most commonly used among lower eukaryotic host microorganisms. However, a number of other genera, species and strains are commonly available and useful herein.

The preferred host cells for the expression of functional OSGPR116 receptors of this invention are cultures of cells derived from multicellular organisms. OSGPR116 receptors or variants thereof may contain hydrophobic regions that are incompatible with lower microorganisms, require complex processing to properly form disulfide bonds or require subunit processing. In addition, it may be desirable to glycosylate the receptor in a fashion similar to the native receptor. All of these functions can be best performed by higher eukaryotic cells. In principle, any higher eukaryotic cell culture is workable, whether from vertebrate or invertebrate culture, although cells from mammals such as humans are preferred. Propagation of such cells in culture is per se well known. See Tissue Culture, Academic Press, Kruse and Patterson, editors (1973), or Culture of Animal Cells: A Manual of Basic Technique, 4th Ed. Author, R. Ian Freshney, John Wiley & Sons., (2000). Examples of useful mammalian host cell lines are VERO and HeLa cells, human 239 cells, quail QT6 cells, NIH-3T3 cells, Chinese hamster ovary cell lines, and W138, BHK, COS-7, HEK293, ASPC-1 and MDCK cell lines.

Thus, this invention also provides a cell comprising a OSGPR116 receptor. The cell of this invention can be eukaryotic, mammalian, human, insect or yeast. The cell comprising the OSGPR116 receptor of this invention can be a stable or transient transfectant.

In embodiments of this invention where purification of the OSGPR116 receptor is required, for example from a detergent solubilized membrane preparation containing the OSGPR116 receptor, the OSGPR116 receptor is readily purified by any of the protein purification techniques commonly practiced in the art, e.g. immunoaffinity chromatography. The recombinant OSGPR116 receptor can also be engineered to contain a structural element or epitope to assist in its purification, e.g. poly-histidine, calmodulin-binding peptide, glutathione-S-transferase, or maltose-binding protein.

The present invention is concerned in particular with the use of OSGPR116 or a functional variant in screening methods to identify agents that may act as modulators of OSGPR116 receptor activity and, in particular, agents that may act as modulators of feeding. Such modulators are useful in the treatment of diseases or conditions affected by feeding behavior, such as obesity and eating disorders, and diseases associated with these conditions, including diabetes, dyslipidemia and cardiovascular disease associated with obesity, including atherosclerosis, arteriosclerosis, hypercholesteremia and hypertriglyceridemia, type II diabetes mellitus, type I diabetes, insulin resistance, hyperlipidemia, anorexia nervosa, bulimia, other feeding disorders, and cachexia associated with cancer, AIDS, inflammatory conditions and other conditions. By the term OSGPR116-mediated disease, it is meant those diseases or conditions where the modulation of OSGPR116 by agonists or antagonists results in a beneficial modification of the disease state or condition.

Any suitable form of assay may be employed to identify a modulator of OSGPR116 activity and/or of feeding. In general terms, such screening methods involve contacting OSGPR116 or a variant polypeptide with a test compound and then determining receptor activity. G-protein activation, for example Gi/o-protein activation, may be determined therefore. Where a test compound affects receptor activity, its effect on feeding can be determined by contacting a subject with the test compound and measuring effects on feeding or changes in body weight by any of the methods well known in the art (see for example WO 02/080860, or Experimental Details below).

OSGPR116 modulator activity can be determined in vitro or in vivo by contacting cells expressing OSGPR116 or a variant polypeptide with an agent under test and by monitoring the effect mediated by OSGPR116 or variant polypeptide. Thus, a test agent may be contacted with isolated cells which express OSGPR116 or a variant polypeptide. The cells may be provided in culture. Alternatively, cells may be disrupted and cell membranes isolated and used. OSGPR116 receptor protein may also be solubilized with the use of detergents (e.g. non-ionic detergents, such as digitonin), and the receptor purified and reconstituted in lipid vesicles, with other purified proteins as required. Such reconstituted ligand-stimulated GPCRs, that can activate second messenger systems, are well known in the art, and can be used in the practice of this invention.

The OSGPR116 or variant polypeptide may be naturally or recombinantly expressed. Preferably, an assay is carried out in vitro using cells expressing recombinant polypeptide or using membranes from such cells. Suitable eucaryotic and procaryotic cells are discussed above. In one embodiment, a cell type known to naturally express OSGPR116 receptors is used, e.g. an adipose or pancreatic cell.

This invention provides a process for identifying a chemical compound which specifically binds to a mammalian OSGPR116 receptor which comprises contacting cells containing DNA encoding, and expressing on their cell surface, the mammalian OSGPR116 receptor, wherein such cells do not normally express the mammalian OSGPR116 receptor, with the compound under conditions suitable for binding, and detecting specific binding of the chemical compound to the mammalian OSGPR116 receptor.

This invention further provides a process for identifying a chemical compound which specifically binds to a mammalian OSGPR116 receptor which comprises contacting a membrane preparation from cells containing DNA encoding, and expressing on their cell surface, the mammalian OSGPR116 receptor, wherein such cells do not normally express the mammalian OSGPR116 receptor, with the compound under conditions suitable for binding, and detecting specific binding of the chemical compound to the mammalian OSGPR116 receptor.

In a further embodiment of these processes for identifying a chemical compound which specifically binds to a mammalian OSGPR116 receptor the contacting of the cells or membrane preparation with the compound is performed in the presence of a ligand for the OSGPR116 receptor, wherein the ligand is a lipid amide or fatty acid amide. The ligand can be is a fatty acid alkanolamide, for example a fatty acid ethanolamides. In a further embodiment, a lipid amide ligand is selected from oleoyl ethanolamide, palmitoyl ethanolamide, stearoyl ethanolamide, linoleoyl ethanolamide, linolenoyl ethanolamide and oleamide, or a functional analog or homolog of one of these compounds.

In one embodiment, the mammalian OSGPR116 receptor is a human OSGPR116 receptor. In another embodiment, the mammalian OSGPR116 receptor has the same or substantially the same amino acid sequence as the human OSGPR116 receptor of FIG. 2 (SEQ ID NO:2).

In another embodiment, the mammalian OSGPR116 receptor is a rat OSGPR116 receptor. In another embodiment, the mammalian OSGPR116 receptor has the same or substantially the same amino acid sequence as the rat OSGPR116 receptor described in FIGS. 4A–4B of U.S. Pat. No. 6,468,756.

In another embodiment, the mammalian OSGPR116 receptor is a mouse OSGPR116 receptor. In another embodiment, the mammalian OSGPR116 receptor has the same or substantially the same amino acid sequence as the mouse OSGPR116 receptor of FIG. 4 (SEQ ID NO:4).

In one embodiment, the compound is not previously known to bind to a mammalian OSGPR116 receptor. In one embodiment, the cell is an insect cell. In one embodiment, the cell is a mammalian cell. In another embodiment, the cell is a COS-7 cell, 293 human embryonic kidney cell, a CHO cell, a NIH-3T3 cell, a mouse Y1 cell, or a LM(tk-) cell. In another embodiment, the compound is a compound not previously known to bind to a mammalian OSGPR116 receptor. This invention provides a compound identified by the preceding process of this invention.

This invention still further provides a process involving competitive binding for identifying a chemical compound which specifically binds to a mammalian OSGPR116 receptor which comprises separately contacting cells expressing on their cell surface the mammalian OSGPR116 receptor, wherein such cells do not normally express the mammalian OSGPR116 receptor, with both the chemical compound and a lipid amide or fatty acid amide ligand, known to bind to the receptor, and with only the ligand, under conditions suitable for binding of such a ligand to the receptor, and detecting specific binding of the chemical compound to the mammalian OSGPR116 receptor, a decrease in the binding of the ligand to the mammalian OSGPR116 receptor in the presence of the chemical compound being tested indicating that such chemical compound binds to the mammalian OSGPR116 receptor.

This invention also provides a process involving competitive binding for identifying a chemical compound which specifically binds to a mammalian OSGPR116 receptor which comprises separately contacting a membrane preparation from cells expressing on their cell surface the mammalian OSGPR116 receptor, wherein such cells do not normally express the mammalian OSGPR116 receptor, with both the chemical compound and a lipid amide or fatty acid amide ligand, known to bind to the receptor, and with only the ligand, under conditions suitable for binding of such a ligand to the receptor, and detecting specific binding of the chemical compound to the mammalian OSGPR116 receptor, a decrease in the binding of the ligand to the mammalian OSGPR116 receptor in the presence of the chemical compound being tested indicating that such chemical compound binds to the mammalian OSGPR116 receptor.

In specific embodiments of these processes the lipid amide or fatty acid amide ligand is a fatty acid alkanolamide, for example a fatty acid ethanolamides. In a further embodiment, lipid amides are selected from oleoyl ethanolamide, palmitoyl ethanolamide, stearoyl ethanolamide, linoleoyl ethanolamide, linolenoyl ethanolamide and oleamide, or a functional analog or homolog of one of these compounds.

In one embodiment, the mammalian OSGPR116 receptor is a human OSGPR116 receptor. In another embodiment, the mammalian OSGPR116 receptor is a rat OSGPR116 receptor. In another embodiment, the mammalian OSGPR116 receptor is a mouse OSGPR116 receptor. In a further embodiment, the cell is an insect cell. In another embodiment, the cell is a mammalian cell. In another embodiment, the cell is a yeast cell. In another embodiment, the cell is a COS-7 cell, 293 human embryonic kidney cell, a CHO cell, a NIH-3T3 cell, a mouse Y1 cell, or a LM(tk-) cell. In another embodiment, the compound is not previously known to bind to a mammalian OSGPR116 receptor. This invention provides a compound identified by the preceding processes of this invention.

This invention provides a method of screening a plurality of chemical compounds not known to bind to a mammalian OSGPR116 receptor to identify a compound which specifically binds to the mammalian OSGPR116 receptor, which comprises (a) contacting cells transfected with, and expressing, DNA encoding the mammalian OSGPR116 receptor with a compound known to bind specifically to the mammalian OSGPR116 receptor (e.g. a ligand); (b) contacting the cells of step (a) with the plurality of compounds not known to bind specifically to the mammalian OSGPR116 receptor, under conditions permitting binding of compounds known to bind to the mammalian OSGPR116 receptor; (c)

determining whether the binding of the compound known to bind to the mammalian OSGPR116 receptor is reduced in the presence of the plurality of compounds, relative to the binding of the compound in the absence of the plurality of compounds; and if so (d) separately determining the binding to the mammalian OSGPR116 receptor of each compound included in the plurality of compounds, so as to thereby identify any compound included therein which specifically binds to the mammalian OSGPR116 receptor.

This invention provides a method of screening a plurality of chemical compounds not known to bind to a mammalian OSGPR116 receptor to identify a compound which specifically binds to the mammalian OSGPR116 receptor, which comprises (a) contacting a membrane preparation from cells transfected with, and expressing, DNA encoding the mammalian OSGPR116 receptor with a compound known to bind specifically to the mammalian OSGPR116 receptor (e.g. a ligand), and with the plurality of compounds not known to bind specifically to the mammalian OSGPR116 receptor, under conditions permitting binding of compounds known to bind to the mammalian OSGPR116 receptor; (b) determining whether the binding of a compound known to bind to the mammalian OSGPR116 receptor is reduced in the presence of the plurality of compounds, relative to the binding of the compound in the absence of the plurality of compounds; and if so (c) separately determining the binding to the mammalian OSGPR116 receptor of each compound included in the plurality of compounds, so as to thereby identify any compound included therein which specifically binds to the mammalian OSGPR116 receptor.

In specific embodiments of these methods the compound known to bind to the mammalian OSGPR116 receptor is a lipid amide or fatty acid amide ligand. In one embodiment it is a fatty acid alkanolamide, for example a fatty acid ethanolamides. In a further embodiment, lipid amides are selected from oleoyl ethanolamide, palmitoyl ethanolamide, stearoyl ethanolamide, linoleoyl ethanolamide, linolenoyl ethanolamide and oleamide, or a functional analog or homolog of one of these compounds.

In one embodiment, the mammalian OSGPR116 receptor is a human OSGPR116 receptor. In a further embodiment, the mammalian OSGPR116 receptor is a rat OSGPR116 receptor. In another embodiment, the mammalian OSGPR116 receptor is a mouse OSGPR116 receptor. In another embodiment, the cell is a mammalian cell. In another embodiment, the cell is a yeast cell. In another embodiment the cell is a COS-7 cell, a 293 human embryonic kidney cell, a LM(tk-) cell, a CHO cell, a mouse Y1 cell, or an NIH-3T3 cell.

This invention provides a method of detecting expression of a mammalian OSGPR116 receptor by detecting the presence of mRNA coding for the mammalian OSGPR116 receptor which comprises obtaining total mRNA from the cell and contacting the mRNA so obtained with a nucleic acid probe according to this invention under hybridizing conditions, detecting the presence of mRNA hybridized to the probe, and thereby detecting the expression of the mammalian OSGPR116 receptor by the cell.

This invention provides a method of detecting the presence of a mammalian OSGPR116 receptor on the surface of a cell which comprises contacting the cell with an antibody according to this invention under conditions permitting binding of the antibody to the receptor, detecting the presence of the antibody bound to the cell, and thereby detecting the presence of the mammalian OSGPR116 receptor on the surface of the cell.

This invention provides a method of determining the physiological effects of varying levels of activity of mammalian OSGPR116 receptors which comprises producing a transgenic, nonhuman mammal in accordance with this invention whose levels of mammalian OSGPR116 receptor activity are varied by use of an inducible promoter which regulates mammalian OSGPR116 receptor expression.

This invention provides a method of determining the physiological effects of varying levels of activity of mammalian OSGPR116 receptors which comprises producing a panel of transgenic, nonhuman mammals in accordance with this invention each expressing a different amount of mammalian OSGPR116 receptor.

This invention provides a method for identifying an antagonist capable of alleviating an abnormality wherein the abnormality is alleviated by decreasing the activity of a mammalian OSGPR116 receptor comprising administering a compound to a transgenic, nonhuman mammal according to this invention, and determining whether the compound alleviates any physiological and/or behavioral abnormality displayed by the transgenic, nonhuman mammal as a result of overactivity of a mammalian OSGPR116 receptor, the alleviation of such abnormality identifying the compound as an antagonist. In one embodiment, the mammalian OSGPR116 receptor is a human OSGPR116 receptor. In a further embodiment, the mammalian OSGPR116 receptor is a rat OSGPR116 receptor. In another embodiment, the mammalian OSGPR116 receptor is a mouse OSGPR116 receptor. The invention provides an antagonist identified by the preceding method according to this invention. This invention provides a composition, e.g. a pharmaceutical composition, comprising an antagonist according to this invention and a carrier, e.g. a pharmaceutically acceptable carrier. This invention provides a method of treating an abnormality in a subject wherein the abnormality is alleviated by decreasing the activity of a mammalian OSGPR116 receptor which comprises administering to the subject an effective amount of the pharmaceutical composition according to this invention so as to thereby treat the abnormality.

This invention provides a method for identifying an agonist capable of alleviating an abnormality in a subject wherein the abnormality is alleviated by increasing the activity of a mammalian OSGPR116 receptor comprising administering a compound to a transgenic, nonhuman mammal according to this invention, and determining whether the compound alleviates any physiological and/or behavioral abnormality displayed by the transgenic, nonhuman mammal, the alleviation of such an abnormality identifying the compound as an agonist. In one embodiment, the mammalian OSGPR116 receptor is a human OSGPR116 receptor. In a further embodiment, the mammalian OSGPR116 receptor is a rat OSGPR116 receptor. In another embodiment, the mammalian OSGPR116 receptor is a mouse OSGPR116 receptor. This invention provides an agonist identified by the preceding method according to this invention. This invention provides a composition, e.g. a pharmaceutical composition, comprising an agonist identified by the method according to this invention and a carrier, e.g. a pharmaceutically acceptable carrier.

This invention provides a method of treating an abnormality in a subject wherein the abnormality is alleviated by increasing the activity of a mammalian OSGPR116 receptor which comprises administering to the subject an effective amount of the pharmaceutical composition according to this invention so as to thereby treat the abnormality.

This invention provides a method for diagnosing a predisposition to a disorder associated with the activity of a specific mammalian allele which comprises: (a) obtaining DNA of subjects suffering from the disorder; (b) performing a restriction digest of the DNA with a panel of restriction enzymes; (c) electrophoretically separating the resulting DNA fragments on a sizing gel; (d) contacting the resulting gel with a nucleic acid probe capable of specifically hybridizing with a unique sequence included within the sequence of a nucleic acid molecule encoding a mammalian OSGPR116 receptor and labeled with a detectable marker; (e) detecting labeled bands which have hybridized to the DNA encoding a mammalian OSGPR116 receptor to create a unique band pattern specific to the DNA of subjects suffering from the disorder; (f) repeating steps (a)–(e) with DNA obtained for diagnosis from subjects not yet suffering from the disorder; and (g) comparing the unique band pattern specific to the DNA of subjects suffering from the disorder from step (e) with the band pattern from step (f) for subjects not yet suffering from the disorder so as to determine whether the patterns are the same or different and thereby diagnose predisposition to the disorder if the patterns are the same.

In one embodiment, the disorder is a disorder associated with the activity of a specific mammalian allele is diagnosed.

This invention provides a method of preparing a purified mammalian OSGPR116 receptor according to this invention which comprises: (a) culturing cells which express the mammalian OSGPR116 receptor; (b) recovering the mammalian OSGPR116 receptor from the cells; and (c) purifying the mammalian OSGPR116 receptor so recovered.

This invention provides a method of preparing the purified mammalian OSGPR116 receptor according to this invention which comprises: (a) inserting a nucleic acid encoding the mammalian OSGPR116 receptor into a suitable expression vector; (b) introducing the resulting vector into a suitable host cell; (c) placing the resulting host cell in suitable conditions permitting the production of the mammalian OSGPR116 receptor; (d) recovering the mammalian OSGPR116 receptor so produced; and optionally (e) isolating and/or purifying the mammalian OSGPR116 receptor so recovered.

This invention provides a process for determining whether a chemical compound is a mammalian OSGPR116 receptor agonist which comprises contacting cells transfected with and expressing DNA encoding the mammalian OSGPR116 receptor with the compound under conditions permitting the activation of the mammalian OSGPR116 receptor, and detecting any increase in mammalian OSGPR116 receptor activity, so as to thereby determine whether the compound is a mammalian OSGPR116 receptor agonist.

This invention provides a process for determining whether a chemical compound is a mammalian OSGPR116 receptor antagonist which comprises contacting cells transfected with and expressing DNA encoding the mammalian OSGPR116 receptor with the compound in the presence of a known mammalian OSGPR116 receptor agonist, under conditions permitting the activation of the mammalian OSGPR116 receptor, and detecting any decrease in mammalian OSGPR116 receptor activity, so as to thereby determine whether the compound is a mammalian OSGPR116 receptor antagonist.

In one embodiment, the mammalian OSGPR116 receptor is a human OSGPR116 receptor. In another embodiment, the mammalian OSGPR116 receptor is a rat OSGPR116 receptor. In another embodiment, the mammalian OSGPR116 receptor is a mouse OSGPR116 receptor.

This invention provides a composition, for example a pharmaceutical composition, which comprises an amount of a mammalian OSGPR116 receptor agonist determined by a process according to this invention effective to increase activity of a mammalian OSGPR116 receptor and a carrier, for example, a pharmaceutically acceptable carrier. In one embodiment, the mammalian OSGPR116 receptor agonist is not previously known.

This invention provides a composition, for example a pharmaceutical composition, which comprises an amount of a mammalian OSGPR116 receptor antagonist determined by a process according to this invention effective to reduce activity of a mammalian OSGPR116 receptor and a carrier, for example, a pharmaceutically acceptable carrier. In one embodiment, the mammalian OSGPR116 receptor antagonist is not previously known.

This invention provides a method of preparing a composition, for example a pharmaceutical composition, comprising a chemical compound which specifically binds to a mammalian OSGPR116 receptor, which comprises separately contacting cells expressing on their cell surface the mammalian OSGPR116 receptor, wherein such cells do not normally express the mammalian OSGPR116 receptor, with both a test chemical compound and a lipid amide or fatty acid amide ligand, known to bind to the receptor, and with only the ligand, under conditions suitable for binding of such a ligand to the receptor, and detecting specific binding of the test chemical compound to the mammalian OSGPR116 receptor, a decrease in the binding of the ligand to the mammalian OSGPR116 receptor in the presence of the test chemical compound indicating that said test chemical compound binds specifically to the mammalian OSGPR116 receptor, and admixing the test chemical so identified, or a functional analog or homolog of said test chemical, with a carrier, thereby preparing said composition. In one embodiment of this method the mammalian OSGPR116 receptor is a human OSGPR116 receptor. In another embodiment it is a rat or mouse OSGPR116 receptor.

This invention provides a method of preparing a composition, for example a pharmaceutical composition, comprising a chemical compound which specifically binds to a mammalian OSGPR116 receptor, which comprises separately contacting a membrane preparation from cells expressing on their cell surface the mammalian OSGPR116 receptor, wherein such cells do not normally express the mammalian OSGPR116 receptor, with both a test chemical compound and a lipid amide or fatty acid amide ligand, known to bind to the receptor, and with only the ligand, under conditions suitable for binding of such a ligand to the receptor, and detecting specific binding of the test chemical compound to the mammalian OSGPR116 receptor, a decrease in the binding of the ligand to the mammalian OSGPR116 receptor in the presence of the test chemical compound indicating that said test chemical compound binds specifically to the mammalian OSGPR116 receptor, and admixing the test chemical so identified, or a functional analog or homolog of said test chemical, with a carrier, thereby preparing said composition. In one embodiment of this method the mammalian OSGPR116 receptor is a human OSGPR116 receptor. In another embodiment it is a rat or mouse OSGPR116 receptor.

This invention provides a process for determining whether a chemical compound specifically binds to and activates a mammalian OSGPR116 receptor, which comprises contacting cells producing a second messenger response and expressing on their cell surface the mammalian OSGPR116 receptor, wherein such cells do not normally express the mammalian OSGPR116 receptor, with the chemical compound under conditions suitable for activation of the mammalian OSGPR116 receptor, and measuring the second messenger response in the presence and in the absence of the chemical compound, a change, e.g. an increase, in the second messenger response in the presence of the chemical compound indicating that the compound activates the mammalian OSGPR116 receptor.

In one embodiment, the second messenger response comprises chloride channel activation and the change in second messenger is an increase in the level of chloride current. In another embodiment, the second messenger response comprises change in intracellular calcium levels and the change in second messenger is an increase in the measure of intracellular calcium. In another embodiment, the second messenger response comprises release of inositol phosphate and the change in second messenger is an increase in the level of inositol phosphate. In another embodiment, the second messenger response comprises release of arachidonic acid and the change in second messenger is an increase in the level of arachidonic acid. In yet another embodiment, the second messenger response comprises GTPγS ligand binding and the change in second messenger is an increase in GTPγS ligand binding. In another embodiment, the second messenger response comprises activation of MAP kinase and the change in second messenger response is an increase in MAP kinase activation. In a further embodiment, the second messenger response comprises cAMP accumulation and the change in second messenger response is an increase in cAMP accumulation.

This invention provides a process for determining whether a chemical compound specifically binds to and inhibits activation of a mammalian OSGPR116 receptor, which comprises separately contacting cells producing a second messenger response and expressing on their cell surface the mammalian OSGPR116 receptor, wherein such cells do not normally express the mammalian OSGPR116 receptor, with both the chemical compound and a second chemical compound known to activate the mammalian OSGPR116 receptor, and with only the second chemical compound, under conditions suitable for activation of the mammalian OSGPR116 receptor, and measuring the second messenger response in the presence of only the second chemical compound and in the presence of both the second chemical compound and the chemical compound, a smaller change, e.g. increase, in the second messenger response in the presence of both the chemical compound and the second chemical compound than in the presence of only the second chemical compound indicating that the chemical compound inhibits activation of the mammalian OSGPR116 receptor.

In one embodiment, the second messenger response comprises chloride channel activation and the change in second messenger response is a smaller increase in the level of chloride current in the presence of both the chemical compound and the second chemical compound than in the presence of only the second chemical compound. In another embodiment, the second messenger response comprises change in intracellular calcium levels and the change in second messenger response is a smaller increase in the measure of intracellular calcium in the presence of both the chemical compound and the second chemical compound than in the presence of only the second chemical compound. In another embodiment, the second messenger response comprises release of inositol phosphate and the change in second messenger response is a smaller increase in the level of inositol phosphate in the presence of both the chemical compound and the second chemical compound than in the presence of only the second chemical compound.

In one embodiment, the second messenger response comprises activation of MAP kinase and the change in second messenger response is a smaller increase in the level of MAP kinase activation in the presence of both the chemical compound and the second chemical compound than in the presence of only the second chemical compound. In another embodiment, the second messenger response comprises change in cAMP levels and the change in second messenger response is a smaller change in the level of cAMP in the presence of both the chemical compound and the second chemical compound than in the presence of only the second chemical compound. In another embodiment, the second messenger response comprises release of arachidonic acid and the change in second messenger response is an increase in the level of arachidonic acid levels in the presence of both the chemical compound and the second chemical compound than in the presence of only the second chemical compound. In a further embodiment, the second messenger response comprises GTPγS ligand binding and the change in second messenger is a smaller increase in GTPγS ligand binding in the presence of both the chemical compound and the second chemical compound than in the presence of only the second chemical compound.

In one embodiment, the mammalian OSGPR116 receptor is a human OSGPR116 receptor. In a further embodiment, the mammalian OSGPR116 receptor is a rat OSGPR116 receptor. In another embodiment, the mammalian OSGPR116 receptor is a mouse OSGPR116 receptor. In another embodiment, the cell is an insect cell. In another embodiment, the cell is a yeast cell. In another embodiment, the cell is a mammalian cell. In another embodiment, the mammalian cell is a COS-7 cell, CHO cell, 293 human embryonic kidney cell, NIH-3T3 cell or LM(tk-) cell. In another embodiment, the compound is not previously known to bind to a mammalian OSGPR116 receptor.

In a prefered embodiment of the above processes of the invention, the second compound is a lipid amide, a fatty acid amide, a fatty acid alkanolamide, a fatty acid ethanolamide, or any of the compounds described in WO 02/080860 (e.g. compounds of formula I, Ia, II, III, IV, V, VI, or VII) as compounds for reducing body fat and modulating fatty acid metabolism. In a further embodiment, lipid amides are selected from oleoyl ethanolamide, palmitoyl ethanolamide, stearoyl ethanolamide, linoleoyl ethanolamide, linolenoyl ethanolamide and oleamide, or a functional analog or homolog of one of these compounds.

This invention provides a compound determined by a process according to this invention and a composition, for example, a pharmaceutical composition, which comprises an amount of a mammalian OSGPR116 receptor agonist determined to be such by a process according to this invention effective to increase activity of the mammalian OSGPR116 receptor and a carrier, for example, a pharmaceutically acceptable carrier. In one embodiment, the mammalian OSGPR116 receptor agonist is not previously known.

This invention provides a compound determined by a process according to this invention and a composition, for example, a pharmaceutical composition, which comprises an amount of a mammalian OSGPR116 receptor antagonist determined to be such by a process according to this invention, effective to reduce activity of the mammalian OSGPR116 receptor and a carrier, for example, a pharmaceutically acceptable carrier. In one embodiment, the mammalian OSGPR116 receptor antagonist is not previously known.

This invention provides a method of screening a plurality of chemical compounds not known to activate a mammalian OSGPR116 receptor to identify a compound which activates the mammalian OSGPR116 receptor which comprises: (a) contacting cells transfected with and expressing the mammalian OSGPR116 receptor with the plurality of compounds not known to activate the mammalian OSGPR116 receptor, under conditions permitting activation of the mammalian OSGPR116 receptor; (b) determining whether the activity of the mammalian OSGPR116 receptor is increased in the presence of one or more of the compounds; and if so (c) separately determining whether the activation of the mammalian OSGPR116 receptor is increased by any compound included in the plurality of compounds, so as to thereby identify each compound which activates the mammalian OSGPR116 receptor. In one embodiment, the mammalian OSGPR116 receptor is a human OSGPR116 receptor. In a further embodiment, the mammalian OSGPR116 receptor is a rat OSGPR116 receptor. In another embodiment, the mammalian OSGPR116 receptor is a mouse OSGPR116 receptor.

This invention provides a method of screening a plurality of chemical compounds not known to inhibit the activation of a mammalian OSGPR116 receptor to identify a compound which inhibits the activation of the mammalian OSGPR116 receptor, which comprises: (a) contacting cells transfected with and expressing the mammalian OSGPR116 receptor with the plurality of compounds in the presence of a known mammalian OSGPR116 receptor agonist, under conditions permitting activation of the mammalian OSGPR116 receptor; (b) determining whether the extent or amount of activation of the mammalian OSGPR116 receptor is reduced in the presence of one or more of the compounds, relative to the extent or amount of activation of the mammalian OSGPR116 receptor in the absence of such one or more compounds; and if so (c) separately determining whether each such compound inhibits activation of the mammalian OSGPR116 receptor for each compound included in the plurality of compounds, so as to thereby identify any compound included in such plurality of compounds which inhibits the activation of the mammalian OSGPR116 receptor.

In one embodiment, the mammalian OSGPR116 receptor is a human OSGPR116 receptor. In a further embodiment, the mammalian OSGPR116 receptor is a rat OSGPR116 receptor. In another embodiment, the mammalian OSGPR116 receptor is a mouse OSGPR116 receptor. In another embodiment, the cell is a yeast cell. In another embodiment, the cell is a mammalian cell. In another embodiment, the mammalian cell is an adipose or pancreatic cell. In another embodiment, the cell is a COS-7 cell, a 293 human embryonic kidney cell, a LM(tk-) cell or an NIH-3T3 cell.

This invention provides a composition, for example a pharmaceutical composition, comprising a compound identified by a method according to this invention in an amount effective to increase mammalian OSGPR116 receptor activity and a carrier, for example, a pharmaceutically acceptable carrier.

This invention provides a composition, for example, a pharmaceutical composition, comprising a compound identified by a method according to this invention in an amount effective to decrease mammalian OSGPR116 receptor activity and a carrier, for example, a pharmaceutically acceptable carrier.

This invention provides a method of treating an abnormality in a subject wherein the abnormality is alleviated by increasing the activity of a mammalian OSGPR116 receptor which comprises administering to the subject a compound which is a mammalian OSGPR116 receptor agonist in an amount effective to treat the abnormality. In one embodiment, the abnormality is a regulation of a steroid hormone disorder, an epinephrine release disorder, a gastrointestinal disorder, a cardiovascular disorder, an electrolyte balance disorder, hypertension, diabetes, a respiratory disorder, asthma, a reproductive function disorder, an immune disorder, an endocrine disorder, a musculoskeletal disorder, a neuroendocrine disorder, a cognitive disorder, a memory disorder, somatosensory and neurotransmission disorders, a motor coordination disorder, a sensory integration disorder, a motor integration disorder, a dopaminergic function disorder, an appetite disorder, such as anorexia or obesity, a sensory transmission disorder, an olfaction disorder, an autonomic nervous system disorder, pain, psychotic behavior, affective disorder, migraine, cancer, proliferative diseases, wound healing, tissue regeneration, blood coagulation-related disorders, developmental disorders, or ischemia-reperfusion injury-related diseases.

This invention provides a method of treating an abnormality in a subject wherein the abnormality is alleviated by decreasing the activity of a mammalian OSGPR116 receptor which comprises administering to the subject a compound which is a mammalian OSGPR116 receptor antagonist in an amount effective to treat the abnormality. In one embodiment, the abnormality is a regulation of a steroid hormone disorder, an epinephrine release disorder, a gastrointestinal disorder, a cardiovascular disorder, an electrolyte balance disorder, hypertension, diabetes, a respiratory disorder, asthma, a reproductive function disorder, an immune disorder, an endocrine disorder, a musculoskeletal disorder, a neuroendocrine disorder, a cognitive disorder, a memory disorder, somatosensory and neurotransmission disorders, a motor coordination disorder, a sensory integration disorder, a motor integration disorder, a dopaminergic function disorder, an appetite disorder, such as anorexia or obesity, a somatosensory neurotransmission disorder, an olfaction disorder, an autonomic nervous system disorder, pain, psychotic behavior, affective disorder, migraine, cancer, proliferative diseases, wound healing, tissue regeneration, blood coagulation-related disorders, developmental disorders, or ischemia-reperfusion injury-related diseases.

This invention provides a process for making a composition of matter which specifically binds to a mammalian OSGPR116 receptor which comprises identifying a chemical compound using a process in accordance with this invention and then synthesizing the chemical compound or a novel structural and functional analog or homolog thereof. In one embodiment, the mammalian OSGPR116 receptor is a human OSGPR116 receptor. In another embodiment, the mammalian OSGPR116 receptor is a rat OSGPR116 receptor. In another embodiment, the mammalian OSGPR116 receptor is a mouse OSGPR116 receptor.

This invention provides a process for preparing a composition, for example a pharmaceutical composition which comprises admixing a carrier, for example, a pharmaceutically acceptable carrier, and a pharmaceutically effective amount of a chemical compound identified by a process in accordance with this invention or a novel structural and functional analog or homolog thereof. In one embodiment, the mammalian OSGPR116 receptor is a human OSGPR116 receptor. In another embodiment, the mammalian OSGPR116 receptor is a rat OSGPR116 receptor. In another embodiment, the mammalian OSGPR116 receptor is a mouse OSGPR116 receptor.

Thus, once the gene for a targeted receptor subtype is cloned, it is placed into a recipient cell which then expresses the targeted receptor subtype on its surface. This cell, which expresses a single population of the targeted human receptor subtype, is then propagated resulting in the establishment of a cell line. This cell line, which constitutes a drug discovery system, is used in two different types of assays: binding assays and functional assays. In binding assays, the affinity of a compound for both the receptor subtype that is the target of a particular drug discovery program and other receptor subtypes that could be associated with side effects are measured. These measurements enable one to predict the potency of a compound, as well as the degree of selectivity that the compound has for the targeted receptor subtype over other receptor subtypes. The data obtained from binding assays also enable chemists to design compounds toward or away from one or more of the relevant subtypes, as appropriate, for optimal therapeutic efficacy. In functional assays, the nature of the response of the receptor subtype to the compound is determined. Data from the functional assays show whether the compound is acting to inhibit or enhance the activity of the receptor subtype, thus enabling pharmacologists to evaluate compounds rapidly at their ultimate human receptor subtypes targets permitting chemists to rationally design drugs that will be more effective and have fewer or substantially less severe side effects than existing drugs.

Approaches to designing and synthesizing receptor subtype-selective compounds are well known and include traditional medicinal chemistry and the newer technology of combinatorial chemistry, both of which are supported by computer-assisted molecular modeling. With such approaches, chemists and pharmacologists use their knowledge of the structures of the targeted receptor subtype and compounds determined to bind and/or activate or inhibit activation of the receptor subtype to design and synthesize structures that will have activity at these receptor subtypes.

Combinatorial chemistry involves automated synthesis of a variety of novel compounds by assembling them using different combinations of chemical building blocks. The use of combinatorial chemistry greatly accelerates the process of generating compounds. The resulting arrays of compounds are called libraries and are used to screen for compounds ("lead compounds") that demonstrate a sufficient level of activity at receptors of interest. Using combinatorial chemistry it is possible to synthesize "focused" libraries of compounds anticipated to be highly biased toward the receptor target of interest.

Once lead compounds are identified, whether through the use of combinatorial chemistry or traditional medicinal chemistry or otherwise, a variety of homologs and analogs are prepared to facilitate an understanding of the relationship between chemical structure and biological or functional activity. These studies define structure activity relationships which are then used to design drugs with improved potency, selectivity and pharmacokinetic properties. Combinatorial chemistry is also used to rapidly generate a variety of structures for lead optimization. Traditional medicinal chemistry, which involves the synthesis of compounds one at a time, is also used for further refinement and to generate compounds not accessible by automated techniques. Once such drugs are defined the production is scaled up using standard chemical manufacturing methodologies utilized throughout the pharmaceutical and chemistry industry.

In one aspect of this invention, OSGPR116 receptor activity is monitored by measuring a Gi/o-coupled readout. Gi/o-coupled readout can be monitored using an electro-physiological method to determine the activity of G-protein regulated $Ca^{2+}$ or $K^+$ channels or by using fluorescent dye to measure changes in intracellular $Ca^{2+}$ levels. Other methods that can typically be used to monitor receptor activity involved measuring levels of or activity of GTPγS or cAMP.

Yeast assays may be used to screen for agents that modulate the activity of OSGPR116 or variant polypeptides. A typical yeast assay involves heterologously expressing OSGPR116 or a variant polypeptide in a modified yeast strain containing multiple reporter genes, typically FUS1-HIS 3 and FUS1-lacZ, each linked to an endogenous MAPK cascade-based signal transduction pathway. This pathway is normally linked to pheromone receptors, but can be coupled to foreign receptors by replacement of the yeast G-protein with yeast/mammalian G-protein chimeras. Strains may also contain further gene deletions, such as deletions of SST2 and FAR1, to potentiate the assay. Ligand activation of the heterologous receptor can be monitored for example either as cell growth in the absence of histidine or with a suitable substrate for beta-galactosidase (lacZ). Such technology is well known in the art. See for example WO 99/14344, WO 00/12704, or U.S. Pat. No. 6,100,042.

Alternatively melanophore assays may be used to screen for modulators of OSGPR116. OSGPR116 or a variant polypeptide can be heterologously expressed in *Xenopus laevis* melanophores and their activation or inhibition can be measured by either melanosome dispersion or aggregation. Basically, melanosome dispersion is promoted by activation of adenylate cyclase or phospholipase C, i.e. Gs and Gq mediated signalling respectively, whereas aggregation results from activation of Gi-protein resulting in inhibition of adenylate cyclase. Hence, ligand activation of the heterologous receptor can be measured simply by measuring the change in light transmittance through the cells or by imaging the cell response.

Preferably, control experiments are carried out on cells which do not express OSGPR116 or a variant polypeptide to establish whether the observed responses are the result of activation of the OSGPR116 or the variant polypeptide.

Suitable test substances which can be tested in the above assays include combinatorial libraries, defined chemical entities, peptide and peptide mimetics, oligonucleotides and natural product libraries, such as display (e.g. phage display libraries) and antibody products. In one embodiment, the test substance is a fatty acid amide or lipid amide or a closely related compound. Assays may also be carried out using known ligands of other G-protein coupled receptors to identify additional ligands which act as agonists of OSGPR116.

Test substances may be used in an initial screen of, for example, 10 substances per reaction, and the substances of these batches which show inhibition or activation tested individually. Test substances may be used at a concentration of from 1 nM to 1000 μM, preferably from 1 μM to 100 μM, more preferably from 1 μM to 10 μM.

Agents which modulate OSGPR116 activity and which have been identified by assays in accordance with the invention can be used in the treatment or prophylaxis of feeding disorders which are responsive to regulation of OSGPR116 receptor activity, and are one embodiment of this invention Agents which activate OSGPR116 receptor activity and/or which have been identified as inhibitors of feeding are a preferred embodiment. In particular, such agents may be used in the treatment of obesity and eating disorders, and diseases associated with these conditions, including diabetes, dyslipidemia and cardiovascular disease associated with obesity, including atherosclerosis, arteriosclerosis, hypercholesteremia and hypertriglyceridemia, type II diabetes mellitus, type I diabetes, insulin resistance, hyperlipidemia, and metabolic syndrome (syndrome X).

In an alternative embodiment, agents which inhibit OSGPR116 receptor activity and/or which have been identified as stimulators of feeding are also useful. In particular, such agents may be used in the treatment of anorexia nervosa, bulimia and other feeding disorders, and cachexia associated with cancer, AIDS, inflammatory conditions and other conditions.

The amount of a OSGPR116 modulator which is required to achieve the desired biological effect will, of course, depend on a number of factors, for example, the mode of administration and the precise clinical condition of the recipient. In general, the daily dose will be in the range of 0.1–1000 mg/kg, typically 0.1–100 mg/kg. An intravenous dose may, for example, be in the range of 0.01 mg to 100 mg/kg, typically 0.01 to 10 mg/kg, which may conveniently be administered as an infusion of from 0.1 µg to 1 mg, per minute. Infusion fluids suitable for this purpose may contain, for example, from 0.01 µg to 0.1 mg, per milliliter. Unit doses may contain, for example, from 0.01 µg to 1 g of a OSGPR116 modulator. Thus ampoules for injection may contain, for example, from 0.01 µg to 0.1 g and orally administrable unit dose formulations, such as tablets or capsules, may contain, for example, from 0.1 mg to 1 g.

An OSGPR116 modulator may be employed in the treatment of a OSGPR116 mediated disease as the compound per se, but is preferably presented with an acceptable carrier in the form of a pharmaceutical formulation. The carrier must, of course, be acceptable in the sense of being compatible with the other ingredients of the formulation and must not be deleterious to the recipient. The carrier may be a solid or a liquid, or both, and is preferably formulated with the OSGPR116 modulator as a unit-dose formulation, for example, a tablet, which may contain from 0.05% to 95% by weight of the OSGPR116 modulator.

The formulations include those suitable for oral, rectal, topical, buccal (e.g. sub-lingual) and parenteral (e.g. subcutaneous, intramuscular, intradermal or intravenous) administration. Formulations suitable for oral administration may be presented in discrete units, such as capsules, cachets, lozenges or tablets, each containing a predetermined amount of a OSGPR116 modulator; as a powder or granules; as a solution or a suspension in an aqueous or non-aqueous liquid; or as an oil-in-water or water-in-oil emulsion. In general, the formulations are prepared by uniformly and intimately admixing the active OSGPR116 modulator with a liquid or finely divided solid carrier, or both, and then, if necessary, shaping the product. For example, a tablet may be prepared by compressing or moulding a powder or granules of the OSGPR116 modulator optionally with one or more accessory ingredients. Compressed tablets may be prepared by compressing, in a suitable machine, the compound in a free-flowing form, such as a powder or granules optionally mixed with a binder, lubricant, inert diluent and/or surface active/dispersing agent(s). Moulded tablets may be made by moulding, in a suitable machine, the powdered compound moistened with an inert liquid diluent.

Formulations suitable for buccal (sub-lingual) administration include lozenges comprising a OSGPR116 modulator in a flavoured base, usually sucrose and acacia or tragacanth, and pastilles comprising the OSGPR116 modulator in an inert base such as gelatin and glycerin or sucrose and acacia.

Formulations of the present invention suitable for parenteral administration conveniently comprise sterile aqueous preparations of an OSGPR116 modulator, preferably isotonic with the blood of the intended recipient. These preparations are preferably administered intravenously, although administration may also be effected by means of subcutaneous, intramuscular, or intradermal injection. Such preparations may conveniently be prepared by admixing the OSGPR116 modulator with water and rendering the resulting solution sterile and isotonic with the blood. Injectable compositions according to the invention will generally contain from 0.1 to 5% w/w of the OSGPR116 modulator.

Formulations suitable for rectal administration are preferably presented as unit-dose suppositories. These may be prepared by admixing a OSGPR116 modulator with one or more conventional solid carriers, for example, cocoa butter, and then shaping the resulting mixture.

Formulations suitable for topical application to the skin preferably take the form of an ointment, cream, lotion, paste, gel, spray, aerosol, or oil. Carriers which may be used include vaseline, lanolin, polyethylene glycols, alcohols, and combinations of two or more thereof. The OSGPR116 modulator is generally present at a concentration of from 0.1 to 15% w/w of the composition, for example, from 0.5 to 2%.

Alternatively, agents which up-regulate OSGPR116 expression or nucleic acids encoding OSGPR116 or a variant polypeptide may be administered to the mammal. Nucleic acid, such as RNA or DNA, preferably DNA, is provided in the form of a vector, which may be expressed in the cells of a human or other mammal under treatment. Preferably such up-regulation or expression following nucleic acid administration will enhance OSGPR116 activity.

OSGPR116 antisense nucleic acid or RNAi may also be used to decrease OSGPR116 protein level and thus OSGPR116 activity, for use in feeding disorders requiring appetite stimulation, or other OSGPR166 mediated diseases that would benefit from a decrease in OSGPR116 activity.

Nucleic acid encoding OSGPR116 or variant polypeptide may be administered to a human or other mammal by any available technique. For example, the nucleic acid may be introduced by injection, preferably intradermally, subcutaneously or intramuscularly. Alternatively, the nucleic acid may be delivered directly across the skin using a nucleic acid delivery device such as particle-mediated gene delivery. The nucleic acid may be administered topically to the skin, or to the mucosal surfaces for example by intranasal, oral, intravaginal, intrarectal administration.

Uptake of nucleic acid constructs may be enhanced by several known transfection techniques, for example those including the use of transfection agents. Examples of these agents includes cationic agents, for example, calcium phosphate and DEAE-dextran and lipofectants, for example, lipofectam and transfectam. The dosage of the nucleic acid to be administered can be altered. Typically the nucleic acid is administered in the range of 1 pg to 1 mg, preferably to 1 pg to 10 µg nucleic acid for particle mediated gene delivery and 10 µg to 1 mg for other routes.

Polynucleotides encoding OSGPR116 or a variant polypeptide can also be used to identify mutation(s) in OSGPR116 genes which may be implicated in human disorders. Identification of such mutation(s) may be used to assist in diagnosis of feeding disorders and conditions associated with feeding disorders such as obesity, type II diabetes, insulin resistance and metabolic syndrome (syndrome X), or susceptibility to such disorders and in assessing the physiology of such disorders.

Antibodies (either polyclonal or preferably monoclonal antibodies, chimeric, single chain, Fab fragments) which are specific for the OSGPR116 polypeptides or a variant thereof can be generated. Such antibodies may for example be useful in purification, isolation or screening methods involving immunoprecipitation techniques and may be used as tools to elucidate further the function of OSGPR116 or a variant thereof, or indeed as therapeutic agents in their own right. Such antibodies may be used to block ligand binding to the receptors. A variety of protocols for competitive binding or immunoradiometric assays to determine the specific binding capability of an antibody are well known in the art (see for example Maddox et. al, J. Exp. Med. 158: 1211, 1993).

The activators, inhibitors, polynucleotides and antibodies for use in the instant invention may be used in combination with one or more other therapeutic agents. For example, in the treatment of a feeding disorder (overeating) or obesity, Orlistat, Sibutramine, or a cannabinoid CB1 receptor antagonist may be used in combination with an OSGPR116 receptor activator. The invention thus provides in a further aspect the use of a combination of a OSGPR116 modulator and at least one other therapeutic agent in the treatment of OSGPR116 mediated disorders.

When the activators, inhibitors and polynucleotides and antibodies are used in combination with other therapeutic agents, the agents may be administered either sequentially or simultaneously by any convenient route.

The combinations referred to above may conveniently be presented for use in the form of a pharmaceutical formulation and thus pharmaceutical formulations comprising a combination as defined above optimally together with a pharmaceutically acceptable carrier or excipient comprise a further aspect of the invention. The individual components of such combinations may be administered either sequentially or simultaneously in separate or combined pharmaceutical formulations.

When combined in the same formulation it will be appreciated that the two components must be stable and compatible with each other and the other components of the formulation and may be formulated for administration. When formulated separately they may be provided in any convenient formulation, conveniently in such a manner as are known for such compounds in the art.

When in combination with a second therapeutic agent active against the same disease, the dose of each component may differ from that when the compound is used alone. Appropriate doses will be readily appreciated by those skilled in the art.

Compounds of the invention that are identified as modulators of OSGPR116 activity can be screened by a variety of means known in the art to demonstrate their pharmacological activity. Body fat reducing compounds, for instance, can be identified in vivo using animal bioassay techniques known to those of ordinary skill in the art. Test compounds and appropriate vehicle or caloric controls can be administered by any of a number of routes (e.g., the oral route, a parenteral route) to experimental subjects and the weight of the subjects can be monitored over the course of therapy. The experimental subjects are humans or test animals (e.g., rats, mice).

The effect of the compound on appetite or in inducing hypophagia or reduced food intake can be assessed, for instance, by monitoring the food consumption of the test subjects (e.g., measuring the amount eaten or not eaten by a subject in terms of food weight or caloric content). The effect of the compounds on appetite can also be assessed by subjective means including questionnaires as to appetite or food cravings levels by human subjects. The effect of the test compounds on lipid metabolism can be assessed by monitoring blood lipids and fatty acid oxidation. The techniques for these assessments are well known to those of ordinary skill in the art. The studies may be acute, subacute, chronic, or subchronic with respect to the duration of administration and or follow-up of the effects of the administration.

Body fat reduction can be determined, for instance, by directly measuring changes in body fat of the animal or by measuring changes in the body weight of the animal. The animal may be selected from the group consisting of a mouse, a rat, a guinea pig, or a rabbit. The animal may also be an ob/ob mouse, a db/db mouse, or a Zucker rat or other animal model for a weight-associated disease. Clinical studies in humans may also be conducted.

Compounds of the invention can be administered to an animal to determine whether they affect food intake and body weight, body fat, appetite, food seeking behavior, or modulate fatty acid oxidation. Animals can be, for example, obese or normal guinea pigs, rats, mice, or rabbits. Suitable rats include, for example, Zucker rats. Suitable mice include, for example, normal mice, ALS/LtJ, C3.SW-H-$2^b$/Snj, (NON/LtJ×NZO/H1J)F1, NZO/H1J, ALR/LtJ, NON/LtJ, KK.Cg-AALR/LtJ, NON/LtJ, KK.Cg-A$^Y$/J, B6.HRS(BKS)-Cpe$^{fat}$/+, B6.129P2-Gck$^{tm/Efr}$, B6.V-Lep$^{ob}$, BKS.Cg-m+/+ Lep$^{rd}$b, and C57BL/6J with diet induced obesity.

Administration of an appropriate amount the candidate compound may be by any means known in the art such as, for example, oral or rectal, parenteral such as, for example, intraperitoneal, intravenous, subcutaneous, subdermal, intranasal, or intramuscular. Preferably administration may be intraperitoneal or oral. An appropriate effective amount of the candidate compound may be determined empirically as is known in the art. An appropriate effective amount may be an amount sufficient to effect a loss of body fat or a loss in body weight or reduction in food consumption in the animal over time. The candidate compound can be administered as often as required to effect a loss of body fat or loss in body weight, for example, hourly, every six, eight, twelve, or eighteen hours, daily, or weekly. Formulations suitable for oral administration include (a) liquid solutions, such as an effective amount of the candidate compound suspended in diluents, such as water, saline or PEG 400; (b) capsules, sachets or tablets, each containing a predetermined amount of the active ingredient, as liquids, solids, granules or gelatin; (c) suspensions in an appropriate liquid; and (d) suitable emulsions. Tablet forms include one or more of lactose, sucrose, mannitol, sorbitol, calcium phosphates, corn starch, potato starch, microcrystalline cellulose, gelatin, colloidal silicon dioxide, talc, magnesium stearate, stearic acid, and other excipients, colorants, fillers, binders, diluents, buffering agents, moistening agents, preservatives, flavoring agents, dyes, disintegrating agents, and pharmaceutically compatible carriers. Lozenge forms can comprise the active ingredient in a flavor, e.g., sucrose, as well as pastilles comprising the active ingredient in an inert base, such as gelatin and glycerin or sucrose and acacia emulsions, gels, and the like containing, in addition to the active ingredient, carriers known in the art.

Injection, solutions, and suspensions, can be prepared from sterile powders, granules, and tablets of the kind previously described. Formulations suitable for parenteral administration, include, for example, aqueous and non-aqueous, isotonic sterile injection solutions, which can contain antioxidants, buffers, bacteriostats, and solutes that render the formulation isotonic with the blood of the intended recipient, and aqueous and non-aqueous sterile suspensions that can include suspending agents, solubilizers, thickening agents, stabilizers, and preservatives.

The dose administered to the animal is sufficient to effect a change in body weight, body fat, and/or fatty acid oxidation over time. Such a dose can be determined according to the efficacy of the particular candidate compound employed and the condition of the animal, as well as the body weight or surface area of the animal. The size of the dose also will be determined by the existence, nature, and extent of any adverse side-effects that accompany the administration of a candidate compound; the $LD_{50}$ of the candidate compound; and the side-effects of the candidate compound at various concentrations. In general, the dose will range from 0.1–50 mg per kg, preferably 1–25 mg per kg, most preferably 1–20 mg per kg body weight. The determination of dose response relationships is well known to one of ordinary skill in the art.

Body weight reduction is typically determined by direct measurements of the change in body fat or by loss of body weight. Body fat and body weight of the animals is determined before, during, and after the administration of the candidate compound. Changes in body fat are measured by any means known in the art such as, for example, fat fold measurements with calipers, bioelectrical impedance, hydrostatic weighing, or dual x-ray absorbiometry (e.g-.DEXA). Preferably animals demonstrate at least 2%, 5%, 8%, or 10% loss of body fat. Changes in body weight can be measured by any means known in the art such as, for example, on a portable scale, on a digital scale, on a balance scale, on a floor scale, or a table scale. Preferably animals demonstrate at least 2%, 5%, 10%, or 15% loss of body weight. Body weight reduction is measured before administration of the candidate compound and at regular intervals during and after treatment. Preferably, body weight is measured every 5 days, more preferably every 4 days, even more preferably every 3 days, yet more preferably every 2 days, most preferably every day.

Changes in fatty acid metabolism can be measured by looking at fatty acid oxidation in cells from major fat burning tissues such as, for example, liver (Beynen, et al. Diabetes 28:828 (1979)), muscle (Chiasson Lab. Anat. of Rat, (1980)), heart (Flink, et al. J Biol. Chem. 267: 9917 (1992)), and adipocytes (Rodbell, J. Biol. Chem. 239: 375 (1964)), Cells may be from primary cultures or from cell lines. Cells may be prepared for primary cultures by any means known in the art including, for example, enzymatic digestion and dissection. Suitable cell lines are known to those in the art. Suitable hepatocyte lines are, for example, Fao, MH1C1, H-4-II-E, H4TG, H-4-II-E-C3, McA-RH7777, McA-RH8994, N I-S1 Fudr, N1-S1, ARL-6, Hepa 1–6, Hepa-1c1c7, BpRc1, tao BpRc1, NCTC clone 1469, PLC/PRF/5, Hep 3B2.1-7 [Hep 3B], Hep G2 [HepG2], SK-HEP-1, and WCH-17. Suitable skeletal muscle cell lines are, for example, L6, L8, C8, NOR-10, BLO-11, BC3H1, G-7, G-8, C2C12, P19, Sol8, SJRH30 [RMS 13], and QM7. Suitable cardiac cell lines are, for example, H9c2(2-1), P19, CCD-32Lu, CCD-32Sk, Girardi, and FBHE. Suitable adipocyte lines are, for example, NCTC clone 929 [derivative of Strain L; L-929; L cell], NCTC 2071, L-M, L-M(TK-) [LMTK-; LM(tk-)], A9 (APRT and HPRT negative derivative of Strain L), NCTC clone 2472, NCTC clone 2555, 3T3-L1, J26, J27-neo, J27-B7, MTKP 97-12 pMp97b [TKMp97-12], L-NGC-5HT2, Ltk-11, L-alpha-1b, L-alpha-2A, L-alpha-K, and B82.

The rate of fatty acid oxidation may be measured by $^{14}C$-oleate oxidation to ketone bodies (Guzman and Geelen, Biochem. J. 287:487 (1982)) and/or $^{14}C$-oleate oxidation to $CO_2$ (Fruebis, PNAS 98:2005 (2001); Blazquez et. al., J Neurochem 71:1597 (1998)). Lipolysis may be measured by fatty acid or glycerol release by using appropriate labeled precursors or spectrophotometric assays (Serradeil-Le Gal, FEBS Lett., 475:150 (2000)). For analysis of $^{14}C$-oleate oxidation to ketone bodies, freshly isolated cells or cultured cell lines can be incubated with $^{14}C$-oleic acid for an appropriate time, such as, for example, 30, 60, 90, 120, or 180 minutes. The amount of $^{14}C$ radioactivity in the incubation medium can be measured to determine their rate of oleate oxidation. Oleate oxidation can be expressed as nmol oleate produced in x minutes per g cells. For analysis of lypolysis/glycerol release, freshly isolated cells or cultured cells lines can be washed then incubated for an appropriate time. The amount of glycerol released into the incubation media can provide an index for lipolysis.

Many alternative experimental methods known in the art may be successfully substituted for those specifically described herein in the practice of this invention, as for example described in many of the excellent manuals and textbooks available in the areas of technology relevant to this invention (e.g. Using Antibodies, A Laboratory Manual, edited by Harlow, E. and Lane, D., 1999, Cold Spring Harbor Laboratory Press, (e.g. ISBN 0-87969-544-7); Roe B. A. et. al. 1996, DNA Isolation and Sequencing (Essential Techniques Series), John Wiley & Sons.(e.g. ISBN 0-471-97324-0); Methods in Enzymology: Chimeric Genes and Proteins", 2000, ed. J. Abelson, M. Simon, S. Emr, J. Thorner. Academic Press; Molecular Cloning: a Laboratory Manual, 2001, $3^{rd}$ Edition, by Joseph Sambrook and Peter MacCallum, (the former Maniatis Cloning manual) (e.g. ISBN 0-87969-577-3); Current Protocols in Molecular Biology, Ed. Fred M. Ausubel, et. al. John Wiley & Sons (e.g. ISBN 0-471-50338-X); Current Protocols in Protein Science, Ed. John E. Coligan, John Wiley & Sons (e.g. ISBN 0-471-11184-8); and Methods in Enzymology: Guide to protein Purification, 1990, Vol. 182, Ed. Deutscher, M. P., Academic Press, Inc. (e.g. ISBN 0-12-213585-7)), or as described in the many university and commercial websites devoted to describing experimental methods in molecular biology.

This invention will be better understood from the Experimental Details which follow. However, one skilled in the art will readily appreciate that the specific methods and results discussed are merely illustrative of the invention as described more fully in the claims which follow thereafter, and are not to be considered in any way limited thereto.

EXPERIMENTAL DETAILS

Materials and Methods
Lipid Compounds
All fatty acid amide compounds were purchased from Cayman Chemical Co., 1180 E Ellsworth Rd, Ann Arbor Mich., 48108, or synthesized by methods known in the art (e.g. see WO 02/080860, and references cited therein, for synthesis of the same or similar compounds).

Cell Lines and Reagents
Cell lines were purchased from the American Type Culture Collection and maintained in a suitable growth medium (e.g. DMEM) supplemented with Fetal Bovine Serum (e.g. 10% FBS). pcDNA 3.1 mammalian expression vector, PCR Blunt cloning vector, and DH5α competent *E. coli* cells were purchased from Invitrogen Life Corporation. PCR reagents were from Roche Molecular Systems, Inc. (N808-0228). Restriction endonucleases were from New England Biolabs, Inc. The primers used for PCR were synthesized by ACGT, Inc. Transfection reagents were purchased from Roche.

Cloning of Human and Mouse OSGPR116 Receptors

The OSGPR116 human and mouse genes are single exon genes of approximately 1.0 kilobase pairs in length with a 54.7% and 51.4% GC content respectively.

The mouse receptor gene was PCR amplified from 0.1 µg mouse genomic DNA in a 25 µL reaction volume using the appropriate oligonucleotides m116FBsmBI and m116RXbaI (see FIG. 5) at 0.5 uM each, 0.5 mM dNTP mix, 1.5×Pfu buffer, and 2.5 units Pfu-turbo enzyme (Stratagene). PCR cycling conditions were set as follows: 2 minute hold at 95° C.; 35 cycles of template denaturing, 15 seconds at 95° C., primer annealing 30 seconds at 55° C., primer extension 1 minute 30 seconds at 72° C.; 7 minute hold at 72° C.; final hold at 4° C. PCR DNA was purified from PCR reaction mix according to QIAGEN's QIAquick PCR purification spin column protocol.

Resulting DNA fragments were consecutively digested in a 100 µL final reaction volume with restriction enzyme BsmBI (1 unit/µg DNA) for 1 hour at 55° C., followed by a 1-hour digestion at 37° C. with XbaI (1 unit/µg DNA). The m116FBsmBI oligonucleotide was designed to create an NcoI restriction site when cut with BsmBI restriction enzyme. The NcoI site can be found at the receptor gene's ATG initiation codon. Following fragment digestion, DNA was gel purified from a 1.5% agarose gel using a QIAquick gel extraction protocol (QIAGEN).

The OSGPR116 gene was cloned into a yeast expression vector at the NcoI/XbaI restriction sites in a (cohesive) sticky-end ligation reaction. Ligation reactions were set up at a 3:1 insert to vector ratio using 25 ng digested parent yeast expression vector. The 20 ul reaction mix containing the DNA, 1× ligase buffer, and 20 units T4 DNA ligase, was incubated at room temperature for 1 hour. In the resulting construct, OSGPR116 expression is under the control of the PGK promoter while the N-terminus of the receptor gene is fused to an 89 amino acid Mfα1-Leader sequence. Mfα1 is responsible for transporting the receptor to the cell membrane and is crucial for the performance of the FUS1-LacZ yeast assay.

The receptor-vector was then transformed into TOP10 chemically competent *E. coli* cells (Invitrogen). Between 1 ul and 5 ul ligation reaction product was introduced to 50 µL cells and incubated on ice for 30 minutes. Cells were then heat shocked for 30 seconds at 42° C., followed by 1 hour incubation in 250 µL S.O.C. media at 37° C. with agitation (225 rpm). After the 1 hour growth period, cells were spread out on LB agar plates with ampicillin and incubated overnight at 37° C. *E. coli* transformants containing ampicillin resistance were picked the following day and set up for plasmid isolation according to QIAGEN's miniprep protocol. DNA was analyzed by restriction digest using enzyme combination BglII/BamHI. Miniprep DNA digests resulting in a 7.6 kb+1.2 kb banding pattern on an agarose gel confirmed which plasmids contained the OSGPR116 gene. Seventeen of twenty miniprep samples were reported positive. Sequencing analysis of several clones was conducted. In a BLAST pairwise sequence alignment, the resulting sequence data from two individual DNA preparations were found to be 100% identical with the mouse OSGPR116 sequence found in the literature.

A similar protocol was followed for cloning the human receptor gene into the yeast expression vector. PCR amplification of the human gene was accomplished using human genomic DNA and primers listed as OS116-BsaF1 and OSI 16-XbaR1 (see FIG. 5). Purified DNA fragments were digested with the restriction enzyme BsaI at 50° C. followed by digestion with XbaI at 37° C. As described earlier, the OS116-BsaF1 oligonucleotide was designed so that when used in fragment digestion, the enzyme would create the NcoI overhangs needed to clone into the yeast expression vector in-frame. DNA was gel purified and cloned into the yeast expression vector at the NcoI/XbaI restriction sites in a sticky-end ligation reaction. The resulting construct was later used as the DNA template in PCR amplification for cloning the human OSGPR116 gene into the mammalian expression vector pcDNA3.1(+)/Hygro. The gene was amplified in 25 PCR cycles using oligonucleotides: OS116-HindIIIF and OS116-XbaR1. Fragment ends were digested with HindIII and XbaI in order to create overhangs which would be consistent with the multiple cloning sites of pcDNA3.1.

The rat OSGPR116 receptor sequence has also been described (U.S. Pat. No. 6,221,660; U.S. Pat. No. 6,468,756), and can readily be cloned by comparable methods.

Host Cells for Expression of Recombinant OSGPR116

A broad variety of host cells can be used to study heterologously expressed proteins. These cells include but are not limited to mammalian cell lines such as; Cos-7, CHO, LM(tk-), HEK293, etc.; insect cell lines such as; Sf9, Sf21, etc.; amphibian cells such as *Xenopus* oocytes; assorted yeast strains; assorted bacterial cell strains; and others. Culture conditions for each of these cell types is specific and is known to those familiar with the art.

COS-7 cells are grown on 150 mm plates in DMEM with supplements (Dulbecco's Modified Eagle Medium with 10% bovine calf serum, 4 mM glutamine, 100 units/mL penicillin/100 µg/mL streptomycin) at 37° C., 5% $CO_2$. Stock plates of COS-7 cells are trypsinized and split 1:6 every 3–4 days.

CHO cells are grown on 150 mm plates in HAM's F-12 medium with supplements (10% bovine calf serum, 4 mM L-glutamine and 100 units/mL penicillin/100 µg/mL streptomycin) at 37° C., 5% CO2. Stock plates of CHO cells are trypsinized and split 1:8 every 3–4 days.

Transient Expression

DNA encoding proteins to be studied can be transiently expressed in a variety of mammalian, insect, amphibian, yeast, bacterial and other cell lines by several methods, such as, calcium phosphate-mediated, DEAE-dextran mediated, liposomal-mediated, viral-mediated, electroporation-mediated and microinjection delivery. Each of these methods may require optimization of assorted experimental parameters depending on the DNA, cell line, and the type of assay to be subsequently employed.

A typical protocol for the electroporation method as applied to Cos-7 cells is described as follows. Cells to be used for transfection are split 24 hours prior to the transfection to provide flasks which are subconfluent at the time of transfection. The cells are harvested by trypsinization resuspended in their growth media and counted. $5 \times 10^6$ cells are suspended in 300 µL of DMEM and placed into an electroporation cuvette. 8 µg of receptor DNA plus 8 µg of any additional DNA needed (e.g. G protein expression vector, reporter construct, antibiotic resistance marker, mock vector, etc.) is added to the cell suspension, the cuvette is placed into a BioRad Gene Pulser and subjected to an electrical pulse (Gene Pulser settings: 0.25 kV voltage, 950 µF capacitance). Following the pulse, 800 µL of complete DMEM is added to each cuvette and the suspension transferred to a sterile tube. Complete medium is added to each tube to bring the final cell concentration to $1\times10^5$ cells/100 µL. The cells are then plated as needed depending upon the type of assay to be performed.

Stable Expression

Heterologous DNA can be stably incorporated into host cells, causing the cell to perpetually express a foreign protein. Methods for the delivery of the DNA into the cell are similar to those described above for transient expression but require the co-transfection of an ancillary gene to confer drug resistance on the targeted host cell. The ensuing drug resistance can be exploited to select and maintain cells that have taken up the DNA. An assortment of resistance genes are available including but not restricted to neomycin, kanamycin, and hygromycin. For the purposes of studies concerning the receptor of this invention, stable expression of a heterologous receptor protein is typically carried out in, mammalian cells including but not necessarily restricted to, CHO, HEK293, LM(tk-), etc.

In addition native cell lines that naturally carry and express the nucleic acid sequences for the receptor may be used without the need to engineer the receptor complement.

Membrane Preparations

Cell membranes expressing the receptor protein according to this invention are useful for certain types of assays including but not restricted to ligand binding assays, GTP-γ-S binding assays, and others. The specifics of preparing such cell membranes may in some cases be determined by the nature of the ensuing assay but typically involve harvesting whole cells and disrupting the cell pellet by sonication in ice cold buffer (e.g. 20 mM Tris-HCl, 5 mM EDTA, pH 7.4). The resulting crude cell lysate is cleared of cell debris by low speed centrifugation at 200×g for 5 min at 4° C. The cleared supernatant is then centrifuged at 40,000×g for 20 min at 4° C., and the resulting membrane pellet is washed by suspending in ice cold buffer and repeating the high speed centrifugation step. The final washed membrane pellet is resuspended in assay buffer. Protein concentrations are determined by the method of Bradford (1976) using bovine serum albumin as a standard. The membranes may be used immediately or frozen for later use.

Alternatively, plasma membrane-containing P2 particulate fractions are readily prepared from cell pastes frozen at −80° C. after harvest. All procedures are carried out at 4° C. Cell pellets are resuspended in 1 mL of 10 mM Tris-HCl and 0.1 mM EDTA, pH 7.5 (buffer A) and by homogenisation for 20 s with a polytron homogeniser followed by passage (5 times) through a 25-guage needle. Cell lysates are centrifuged at 1,000 g for 10 min in a microcentrifuge to pellet the nuclei and unbroken cells and P2 particulate fractions are recovered by microcentrifugation at 16,000 g for 30 min. P2 particulate fractions are resuspended in buffer A and stored at −80° C. until required. Protein concentrations are determined using the bicinchoninic acid (BCA) procedure (Smith, P. K. et al. (1985) Analytical Biochemistry, 150: 76–85) using BSA as a standard.

Generation of Baculovirus

The coding region of DNA encoding the human receptor disclosed herein may be subcloned into pBlueBacIII into existing restriction sites or sites engineered into sequences 5' and 3' to the coding region of the polypeptides. To generate baculovirus, 0.5 µg of viral DNA (BaculoGold) and 3 µg of DNA construct encoding a polypeptide may be co-transfected into $2\times10^6$ *Spodoptera frugiperda* insect Sf9 cells by the calcium phosphate co-precipitation method, as outlined by Pharmingen (in "Baculovirus Expression Vector System: Procedures and Methods Manual"). The cells then are incubated for 5 days at 27° C.

The supernatant of the co-transfection plate may be collected by centrifugation and the recombinant virus plaque purified. The procedure to infect cells with virus, to prepare stocks of virus and to titer the virus stocks are as described in Pharmingen's manual.

Fluorogenic Expression Analysis of OSGPR116

Quantitative RT-PCR by the ABI Prism 7700 Sequence Detector (TaqMan) was used to determine tissue specific expression of OSGPR116 in a variety of human tissues and cell lines. Initially, RNA is isolated from these tissues according to Clontech's Nucleospin RNA II Protocol and kit for cultured cells. The cells are lysed using a kit buffer containing β-mercaptoethanol. The lysate is filtered and cleared using ethanol. The RNA in solution binds to provided nucleospin columns. Once bound to the column, the RNA is treated with a DNase, washed with buffers supplied in the kit, and eluted with nuclease-free water in RNase— free tubes. The RNA yield is estimated using UV spectrophotometry with a conversion of 1.0 A260 unit RNA=40 µg/mL.

1 µg RNA is used for first-strand cDNA synthesis with SUPERSCRIPT II (Invitrogen) in a final RT-PCR reaction volume of 20 ul. The initial 11 ul reaction mixture containing 0.5 µg oligo (dT)12–18, 1 µg RNA, and 500 µM dNTP mix, was heated to 65° C. for 5 minutes followed by a brief cooling on ice. This reaction volume was increased to 19 ul using 1× first-strand buffer, 0.01M DTT, and 40 units RNaseOUT-Ribonuclease Inhibitor (Ambion), and the reactions were heated to 42° C. for 2 minutes. Finally, 200 units SUPERSCRIPT II were added to the (+) reactions and water was added to the (−) No RT control reactions, making the final RT-PCR reaction volume 20 µL. The reactions were cycled once at 42° C. for 30 minutes, 45° C. for 15 minutes, 49° C. for 15 minutes, and 72° C. for 10 minutes. The total volume of the cDNA reaction was 20 µL containing 1 µg RNA starting material. This starting material was diluted 1:20 in the reaction mixture. Therefore, the theoretical cDNA yield was 50 ng/µL. Samples were diluted two-fold to titrate the theoretical yield to 25 ng/µL.

cDNA(+) and No RT control samples were plated in 96 well PCR plates (Applied Biosystems) (with optical caps) for TaqMan/expression profiling using the expression oligonucleotide listed. Amplification TaqMan mix includes 1×TaqMan Universal PCR Master Mix (Applied Biosystems), 0.9 µM primer, 0.3 µM TaqMan probe, and 25 ng cDNA sample, for a total reaction volume of 25 µL. The reactions are cycled 40 times at 50° C. for 2 minutes, 95° C. for 10 minutes, 95° C. for 15 seconds, and 60° C. for 1 minute. A control plate using TFIIB primers and probe was used to confirm the presence of cDNA in the (+) samples, as well as, the absence of cDNA in the No RT controls. TFIIB is a transcription factor expressed in all the cell types studied here. Therefore, TFIIB data is used for normalizing/standardizing expression data (Data are expressed as a ratio of gene expression/TFIIB expression).

The fluorogenic (TaqMan) probes are designed such that the oligonucleotide contains a 5'-reporter dye and a downstream, 3'-quencher dye. The reporter dye, such as FAM (6-carboxy-fluorescein), is a fluorescent dye linked to the 5' end of the nucleotide via a covalent bond. Located at the 3' end, TAMRA (6-carboxy-tetramethyl-rhodamine) is responsible for quenching the fluorescent reporter dye. This suppressive activity is due to the close proximity of the reporter dye and the quencher dye when the probe is intact. TaqMan probes are designed to hybridize to a sequence region internal to the target gene and no other gene (determined by BLAST analysis of designed oligonucleotide sequences). Gene-specific forward and reverse primers are also designed to hybridize the sequence regions flanking the probe hybridization sequence.

TaqMan PCR master mix contains AmpliTaq Gold polymerase. Because 5'-3' nuclease activity is characteristic of Taq polymerases, these polymerases have the ability to cleave nucleotides off the template DNA strand during 5' to 3' polymerization and amplification. Therefore, in a PCR reaction containing OS116-Tqn1 in addition to OSGPR116 forward and reverse primers, the OSGPR116 probe will be cleaved from the DNA template during OS 116-F1 primer extension (see FIG. 6). Upon cleavage of the 5' end of the probe, the reporter dye is released into solution and separated from the quencher dye. This results in the increase of reporter fluorescence during every PCR cycle. Therefore, the greater the fluorescence, the greater the amplification (and expression) of the target gene. The amount of fluorescence measured by the ABI Prism 7700 Sequence Detector is related to the amount of expressed OSGPR116 in genomic DNA equivalents.

TaqMan expression profiling was completed for OSGPR116 using Marathon-Ready cDNAs prepared from normal human tissues (Clontech), and in-house cDNAs made from tumor cell lines using the aforementioned protocols.

Yeast Assays

The yeast cell-based reporter assays have previously been described in the literature (e.g. see Miret J. J., et. al. (2002) J. Biol. Chem. 277:6881–6887; Campbell R. M., et. al. (1999) Bioorg Med. Chem. Lett. 9:2413–2418; King K., et. al. (1990) Science. 250:121–123); WO 99/14344; WO 00/12704; and U.S. Pat. No. 6,100,042). Briefly, yeast cells have been engineered such that the endogenous yeast G-alpha (GPA1) has been deleted and replaced with G-protein chimeras constructed using multiple techniques. Additionally the endogenous yeast alpha-cell GPCR, Ste3 has been deleted to allow for a homologous expression of a mammalian GPCR of choice. In the yeast, elements of the pheromone signaling transduction pathway, which are conserved in eukaryotic cells (for example, the mitogen-activated protein kinase pathway), drive the expression of Fus1. By placing β-galactosidase (LacZ) under the control of the Fus1 promoter (Fus1p), a system has been developed whereby receptor activation leads to an enzymatic read-out. Different yeast strains (e.g. FIG. 10) denote the presence of different G-alpha chimeras (see "yeast reporter assays" in Results section below for definitions).

Yeast cells are transformed by an adaptation of the Lithium acetate method described by Agatep et.al. (Agatep, R., et. al. (1998) Transformation of *Saccharomyces cerevisiae* by the lithium acetate/single-stranded carrier DNA/polyethylene glycol (LiAc/ss-DNA/PEG) protocol. Technical Tips Online, Trends Journals, Elsevier). Briefly, yeast cells are grown overnight on yeast tryptone plates (YT). Carrier single-stranded DNA (10 μg), 2 μg of each of two Fus1p-LacZ reporter plasmids (one with URA selection marker and one with TRP), 2 μg of OSGPR116 in yeast expression vector (2μ origin of replication) and a lithium acetate/polyethylene glycol/TE buffer is pipetted into an Epindorf tube. The yeast expression plasmid containing the receptor/no receptor control has a LEU marker. Yeast cells are inoculated into this mixture and the reaction proceeds at 30° C. for 60 minutes. The yeast cells are then heat-shocked at 42° C. for 15 minutes. The cells are then washed and spread on selection plates. The selection plates are synthetic defined yeast media minus LEU, URA and TRP (SD-LUT). After incubating at 30° C. for 2–3 days, colonies that grow on the selection plates are then tested in the LacZ assay.

In order to perform fluorometric enzyme assays for β-galactosidase, yeast cells were grown overnight in liquid SD-LUT media to an unsaturated concentration (i.e. the cells are still dividing and have not yet reached stationary phase). They are diluted in fresh media to an optimal assay concentration and 90 μL of yeast cells were added to 96-well black polystyrene plates (Costar). Compounds, dissolved in ethanol and diluted in a 1% BSA solution to 10× concentration, were added to the plates and the yeast are placed at 30° C. for 4h. After 4h, the substrate for the β-galactosidase is added to each well. The substrate may yield a fluorescent or calorimetric read-out upon the activity of the β-galactosidase. In these experiments, Fluorescein di (β-D-galactopyranoside) was used (FDG), a substrate for the enzyme that releases fluorescein, allowing a fluorometric read-out. 20 μL of 500 uM FDG was used. After incubation of the cells with the substrate for 30–60 mins, 20 μL of 1M sodium carbonate is added to terminate the reaction and enhance the fluorescent signal. The plates were then read in a fluorometer at 485/535 nm. As an alternate read-out system, the yeast are also engineered with a Fus1p-HIS gene which means that activation of the receptor can also be measured through the growth of the yeast in a Histamine deficient media.

Mammalian Assays

Adenylate Cyclase

The adenylate cyclase assay was performed with an alpha-screen cAMP assay kit (Promega). The manufacturers protocol was followed. Briefly, ASPC-1 cells, known to endogenously express moderate levels of OSGPR116 were lysed from the culture flask using a lysis buffer (0.1% BSA in PBS containing 20 μM rolipram and 0.54% TWEEN20), washed with PBS and diluted in assay buffer (0.1% BSA in PBS containing 20 μM rolipram) to a concentration of 600,000 cells/mL. White polystyrene 96-well plates were used for the assay. The following reagents were added to the wells, 5 μl forskolin (4× in assay buffer, $4 \times 10^{-4}$ M) or 5 ul assay buffer+5 μl Oleoylethanolamide/vehicle control (Oleoylethanolamide (4×) was dissolved in a 0.1% BSA in water solution)+5 μl acceptor beads (Stock solution was 90 μg/mL; 12 μl/0.5 mL stimulation buffer was used for the assay)+5 μl cells to initiate assay. The plate was incubated at room temperature 30 min. For the standard cAMP curve used to quantify the data, 5 μl water+5 μl 4×cAMP in assay buffer+5 μl acceptor beads+5 μl cells were added to the plate. To terminate the assay, 10 ul of the donor beads solution was added (30 nM biotin-cAMP/60 μg streptavidin-donor beads in 1 mL lysis buffer). The plates were incubated overnight, protected from light. A Fusion-αHT counter was used to read the plates according to the kit's instructions.

Cre-SEAP Assay

HEK-293—Galpha16 cells stably expressing the cre-SEAP (secreted alkaline phosphatase) reporter construct, and transiently transfected with either the OSGPR116 vector or empty vector control, were grown to between ~$0.5 \times 10^6$ and $1 \times 10^7$ cells/dish and seeded at $4 \times 10^4$ cells/well on poly-D-lysine coated clear-bottom 96-well tissue culture plates. The cells were left to adhere to the plates in media for 24h at 37° C. The media was aspirated and the cells arrested by serum starvation for a further 24h in 200 ul of colorless DMEM.

After serum arrest, the starvation media was aspirated and 90 ul fresh colorless DMEM containing 0.1% BSA was added. 10 ul of 10× compound (or DMSO/H$_2$0 control) was added and the plates incubated at 37° C. for 7h. Conditioned media (12.5 ul) was then transferred to a 96 well white flat-bottom plate. Next, 37.5 μl of 1× Tropix Dilution Buffer was added to the transferred culture media. 50 μl of Tropix Assay Buffer was also added. The plate was then incubated at room temperature for 5 minutes. Finally, 50 μl Tropix Reaction Buffer Diluent containing a 1:20 dilution of the CSPD Chemiluminescent Substrate was added. The plate was incubated at room temperature for 60 minutes and luminescence measured.

Melanophore Assays

Polypeptide of the invention can be heterologously expressed in *Xenopus laevis* melanophores and its activation can be measured by either melanosome dispersion or aggregation. Basically, melanosome dispersion is promoted by activation of adenylate cyclase or phospholipase C i.e. Gs and Gq mediated signalling, respectively, whereas aggregation results from activation of Gi/o G proteins resulting in inhibition of adenylate cyclase. Hence, ligand activation of the OSGPR116 can be measured simply by measuring the change in light transmittance through the cells or by imaging the cell response.

Assays for Compound Screening

OSGPR116 modulator activity can be determined by contacting cells expressing an OSGPR116 polypeptide of the invention with a substance under investigation and by monitoring the effect mediated by the polypeptides. The cells expressing the polypeptide may be in vitro or in vivo. The polypeptide of the invention may be naturally or recombinantly expressed. Preferably, the assay is carried out in vitro using cells expressing recombinant polypeptide. Typically, receptor activity can be monitored indirectly by measuring a Gi/o-coupled readout. Gi/o coupled readout can typically be monitored using an electrophysiological method to determine the activity of G-protein regulated $Ca^{2+}$ or $K^+$ channels or by using a fluorescent dye to measure changes in intracellular $Ca^{2+}$ levels. Other methods that can typically be used to monitor receptor activity involve measuring levels of or activity of labeled bound GTPγS or cAMP.

Preferably, control experiments are carried out on cells which do not express the polypeptide of the invention to establish whether the observed responses are the result of activation of the polypeptide.

Mammalian cells, such as HEK293, CHO and COS7 cells over-expressing the protein of choice are generated for use in the assay. Cell lines which maybe employed as suitable hosts include i) CHO cells transfected to stably express PLC 2, a PLC isoform which allows Gi/o G proteins to elicit $Ca^{2+}$ mobilization, or ii) CHO cells transfected to stably express the Gq family G-protein $G_{16}$ together with a suitable reporter gene e.g. NFAT (nuclear factor activator of T cells). Expression of $G_{16}$ permits a wide variety of non-Gq coupled receptors to mobilize $Ca^{2+}$.

96 and 384 well plate high throughput screens (HTS) are employed using a) fluorescence based calcium indicator molecules, including but not limited to dyes such as Fura-2, Fura-Red, Fluo 3 and Fluo 4 (Molecular Probes); or b) reporter gene read-out. Secondary screening involves the same technology. A brief screening assay protocol is as follows:—

Mammalian cells stably over-expressing the protein are cultured in black wall, clear bottom, tissue culture coated 96 or 384 well plates with a volume of 100 μL cell culture medium in each well 3 days before use in a FLIPR (Fluo-rescence Imaging Plate Reader—Molecular Devices). Cells were incubated with 4 μM Fluo-3 at 30° C. in 5% $CO_2$ for 90 mins and then washed once in Tyrodes buffer containing 3 mM probenecid. Basal fluorescence is determined prior to compound additions. Activation results in an increase in intracellular calcium which can be measured directly in the FLIPR.

The binding of a modulator to a polypeptide of the invention can also be determined directly. For example, a radiolabeled test substance can be incubated with the polypeptide of the invention and binding of the test substance to the polypeptide can be monitored. Typically, the radiolabeled test substance can be incubated with cell membranes containing the polypeptide until equilibrium is reached. The membranes can then be separated from a non-bound test substance and dissolved in scintillation fluid to allow the radioactive content to be determined by scintillation counting. Non-specific binding of the test substance may also be determined by repeating the experiment in the presence of a saturating concentration of a non-radioactive ligand.

Labeled Ligand Binding Assays

Cells expressing the receptor according to this invention may be used to screen for ligands for said receptors, for example, by labeled ligand binding assays. Once a ligand is identified the same assays may be used to identify agonists or antagonists of the receptor that may be employed for a variety of therapeutic purposes.

In an embodiment, labeled ligands are placed in contact with either membrane preparations or intact cells expressing the receptor in multi-well microtiter plates, together with unlabeled compounds, and binding buffer. Binding reaction mixtures are incubated for times and temperatures determined to be optimal in separate equilibrium binding assays. The reaction is stopped by filtration through GF/B filters, using a cell harvester, or by directly measuring the bound ligand. If the ligand was labeled with a radioactive isotope such as $^3H$, $^{14}C$, $^{125}I$, $^{35}S$, $^{32}P$, $^{33}P$, etc., the bound ligand may be detected by using liquid scintillation counting, scintillation proximity, or any other method of detection for radioactive isotopes. If the ligand was labeled with a fluorescent compound, the bound labeled ligand may be measured by methods such as, but not restricted to, fluorescence intensity, time resolved fluorescence, fluorescence polarization, fluorescence transfer, or fluorescence correlation spectroscopy. In this manner agonist or antagonist compounds that bind to the receptor may be identified as they inhibit the binding of the labeled ligand to the membrane protein or intact cells expressing the receptor. Non-specific binding is defined as the amount of labeled ligand remaining after incubation of membrane protein in the presence of a high concentration (e.g., 100–1000×$K_D$) of unlabeled ligand. In equilibrium saturation binding assays membrane preparations or intact cells transfected with the receptor are incubated in the presence of increasing concentrations of the labeled compound to determine the binding affinity of the labeled ligand. The binding affinities of unlabeled compounds may be determined in equilibrium competition binding assays, using a fixed concentration of labeled compound in the presence of varying concentrations of the displacing ligands.

Functional Assays

Cells expressing the OSGPR116 receptor DNA may be used to screen for ligands to OSGPR116 receptor using functional assays. Once a ligand is identified the same assays may be used to identify agonists or antagonists of the OSGPR116 receptor that may be employed for a variety of therapeutic purposes. It is well known to those in the art that the over-expression of a GPCR can result in the constitutive activation of intracellular signaling pathways. In the same manner, over-expression of the OSGPR116 receptor in any cell line as described above, can result in the activation of the functional responses described below, and any of the assays herein described can be used to screen for both agonist and antagonist ligands of the OSGPR116 receptor.

A wide spectrum of assays can be employed to screen for the presence of OSGPR116 receptor ligands. These assays range from traditional measurements of total inositol phosphate accumulation, cAMP levels, intracellular calcium mobilization, and potassium currents, for example; to systems measuring these same second messengers but which have been modified or adapted to be of higher throughput, more generic and more sensitive; to cell based assays reporting more general cellular events resulting from receptor activation such as metabolic changes, differentiation, cell division/proliferation. Description of several such assays follow.

Cyclic AMP (cAMP) Assay

The receptor-mediated stimulation or inhibition of cyclic AMP (cAMP) formation may be assayed in cells expressing the receptors. According to one method, cells are plated in 96-well plates or other vessels and preincubated in a buffer such as HEPES buffered saline (NaCl (150 mM), $CaCl_2$ (1 mM), KCl (5 mM), glucose (10 mM)) supplemented with a phosphodiesterase inhibitor such as 5 mM theophylline, with or without protease inhibitor cocktail (For example, a typical inhibitor cocktail contains 2 μg/mL aprotinin, 0.5 mg/mL leupeptin, and 10 μg/mL phosphoramidon.) for 20 min at 37° C., in 5% $CO_2$. Test compounds are added with or without 10 mM forskolin and incubated for an additional 10 min at 37° C. The medium is then aspirated and the reaction stopped by the addition of 100 mM HCl or other methods. The plates are stored at 4° C. for 15 min, and the cAMP content in the stopping solution is measured by radioimmunoassay. Radioactivity may be quantified using a gamma counter equipped with data reduction software. Specific modifications may be performed to optimize the assay for the receptor or to alter the detection method of cAMP.

According to a second method, cells are washed 2 times with HEPES buffered saline, as described above, and incubated overnight. On the day of the experiment, cells are washed 2 times with HEPES supplemented with a phosphodiesterase inhibitor such as 5 mM theophylline, with or without protease inhibitor cocktail (For example, a typical inhibitor cocktail contains 2 μg/mL aprotinin, 0.5 mg/mL leupeptin, and 10 μg/mL phosphoramidon.) for 20 min at 37° C., in 5% $CO_2$. Test compounds are added with or without 10 mM forskolin and incubated for an additional 10 min at 37° C. The medium is then aspirated and the reaction stopped by the addition of 100 mM HCl or other methods. The plates are stored at 4° C. for 15 min, and the cAMP content in the stopping solution is measured by radioimmunoassay. Radioactivity may be quantified using a gamma counter equipped with data reduction software. Specific modifications may be performed to optimize the assay for the receptor or to alter the detection method of cAMP.

Arachidonic Acid Release Assay

Cells expressing the receptor are seeded into 96 well plates or other vessels and grown for 3 days in medium with supplements $^3$H-arachidonic acid (specific activity=0.75 μCi/mL) is delivered as a 100 μL aliquot to each well and samples are incubated at 37° C., 5% $CO_2$ for 18 hours. The labeled cells are washed three times with medium. The wells are then filled with medium and the assay is initiated with the addition of test compounds or buffer in a total volume of 250 μL. Cells are incubated for 30 min at 37° C., 5% $CO_2$. Supernatants are transferred to a microtiter plate and evaporated to dryness at 75° C. in a vacuum oven. Samples are then dissolved and resuspended in 25 μL distilled water. Scintillant (300 μL) is added to each well and samples are counted for $^3$H in a Trilux plate reader. Data are analyzed using nonlinear regression and statistical techniques available in the GraphPAD Prism package (San Diego, Calif.).

Inositol Phosphate Assay

OSGPR116 receptor-mediated activation of the inositol phosphate (IP) second messenger pathways can be assessed by radiometric measurement of IP products.

In a 96 well microplate format assay, cells are plated at a density of 70,000 cells per well and allowed to incubate for 24 hours. The cells are then labeled with 0.5 μCi [$^3$H]-myo-inositol overnight at 37° C., 5% $CO_2$. Immediately before the assay, the medium is removed and replaced with 90 μL of PBS containing 10 mM LiCl. The plates are then incubated for 15 min at 37° C., 5% $CO_2$. Following the incubation, the cells are challenged with agonist (10 μL/well; 10× concentration) for 30 min at 37° C., 5% $CO_2$. The challenge is terminated by the addition of 100 μL of 50% v/v trichloroacetic acid, followed by incubation at 4° C. for greater than 30 minutes. Total IPs are isolated from the lysate by ion exchange chromatography. Briefly, the lysed contents of the wells are transferred to a Multiscreen HV filter plate (Millipore) containing Dowex AG1-X8 (200–400 mesh, formate form). The filter plates are prepared adding 100 μL of Dowex AG1-X8 suspension (50% v/v, water: resin) to each well. The filter plates are placed on a vacuum manifold to wash or elute the resin bed. Each well is first washed 2 times with 200 μL of 5 mM myo-inositol. Total [$^3$H]inositol phosphates are eluted with 75 μL of 1.2M ammonium formate/0.1M formic acid solution into 96-well plates. 200 μL of scintillation cocktail is added to each well, and the radioactivity is determined by liquid scintillation counting.

Intracellular Calcium Mobilization Assays

The intracellular free calcium concentration may be measured by microspectrofluorimetry using the fluorescent indicator dye Fura-2/AM (Bush et. al., (1991) J. Neurochem. 57: 562–574). Cells expressing the receptor are seeded onto a 35 mm culture dish containing a glass coverslip insert and allowed to adhere overnight. Cells are then washed with HBS and loaded with 100 μL of Fura-2/AM (10 μM) for 20 to 40 min. After washing with HBS to remove the Fura-2/AM solution, cells are equilibrated in HBS for 10 to 20 min. Cells are then visualized under the 40× objective of a Leitz Fluovert FS microscope and fluorescence emission is determined at 510 nM with excitation wavelengths alternating between 340 nM and 380 nM. Raw fluorescence data are converted to calcium concentrations using standard calcium concentration curves and software analysis techniques.

In another method, the measurement of intracellular calcium can also be performed on a 96-well (or higher) format and with alternative calcium-sensitive indicators, preferred examples of these are: aequorin, Fluo-3, Fluo-4, Fluo-5, Calcium Green-1, Oregon Green, and 488 BAPTA. After activation of the receptors with agonist ligands the emission elicited by the change of intracellular calcium concentration can be measured by a luminometer, or a fluorescence imager; a preferred example of this is the fluorescence imager plate reader (FLIPR).

Cells expressing the receptor of interest are plated into clear, flat-bottom, black-wall 96-well plates (Costar) at a density of 80,000–150,000 cells per well and allowed to incubate for 48 hr at 5% $CO_2$, 37° C. The growth medium is aspirated and 100 μL of loading medium containing fluo-3 dye is added to each well. The loading medium contains: Hank's BSS (without phenol red)(Gibco), 20 mM HEPES (Sigma), 0.1 or 1% BSA (Sigma), dye/pluronic acid mixture (e.g. 1 mM Flou-3, AM (Molecular Probes) and 10% pluronic acid (Molecular Probes) mixed immediately before use), and 2.5 mM probenecid (Sigma)(prepared fresh). The cells are allowed to incubate for about 1 hour at 5% $CO_2$, 37° C.

During the dye loading incubation the compound plate is prepared. The compounds are diluted in wash buffer (Hank's BSS (without phenol red), 20 mM HEPES, 2.5 mM probenecid) to a 4× final concentration and aliquoted into a clear v-bottom plate (Nunc). Following the incubation the cells are washed to remove the excess dye. A Denley plate washer is used to gently wash the cells 4 times and leave a 100 μL final volume of wash buffer in each well. The cell plate is placed in the center tray and the compound plate is placed in the right tray of the FLIPR. The FLIPR software is setup for the experiment, the experiment is run and the data are collected. The data are then analyzed using an excel spreadsheet program.

Antagonist ligands are identified by the inhibition of the signal elicited by agonist ligands.

GTPγS Functional Assay

Membranes from cells expressing the receptor are suspended in assay buffer (e.g., 50 mM Tris, 100 mM NaCl, 5 mM $MgCl_2$, 10 μM GDP, pH 7.4) with or without protease inhibitors (e.g., 0.1% bacitracin). Membranes are incubated on ice for 20 minutes, transferred to a 96-well Millipore microtiter GF/C filter plate and mixed with GTP.$\gamma^{35}$S (e.g., 250,000 cpm/sample, specific activity .about.1000 Ci/mmol) plus or minus unlabeled GTPγS (final concentration=100 μM). Final membrane protein concentration.apprxeq.90 μg/mL. Samples are incubated in the presence or absence of test compounds for 30 min. at room temperature, then filtered on a Millipore vacuum manifold and washed three times with cold (4° C.) assay buffer. Samples collected in the filter plate are treated with scintillant and counted for $^{35}$S in a Trilux (Wallac) liquid scintillation counter. It is expected that optimal results are obtained when the receptor membrane preparation is derived from an appropriately engineered heterologous expression system, i.e., an expression system resulting in high levels of expression of the receptor and/or expressing G-proteins having high turnover rates (for the exchange of GDP for GTP). GTPγS assays are well-known to those skilled in the art, and it is contemplated that variations on the method described above, such as are described by Tian et al. (1994) Molecular Pharm. 45: 524–553 or Lazareno and Birdsall (1993) Br. J. Pharmacol. 109: 1120–1127, may be used.

Alternatively, high affinity [$^{35}$S]-GTPγS binding assays are performed in 96-well format using a method modified from Wieland and Jakobs (Wieland, T. & Jakobs, K. H. (1994) Method. Enzymol. 237: 3–13). Membranes (10 μg per point) are diluted to about 0.1 mg/mL in assay buffer (20 mM HEPES, 100 mM NaCl, 10 mM $MgCl_2$, pH7.4) supplemented with saponin (10 mg/l) and pre-incubated with 40 μM GDP. Various concentrations of ligand (e.g. oleoyl ethanolamide) are added, followed by [$^{35}$S]-GTPγS (~1200 Ci/mmol, Amersham) at 0.3 nM (total vol. of 100 [d) and binding is allowed to proceed at room temperature for 30 min. Non-specific binding is determined by the inclusion of 0.6 mM GTP. Wheatgerm agglutinin SPA beads (Amersham; 0.5 mg) in 25 μL assay buffer are added and the whole is incubated at room temperature for 30 min with agitation. Plates are centrifuged at 1500 g for 5 min and bound [$^{35}$S]-GTPγS is determined by scintillation counting.

Alternatively, instead of [$^{35}$S]-GTPγS, a time-resolved fluorescence based GTP binding assay using a non-radioactive, non-hydrolyzable GTP analog such as GTP-Eu (Perkin Elmer™) can be employed.

Microphysiometric Assay

Because cellular metabolism is intricately involved in a broad range of cellular events (including receptor activation of multiple messenger pathways), the use of microphysiometric measurements of cell metabolism can in principle provide a generic assay of cellular activity arising from the activation of any receptor regardless of the specifics of the receptor's signaling pathway (Williams, C. (2000) Current Opinion Biotech. 11:42–46).

General guidelines for transient receptor expression, cell preparation and microphysiometric recording are described elsewhere (Salon, J. A. and Owicki, J. A., (1996) Meth. Neurosci. 25: 201–224). Typically cells expressing receptors are harvested and seeded at $3 \times 10^5$ cells per microphysiometer capsule in complete media 24 hours prior to an experiment. The media is replaced with serum free media 16 hours prior to recording to minimize non-specific metabolic stimulation by assorted and ill-defined serum factors. On the day of the experiment the cell capsules are transferred to the microphysiometer and allowed to equilibrate in recording media (low buffer RPMI 1640, no bicarbonate, no serum (Molecular Devices Corporation, Sunnyvale, Calif.) containing 0.1% fatty acid free BSA), during which a baseline measurement of basal metabolic activity is established.

A standard recording protocol specifies a 100 μL/min flow rate, with a 2 min total pump cycle which includes a 30 sec flow interruption during which the acidification rate measurement is taken. Ligand challenges involve a 1 min 20 sec exposure to the sample just prior to the first post challenge rate measurement being taken, followed by two additional pump cycles for a total of 5 min 20 sec sample exposure. Typically, drugs in a primary screen are presented to the cells at 10 μM final concentration. Follow up experiments to examine dose-dependency of active compounds are then done by sequentially challenging the cells with a drug concentration range that exceeds the amount needed to generate responses ranging from threshold to maximal levels. Ligand samples are then washed out and the acidification rates reported are expressed as a percentage increase of the peak response over the baseline rate observed just prior to challenge.

MAP Kinase Assay

MAP kinase (mitogen activated kinase) may be monitored to evaluate receptor activation. MAP kinase is activated by multiple pathways in the cell. A primary mode of activation involves the ras/raf/MEK/MAP kinase pathway. Growth factor (tyrosine kinase) receptors feed into this pathway via SHC/Grb-2/SOS/ras. Gi coupled receptors are also known to activate ras and subsequently produce an activation of MAP kinase. Receptors that activate phospholipase C (such as Gq/G11-coupled) produce diacylglycerol (DAG) as a consequence of phosphatidyl inositol hydrolysis. DAG activates protein kinase C which in turn phosphorylates MAP kinase.

MAP kinase activation can be detected by several approaches. One approach is based on an evaluation of the phosphorylation state, either unphosphorylated (inactive) or phosphorylated (active). The phosphorylated protein has a slower mobility in SDS-PAGE and can therefore be compared with the unstimulated protein using Western blotting. Alternatively, antibodies specific for the phosphorylated protein are available (New England Biolabs) which can be used to detect an increase in the phosphorylated kinase. In either method, cells are stimulated with the test compound and then extracted with Laemmli buffer. The soluble fraction is applied to an SDS-PAGE gel and proteins are transferred electrophoretically to nitrocellulose or Immobilon. Immunoreactive bands are detected by standard Western blotting technique. Visible or chemiluminescent signals are recorded on film and may be quantified by densitometry.

Another approach is based on evaluation of the MAP kinase activity via a phosphorylation assay. Cells are stimulated with the test compound and a soluble extract is prepared. The extract is incubated at 30° C. for 10 min with $\gamma$-$^{32}$P-ATP, an ATP regenerating system, and a specific substrate for MAP kinase such as phosphorylated heat and acid stable protein regulated by insulin, or PHAS-I. The reaction is terminated by the addition of $H_3PO_4$ and samples are transferred to ice. An aliquot is spotted onto Whatman P81 chromatography paper, which retains the phosphorylated protein. The chromatography paper is washed and counted for $^{32}$P in a liquid scintillation counter. Alternatively, the cell extract is incubated with $\gamma^{32}$ P ATP, an ATP regenerating system, and biotinylated myelin basic protein bound by streptavidin to a filter support. The myelin basic protein is a substrate for activated MAP kinase. The phosphorylation reaction is carried out for 10 min at 30° C. The extract can then by aspirated through the filter, which retains the phosphorylated myelin basic protein. The filter is washed and counted for $^{32}$P by liquid scintillation counting.

Cell Proliferation Assay

Receptor activation of the receptor may lead to a mitogenic or proliferative response which can be monitored via $^3$H-thymidine uptake. When cultured cells are incubated with $^3$H-thymidine, the thymidine translocates into the nuclei where it is-phosphorylated to thymidine triphosphate. The nucleotide triphosphate is then incorporated into the cellular DNA at a rate that is proportional to the rate of cell growth. Typically, cells are grown in culture for 1–3 days. Cells are forced into quiescence by the removal of serum for 24 hrs. A mitogenic agent is then added to the media. Twenty-four hours later, the cells are incubated with $^3$H-thymidine at specific activities ranging from 1 to 10 μCi/mL for 2–6 hrs. Harvesting procedures may involve trypsinization and trapping of cells by filtration over GF/C filters with or without a prior incubation in TCA to extract soluble thymidine. The filters are processed with scintillant and counted for $^3$H by liquid scintillation counting. Alternatively, adherent cells are fixed in MeOH or TCA, washed in water, and solubilized in 0.05% deoxycholate/0.1 N NaOH. The soluble extract is transferred to scintillation vials and counted for $^3$H by liquid scintillation counting.

Alternatively, cell proliferation can be assayed by measuring the expression of an endogenous or heterologous gene product, expressed by the cell line used to transfect the receptor, which can be detected by methods such as, but not limited to, florescence intensity, enzymatic activity, immunoreactivity, DNA hybridization, polymerase chain reaction, etc.

Promiscuous Second Messenger Assays

It is not possible to predict, a priori and based solely upon the GPCR sequence, which of the cell's many different signaling pathways any given receptor will naturally use. It is possible, however, to coax receptors of different functional classes to signal through a pre-selected pathway through the use of promiscuous G-alpha. subunits. For example, by providing a cell based receptor assay system with an endogenously supplied promiscuous G-alpha subunit such as G-alpha$_{15}$ or G-alpha$_{16}$ or a chimeric G-alpha subunit such as G-alpha$_{qz}$, a GPCR, which might normally prefer to couple through a specific signaling pathway (e.g., $G_s$, $G_i$, $G_q$, $G_o$, etc.), can be made to couple through the pathway defined by the promiscuous Galpha subunit and upon agonist activation produce the second messenger associated with that subunit's pathway. In the case of G-alpha$_{15}$, G-alpha$_{16}$ and/or G-alpha$_{qz}$ this would involve activation of the $G_q$ pathway and production of the second messenger $IP_3$. Through the use of similar strategies and tools, it is possible to bias receptor signaling through pathways producing other second messengers such as $Ca^{2+}$, cAMP, and $K^+$ currents, for example (Milligan, G. and Rees, S.(1999) TIPS 20:118–124).

It follows that the promiscuous interaction of the exogenously supplied G-alpha subunit with the receptor alleviates the need to carry out a different assay for each possible signaling pathway and increases the chances of detecting a functional signal upon receptor activation.

Methods for Recording Currents in *Xenopus* oocytes

Oocytes are harvested from *Xenopus laevis* and injected with mRNA transcripts as previously described (Quick, M. W. and Lester, H. A., (1994) Meth. Neurosci. 19: 261–279; Smith et. al. (1997) J. Biol. Chem. 272: 24612–24616). The test receptor of this invention and G-alpha. subunit RNA transcripts are synthesized using the T7 polymerase ("Message Machine," Ambion) from linearized plasmids or PCR products containing the complete coding region of the genes. Oocytes are injected with 10 ng synthetic receptor RNA and incubated for 3–8 days at 17 degrees. Three to eight hours prior to recording, oocytes are injected with 500 pg promiscuous G-alpha. subunits mRNA in order to observe coupling to $Ca^{2+}$ activated Cl-currents. Dual electrode voltage clamp (Axon Instruments Inc.) is performed using 3 M KCl-filled glass microelectrodes having resistances of 1–2 MOhm. Unless otherwise specified, oocytes are voltage clamped at a holding potential of −80 mV. During recordings, oocytes are bathed in continuously flowing (1–3 mL/min) medium containing 96 mM NaCl, 2 mM KCl, 1.8 mM $CaCl_2$, 1 mM $MgCl_2$, and 5 mM HEPES, pH 7.5 (ND96). Drugs are applied either by local perfusion from a 10 μL glass capillary tube fixed at a distance of 0.5 mm from the oocyte, or by switching from a series of gravity fed perfusion lines.

Other oocytes may be injected with a mixture of receptor mRNAs and synthetic mRNA encoding the genes for G-protein-activated inward rectifier channels (GIRK1 and GIRK4, U.S. Pat. Nos. 5,734,021 and 5,728,535 or GIRK1 and GIRK2) or any other appropriate combinations (see, e.g., Inanobe, A. et. al. (1999) J. of Neurosci. 19(3): 1006–1017). Genes encoding G-protein inwardly rectifying $K^+$ (GIRK) channels 1, 2 and 4 (GIRK1, GIRK2, and GIRK4) may be obtained by PCR using the published sequences (Kubo, Y. et al., Nature 364:802–806 (1993); Dascal et al., Proc. Natl. Acad. Sci. USA 90:10235–10239 (1993); Krapivinsky et. al., Nature 374:135–141 (1995) and J. Biol. Chem. 270: 28777–28779 (1995)) to derive appropriate 5' and 3' primers. Human heart or brain cDNA may be used as template together with appropriate primers.

Heterologous expression of GPCRs in *Xenopus* oocytes has been widely used to determine the identity of signaling pathways activated by agonist stimulation (Gundersen, C. B. et al. (1983), Proc. R. Soc. Lond. B. Biol. Sci. 219(1214): 103–109; Takahashi et al. (1987), Proc. Natl. Acad. Sci. USA 84(14):5063–5067). Activation of the phospholipase C (PLC) pathway is assayed by applying a test compound in ND96 solution to oocytes previously injected with mRNA for the OSGPR116 receptor and observing inward currents at a holding potential of approximately −80 mV. The appearance of currents that reverse at −25 mV and display other properties of the Ca2+-activated Cl-channel is indicative of receptor-activation of PLC and release of $IP_3$ and intracellular $Ca^{2+}$. Such activity is exhibited by GPCRs that couple to Gq or $G_{11}$.

Involvement of the Gi/o class of G-proteins in GPCR-stimulated Ca2+-activated Cl-currents is evaluated using PTX, a toxin which inactivates Gi/o G-proteins. Oocytes are injected with 25 ng PTX/oocyte and modulation of Ca2+-activated Cl-currents by OSGPR116 receptor is evaluated 2–5 h subsequently.

Elevation of intracellular cAMP can be monitored in oocytes by expression of the cystic fibrosis transmembrane conductance regulator (CFTR) whose Cl⁻-selective pore opens in response to phosphorylation by protein kinase A (Riordan, J. R. (1993) Ann. Rev. Physiol. 55: 609–630). In order to prepare RNA transcripts for expression in oocytes, a template is created by PCR using 5' and 3' primers derived from the published sequence of the CFTR gene (Riordan, J. R. (1993) Ann. Rev. Physiol. 55: 609–630). The 5' primer includes the sequence coding for T7 polymerase so that transcripts can be generated directly from the PCR products without cloning. Oocytes are injected with 10 ng of CFTR mRNA in addition to 10–15 ng mRNA for OSGPR116. Electrophysiological recordings are made in ND96 solution after a 2–3 day incubation at 18° C. Currents are recorded under dual electrode voltage clamp (Axon Instruments Inc.) with 3 M KCl-filled glass microelectrodes having resistances of 1–2 Mohm. Unless otherwise specified, oocytes are voltage clamped at a holding potential of −80 mV. During recordings, oocytes are bathed in continuously flowing (1–3 mL/min) medium containing 96 mM NaCl, 2 mM KCl, 1.8 mM $CaCl_2$, 1 mM $MgCl_2$, and 5 mM HEPES, pH 7.5 (ND96). Drugs are applied either by local perfusion from a 10 μL glass capillary tube fixed at a distance of 0.5 mm from the oocyte, or by switching from a series of gravity fed perfusion lines.

Activation of G-protein $G_i$ and $G_o$ can be monitored by measuring the activity of inwardly rectifying $K^+$ (potassium) channels (GIRKs). Activity may be monitored in oocytes that have been co-injected with mRNAs encoding the mammalian receptor plus GIRK subunits. GIRK gene products co-assemble to form a G-protein activated potassium channel known to be activated (i.e., stimulated) by a number of GPCRs that couple to $G_i$ or $G_o$ (Kubo, Y. et al. (1993), Nature 364:802–806; Dascal et al. (1993), Proc. Natl. Acad. Sci. USA 90:10235–10239). Oocytes expressing the mammalian receptor plus the GIRK subunits are tested for test compound responsivity by measuring $K^+$ currents in elevated $K^+$ solution containing 49 mM $K^+$.

In Vivo Feeding Experiments

For the acute feeding experiment, the experimental conditions used as closely as possible replicated those of de Fonseca, F. R. et.al. (2001) Nature, 414:209–212. Briefly, rats were starved for 24h. Oleoylethanolamide (3 and 10 mg/kg i.p.) or vehicle was administered 15 minutes prior to the availability of food. Oleoylethanolamide was dissolved in dimethylsulfoxide (DMSO) and administered in a 70% DMSO in sterile water solution. Following presentation of food, food intake (grams) was measured at 1, 2, 3 and 4h intervals and the results compared to a normal feeding and vehicle treated control group.

Results

Cloning of the Full Length Sequences of OSGPR116

The human OSGPR116 receptor (FIG. 2) shares the highest homology with several known G-protein coupled receptors, including β-adrenoceptors and dopamine receptors. Homology clustering analysis with OSGPR116 indicates that it aligns most closely to the cannabinoid and Edg family of G-protein coupled receptors. The mouse homolog (FIG. 4) demonstrates a high homology with its human counterpart; 84% at the nucleotide level (FIG. 3).

Expression Profiling Analysis

Gene expression analysis, by quantitative RT-PCR indicates that there is a discrete expression of the receptor in normal human tissues (FIG. 7). The highest expression levels (normalized to TFIIB expression) were observed in the pancreas, with additional expression in the colon, small intestine and adipose tissue. Expression of the receptor in other tissues was low relative to these levels. The pancreas is known to secrete a number of locally and distantly acting hormones, such as insulin, many of which are directly or indirectly, associated with control of blood sugars, and cellular metabolism. Expression of the receptor in colon and small intestine may also predict that this receptor may play a role in the control of absorption of nutrients, whether through a hormonal action or as a more specific nutrient sensor. Similarly, expression of the receptor in adipose tissue could also suggest a role in the maintenance of blood lipid levels. Whether the receptor is involved in uptake or release of lipids is presently unclear.

A number of human cell lines, from both malignant and non-malignant sources were also tested for expression of OSGPR116 (FIG. 8). The cells used for expression analysis were chosen primarily on the basis of tissue sources known to express the receptor (such as pancreas), as well as an assortment of cells from other tissue origins. The ovarian cancer cell line OvCar-3 was found to express the highest levels of OSGPR116. The pancreatic cell line ASPC-1, the hepatoma HepG2 cell line and colon cancer line T84 cells were all demonstrated to express moderate levels of OSGPR116. Additionally, HPAC, LoVo, Cappan-2, Caco-2, MiaPaCa-2, 577MF and BXPC1 cells lines all had demonstrable, albeit very low, levels of receptor gene expression. In addition to expression of the receptor in cell lines derived from tissues that normally express the receptor (For example, expression of the receptor in pancreatic and colon cell lines) the receptor is also expressed in cell lines, both malignant and non-malignant, derived from tissues that normally do not express the receptor (such as the ovarian cancer cell line OvCar3—normal ovaries do not express significant amounts of the receptor)

In summary, the distribution of OSGPR116 implies a probable role of this receptor in feeding, energy balance and metabolic processes although the distribution in other regions, and in malignant cell lines may imply a role in processes such as, but not limited to, feeding regulation, obesity, diabetes, cachexia, heart disease and circulatory disorders, immune system function, allergies, inflammatory bowel disease and related disorders, cancer, cell proliferation, apoptosis.

Yeast-based Reporter Assays

Figure 9A:
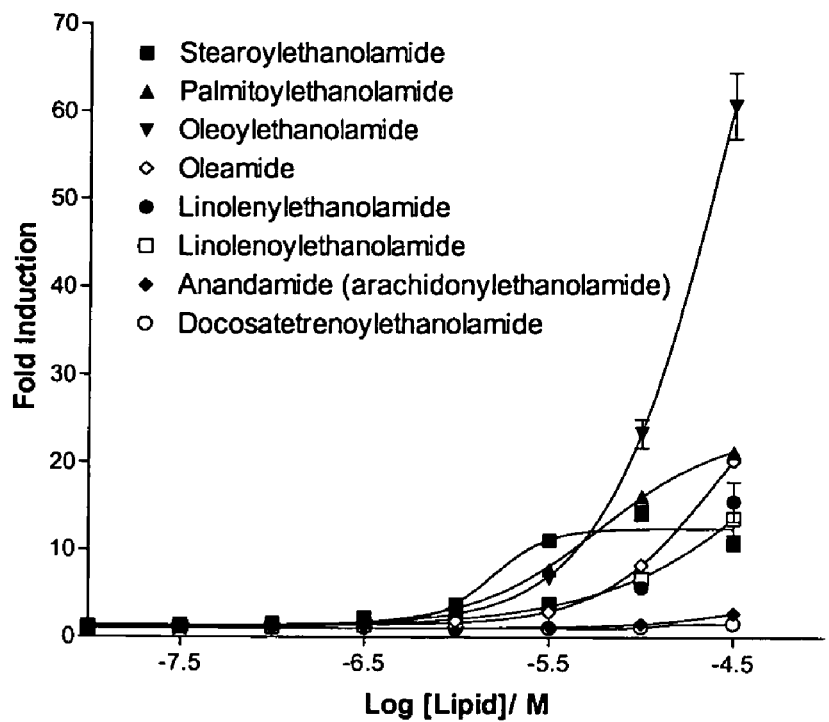
FIG. 9: Effects of fatty acid amides at human (9a) and mouse (9b) isoforms of OSGPR116. The experiment was conducted as detailed in the Materials and Methods section. Briefly, engineered yeast cells expressing a Galpha-q5 subunit and two reporter genes, URA-Fus1p-LacZ and TRP-Fus1p-LacZ were incubated with different lipid ethanolamides and related compounds. The yeast cells were tested with and without OSGPR116 expression. β-galactosidase activity was measured and the result expressed as a fold-induction over basal β-galactosidase activity.
Figure 9B:
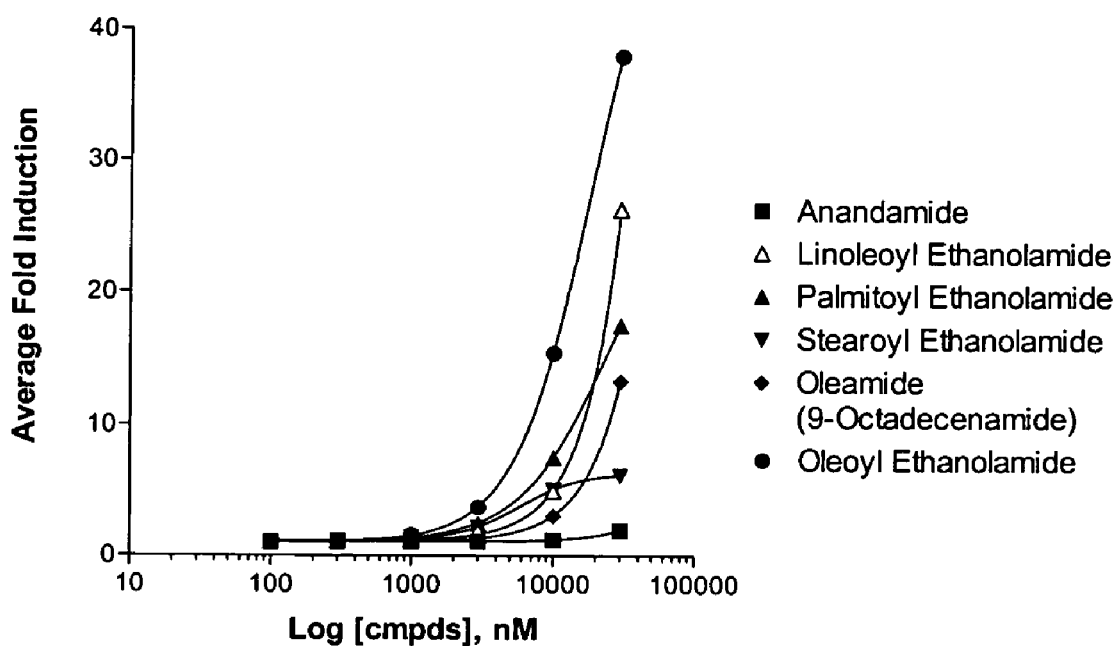

Co-expression of the receptor and the reporter genes in yeast imparts a triple selection benefit to the yeast, allowing them to grow in a LEU-URA-TRP deficient media. Colonies that grew on SD-LUT(−) plates, and therefore expressed the plasmids of interest, were tested in the fluorogenic β-galactosidase assay. Due to the homology clustering analysis that indicated that the closest relatives of this orphan GPCR were the cannabinoid receptors, a number of cannabinoid ligands, and related lipid ethanolamides were tested in the assay. Additionally, the experiments described in U.S. Pat. No. 6,221,660 had suggested that all-trans-retinoic acid (ATRA) activates this receptor, and so this compound was also tested in the assay. ATRA was found to have no effect in the yeast-based assay, nor did longer chain polyunsaturated fatty acid ethanolamides such as docosahexaenoic acid ethanolamide. The endogenous cannabinoid 2-arachidonyl glycerol and synthetic cannabinoid ligands (CP55940, WIN55212-2, methanandamide, JWH-133) also had no effect in the assay. However, anandamide (C22: 4–fatty acid chain length=22 carbons with 4 double bonds), linolenoyl ethanolamide (C18:3), linoleoyl ethanolamide (C18:2), oleoyl ethanolamide (C18:1), stearoyl ethanolamide (C18:0), palmitoyl ethanolamide (C16:0) and oleamide (the primary amide of oleic acid) were all shown to cause an increase in fluorescence in yeast transformed with OSGPR116 receptor, but not in vector transformed cells (FIGS. 9a, 9b). Oleoyl ethanolamide was the most efficacious and potent of the compounds tested.

Figure 10:
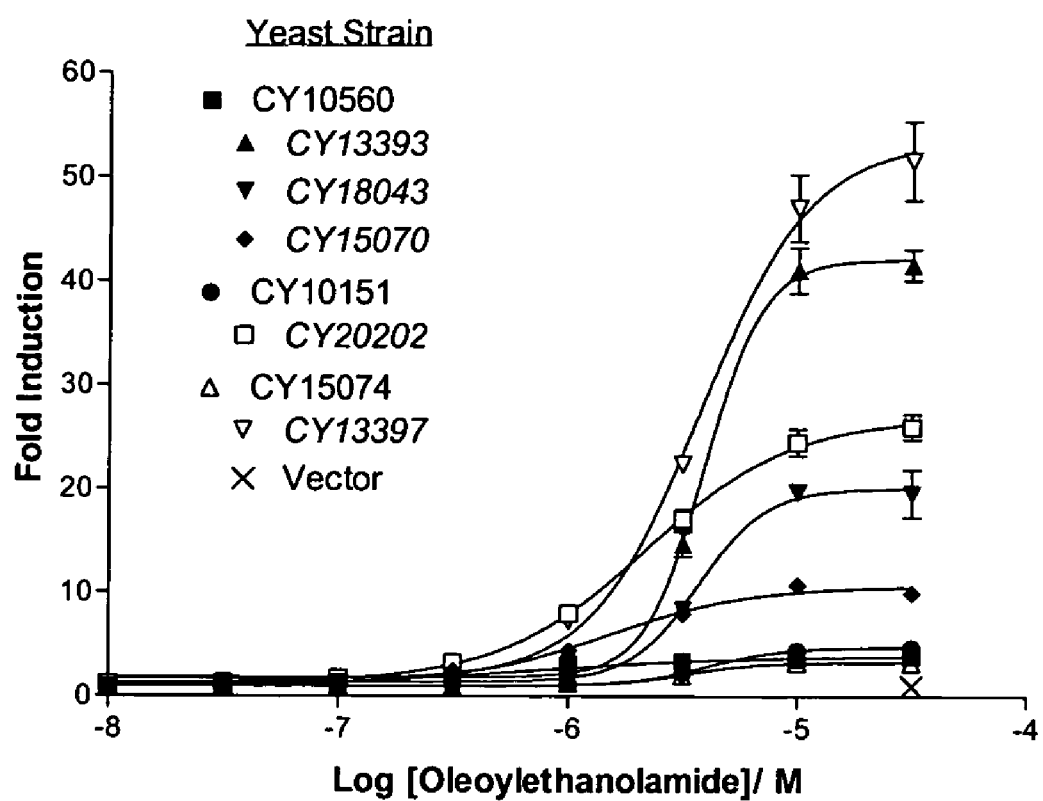
FIG. 10: Effects of oleoylethanolamide in different yeast strains. Different yeast strains contained different G-alpha chimeric proteins. The experiment was conducted as detailed in the Materials and Methods section. Briefly, engineered yeast cells expressing G-alpha chimeric subunits and two reporter genes, URA-Fus1p-LacZ and TRP-Fus1p-LacZ were incubated with different fatty acid amides. The yeast cells were tested with and without OSGPR116 expression. β-galactosidase activity was measured and the result expressed as a fold-induction over basal β-galactosidase activity.

Multiple yeast strains with different G-protein chimeras were also tested for optimal response to oleoyl ethanolamide and several but not all strains responded to ligand induction. This is normal. Generally, the G alpha chimeras have been designed to mimic mammalian receptors as closely as possible. In a mammalian system, receptors which couple to G-alpha i/o family will not respond in a G-alpha-q based read-out. It was found that using the yeast assay chimeras of each of the three major families G-alpha-q (13397), G-alpha-i (13393, 15070, 18043) and G-alpha-s (20202, 10151) could produce a response to oleoylethanolamide in OSGPR116-transformed yeast (FIG. 10). Vector controls in the same yeast strains did not respond to oleoyl ethanolamide. Comparison between the mouse and human forms of OSGPR116 demonstrate that, despite the relatively low homology across the species isoforms, the pharmacology of the receptors was identical. The work described in U.S. Pat. No. 6,468,756 has demonstrated that the mouse receptor differs from the human receptor in one significant way—the mouse receptor is expressed at high levels in the CNS; whereas both U.S. Pat. No. 6,468,756 and the data generated in this study show that human OSGPR116 is not expressed in the CNS at high levels.

The identification of a receptor that is activated by lipid ethanolamides with shorter chain lengths and lesser degrees of side-chain saturation than the cannabinoid receptors is of great interest and allows for a speculation as to the potential role of this receptor in the body. At least three of the compounds that have been shown to activate the receptor have extensive literature regarding their effects in multiple assay systems. Palmitoylethanolamide has been recognized as an immune system modulator since the 1960's (e.g. see Schmid H. H., et. al. (1990) Prog. Lipid Res. 29:1–43), although a molecular mechanism of action has never been satisfactorily described. There have been reports that it may act as a CB2 receptor agonist, although there are multiple other manuscripts refuting this possibility. Oleamide was originally identified as one of the principal sleep-inducing factors (e.g. see Cravatt B. F., et. al. Science. (1995) 268: 1506–9) and was originally identified in this role from its isolation from the CSF of sleep-deprived cats. However, our expression analysis for OSGPR116 suggests that the human receptor is not present at high concentrations in cells of the immune system or CNS. Thus, further study will be necessary to demonstate a role for OSGPR116 in these effects of palmitoylethanolamide and oleamide.

However, oleoylethanolamide has recently been described to act as a peripheral modulator of feeding in de Fonseca, F. R. et.al. (2001) Nature, 414:209–212). The expression profile of OSGPR116 is consistent with this role, with the receptor localization predominantly occurring in the pancreas, small intestine and colon. This evidence leads to the hypothesis that OSGPR116 activation may play a critical role in the regulation of feeding, and that drugs targeting OSGPR116 by either activating the receptor, or it's downstream signaling pathways, may provide a unique pharmaceutical target for drugs designed to reduce appetite. The application of such drugs to obesity, diabetes and pathophysiological conditions associated with obesity could be of therapeutic benefit.

In summary, OSGPR116, when expressed in yeast responds to lipid ethanolamides of shorter chain lengths and degrees of saturation than the related cannabinoid receptors. This is in contradiction to the work described in U.S. Pat. No. 6,221,660, that suggested certain retinoids activated the receptor. Such conclusions could not be reproduced the studies described herein. In terms of efficacy and potency, the optimal endogenously produced agonist of OSGPR116 is oleoylethanolamide. Based on our understanding of the physiological effects of oleoylethanolamide and its role in feeding, OSGPR116 may represent a molecular mechanism by which these effects may be mediated and therefore a unique target for therapeutic intervention in relevant diseases.

Mammalian Cell Based Assays

ASPC-1 cells shown to endogenously express OSGPR116 were tested for a cAMP response to oleoylethanolamide. G-protein coupled receptors which signal through Gi/o proteins are known to cause inhibition of the accumulation of cyclic AMP due to an inhibition of the adenylate cyclase family of enzymes. Cannabinoid CB1 and CB2 receptors are examples of receptors that predominantly couple to Gi/o proteins. Similarly, receptors that predominantly couple to Gs proteins cause an increase in cAMP production due to a stimulation of the adenylate cyclase enzymes. B-adrenoceptors are examples that have been shown to couple through Gs. Addition of oleoylethanolamide, at a concentration of 10 μM, did not cause an increase in cAMP production (FIG. 11), suggesting that this receptor, under these experimental conditions, does not couple to Gs proteins, as suggested by U.S. Pat. No. 6,221,660. However, the same concentration caused an inhibition of forskolin-stimulated cAMP accumulation. Forskolin is used to pharmacologically stimulate adenylate cyclase enzymes. This inhibition of adenylate cyclase is consistent with an ability of the receptor to couple to a Gi/o protein.

Figure 12:
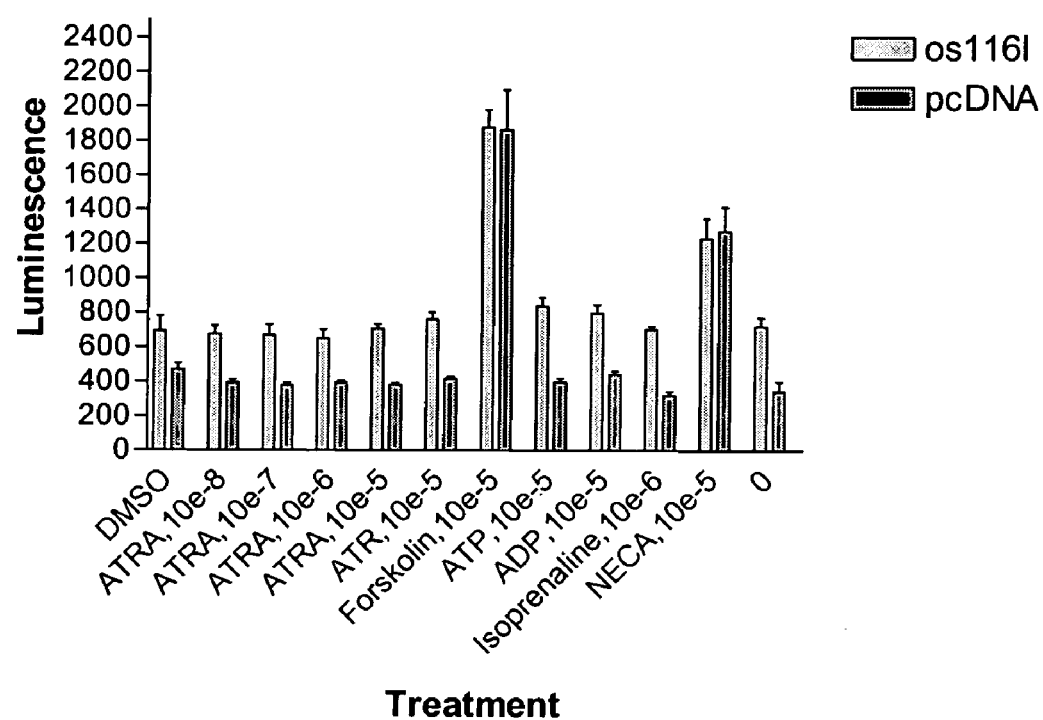
FIG. 12: Lack of effect of all-trans retinoic acid (ATRA) on cAMP response element stimulation of secreted alkaline phosphatase in OSGPR116 and empty vector transformed CHO cells.

Using a HEK-Galpha16 cell line that contains the cre-SEAP reporter, [a cyclic AMP response element driving a secreted alkaline phosphatase read-out] OSGPR116 in a mammalian expression vector (pcDNA3.1), or the empty vector was transfected into the cells using lipofectamine. This assay has previously been shown to respond to stimulation of Gs coupled receptors. The response to ATRA, forskolin, ATP and NECA (a non-specific adenosine receptor agonist) was compared (FIG. 12). A clear increase in luminescence was seen with NECA and forskolin whereas ATRA (and ATP) had no effect.

Effect of oleoylethanolamide on feeding in fasted rats.

Figure 13:
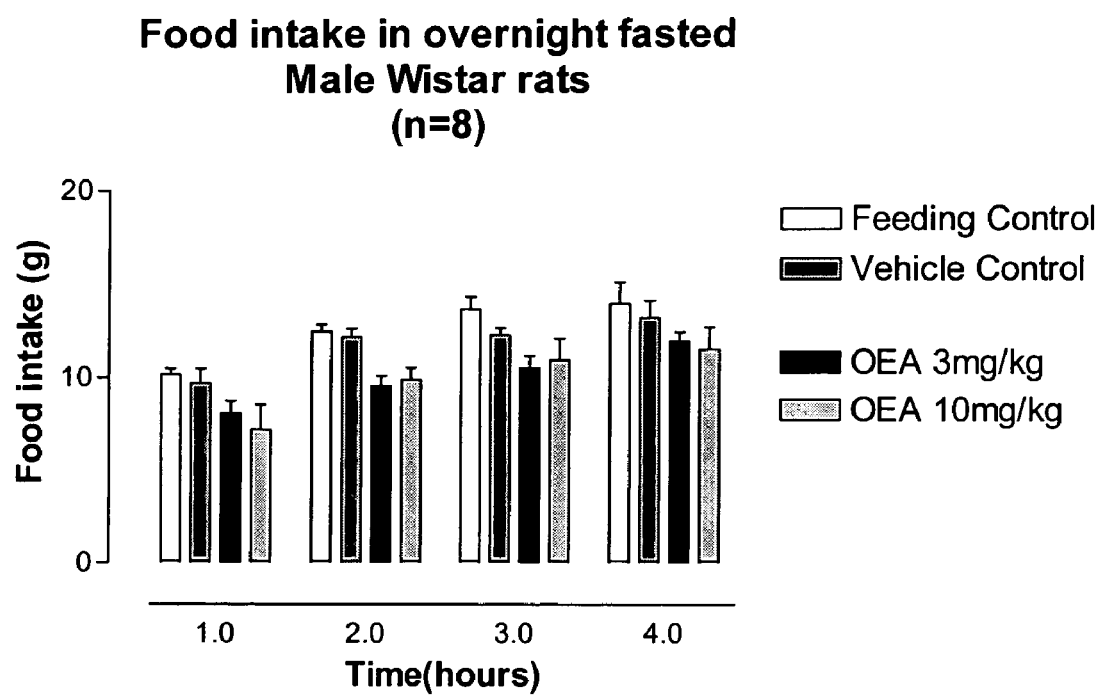
FIG. 13: Effect of oleoylethanolamide on feeding in different rat feeding models. Briefly, male Wistar rats were fasted overnight. On the day of testing, oleoylethanolamide (3 or 10 mg/kg) or vehicle was administered i.p. and food intake measured over a 4h period.

In an attempt to replicate and initially confirm the findings of de Fonseca, F. R. et.al. (2001) Nature, 414:209–212), the effect of oleoylethanolamide on feeding in overnight fasted Wistar rats was tested. The data confirms that at concentrations of 3 and 10 mg/kg i.p., oleoylethanolamide caused an inhibition of feeding at 1 and 2h post-treatment (FIG. 13). The degree of inhibition of feeding induced by oleoylethanolamide is less than was reported by De Fonseca et al., which most likely represents slight differences in the protocol. This experiment confirms the observation that oleoylethanolamide can act as a regulator of feeding.

Incorporation by Reference

All patents, published patent applications and other references disclosed herein are hereby expressly incorporated herein by reference.

EQUIVALENTS

Those skilled in the art will recognize, or be able to ascertain, using no more than routine experimentation, many equivalents to specific embodiments of the invention described specifically herein. Such equivalents are intended to be encompassed in the scope of the following claims.

What is claimed is:

1. A method involving competitive binding for identifying a chemical compound which specifically binds to a mammalian OSGPR116 receptor which comprises separately contacting isolated cells expressing on their cell surface a mammalian OSGPR116 receptor, wherein said mammalian OSGPR116 receptor comprises an amino acid sequence having at least 95% identity to SEQ ID NO:2, SEQ ID NO:4, or rat OSGPR116 receptor, wherein fatty acid amide ligands that bind the receptor activate G-proteins, and wherein such cells do not normally express a mammalian OSGPR116 receptor, with both the chemical compound and a fatty acid amide ligand, known to bind to the receptor, wherein the fatty acid amide ligand is oleoyl ethanolamide, palmitoyl ethanolamide, stearoyl ethanolamide, linoleoyl ethanolamide, linolenoyl ethanolamide or oleamide, and with only the ligand, under conditions suitable for binding of such a ligand to the receptor, and detecting specific binding of the chemical compound to said mammalian OSGPR116 receptor, a decrease in the binding of the ligand to said mammalian OSGPR116 receptor in the presence of the chemical compound being tested indicating that such chemical compound binds to said mammalian OSGPR116 receptor.

2. The method of claim 1, wherein the fatty acid amide ligand for the mammalian OSGPR116 receptor is oleoyl ethanolamide.

3. The method of claim 1, wherein the mammalian OSGPR116 receptor is a human OSGPR116 receptor with the amino acid sequence of SEQ ID NO:2.

4. The method of claim 1, wherein the cells are insect cells.

5. The method of claim 1, wherein the cells are mammalian cells.

6. The method of claim 1, wherein the cells are human cells.

7. The method of claim 1, wherein the cells are yeast cells.

8. The method of claim 5, wherein the mammalian cells are COS-7 cells, 293 human embryonic kidney cells, CHO cells, NIH-3T3 cells, or mouse Y1 cells.

9. A method involving competitive binding for identifying a chemical compound which specifically binds to a mammalian OSGPR116 receptor which comprises separately contacting a membrane preparation from cells expressing on their cell surface a mammalian OSGPR116 receptor, wherein said mammalian OSGPR116 receptor comprises an amino acid sequence having at least 95% identity to SEQ ID NO:2, SEQ ID NO:4, or rat OSGPR116 receptor, wherein fatty acid amide ligands that bind the receptor activate G-proteins, and wherein such cells do not normally express a mammalian OSGPR116 receptor, with both the chemical compound and a fatty acid amide ligand, known to bind to the receptor, wherein the fatty acid amide ligand is oleoyl ethanolamide, palmitoyl ethanolamide, stearoyl ethanolamide, linoleoyl ethanolamide, linolenoyl ethanolamide or oleamide, and with only the ligand, under conditions suitable for binding of such a ligand to the receptor, and detecting specific binding of the chemical compound to said mammalian OSGPR116 receptor, a decrease in the binding of the ligand to said mammalian OSGPR116 receptor in the presence of the chemical compound being tested indicating that such chemical compound binds to said mammalian OSGPR116 receptor.

10. The method of claim 9, wherein the fatty acid amide ligand for the mammalian OSGPR116 receptor is oleoyl ethanolamide.

11. The method of claim 9, wherein the mammalian OSGPR116 receptor is a human OSGPR116 receptor with the amino acid sequence of SEQ ID NO:2.

12. The method of claim 9, wherein the cells are insect cells.

13. The method of claim 9, wherein the cells are mammalian cells.

14. The method of claim 9, wherein the cells are human cells.

15. The method of claim 9, wherein the cells are yeast cells.

16. The method of claim 13, wherein the mammalian cells are COS-7 cells, 293 human embryonic kidney cells, CHO cells, NIH-3T3 cells, or mouse Y1 cells.

17. A method of screening a plurality of chemical compounds not known to bind to a mammalian OSGPR116 receptor to identify a compound which specifically binds to a mammalian OSGPR116 receptor, which comprises (a) contacting isolated cells transfected with and expressing DNA encoding a mammalian OSGPR116 receptor, wherein said mammalian OSGPR116 receptor comprises an amino acid sequence having at least 95% identity to SEQ ID NO:2, SEQ ID NO:4, or rat OSGPR116 receptor, and wherein fatty acid amide ligands that bind the receptor activate G-proteins, with a fatty acid amide ligand known to bind specifically to said mammalian OSGPR116 receptor, wherein the fatty acid amide ligand is oleoyl ethanolamide, palmitoyl ethanolamide, stearoyl ethanolamide, linoleoyl ethanolamide, linolenoyl ethanolamide or oleamide;

(b) contacting the cells of step (a) with the plurality of compounds not known to bind specifically to said mammalian OSGPR116 receptor, under conditions permitting binding of compounds known to bind to said mammalian OSGPR116 receptor;

(c) determining whether the binding of the fatty acid amide ligand known to bind to said mammalian OSGPR116 receptor is reduced in the presence of the plurality of compounds, relative to the binding of the fatty acid amide ligand in the absence of the plurality of compounds; and if so (d) separately determining the binding to said mammalian OSGPR116 receptor of each compound included in the plurality of compounds, so as to thereby identify any compound included therein which specifically binds to said mammalian OSGPR116 receptor.

18. The method of claim 17 wherein the mammalian OSGPR116 receptor is a human OSGPR116 receptor with the amino acid sequence of SEQ ID NO:2.

19. The method of claim 17, wherein the cells are mammalian cells.

20. The method of claim 17, wherein the cells are human cells.

21. The method of claim 17, wherein the cells are yeast cells.

22. The method of claim 17, wherein the mammalian cells are COS-7 cells, 293 human embryonic kidney cells, CHO cells, NIH-3T3 cells, or mouse Y1 cells.

23. The method of claim 1, wherein the mammalian OSGPR116 receptor comprises an amino acid sequence having at least 99% identity to SEQ ID NO:2, SEQ ID NO:4, or rat OSGPR116 receptor, and wherein fatty acid amide ligands that bind the receptor activate G-proteins.

24. The method of claim 9, wherein the mammalian OSGPR116 receptor comprises an amino acid sequence having at least 99% identity to SEQ ID NO:2, SEQ ID NO:4, or rat OSGPR116 receptor, and wherein fatty acid amide ligands that bind the receptor activate G-proteins.

25. The method of claim 17, wherein the mammalian OSGPR116 receptor comprises an amino acid sequence having at least 99% identity to SEQ ID NO:2, SEQ ID NO:4, or rat OSGPR116 receptor, and wherein fatty acid amide ligands that bind the receptor activate G-proteins.

* * * * *